(12) United States Patent
Delahunty et al.

(10) Patent No.: US 12,714,518 B2
(45) Date of Patent: Aug. 25, 2026

(54) PROCEDURE INFORMATION OVERLAY OVER ANGIOGRAPHY DATA

(71) Applicant: Medtronic Vascular, Inc., Santa Rosa, CA (US)

(72) Inventors: James Delahunty, Galway (IE); Brian J. Kelly, Oranmore (IE); Jeffrey M. Zalewski, Corte Madera, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 19/104,956

(22) PCT Filed: Jun. 6, 2023

(86) PCT No.: PCT/US2023/024613
§ 371 (c)(1),
(2) Date: Feb. 19, 2025

(87) PCT Pub. No.: WO2024/058837
PCT Pub. Date: Mar. 21, 2024

(65) Prior Publication Data

US 2026/0069367 A1 Mar. 12, 2026

Related U.S. Application Data

(60) Provisional application No. 63/375,816, filed on Sep. 15, 2022.

(51) Int. Cl.
*A61B 34/00* (2016.01)
*A61B 34/20* (2016.01)
(Continued)

(52) U.S. Cl.
CPC .............. *A61B 34/25* (2016.02); *A61B 34/20* (2016.02); *G16H 20/10* (2018.01); *G16H 20/40* (2018.01);
(Continued)

(58) Field of Classification Search
CPC ......... A61B 6/504; A61B 6/481; A61B 6/032; A61B 6/5217; A61B 6/037; A61B 8/5223;
(Continued)

(56) References Cited

U.S. PATENT DOCUMENTS

2015/0100290 A1* 4/2015 Falt ........................ G16H 50/50 703/2
2020/0337773 A1* 10/2020 Rawlinson ................ G06T 7/13
2021/0319558 A1* 10/2021 Min ....................... A61B 6/481

OTHER PUBLICATIONS

International Preliminary Report on Patentability from International Application No. PCT/US2023/024613 dated Mar. 27, 2025, 11 pp.
(Continued)

*Primary Examiner* — Masum Billah
(74) *Attorney, Agent, or Firm* — Shumaker & Sieffert, P.A.

(57) ABSTRACT

Example systems and techniques are disclosed that may determine at least one treatment strategy for a lesion. An example system may include memory configured to store clinical guidance and/or informatics for a PCI procedure and processing circuitry communicatively coupled to the memory. The processing circuitry may be configured to determine the plurality of treatment pathways. The processing circuitry may be configured to obtain angiogram imaging data of a coronary vasculature of a patient. The processing circuitry may be configured to determine the clinical guidance and/or informatics based at least in part on the angiogram imaging data. The processing circuitry may be configured to output for display the angiogram imaging data and at least a portion of the clinical guidance and/or informatics, wherein the at least a portion of the clinical guidance and/or informatics is overlaid onto the angiogram imaging data.

19 Claims, 36 Drawing Sheets

(51) Int. Cl.
*G16H 20/10* (2018.01)
*G16H 20/40* (2018.01)
*G16H 30/20* (2018.01)
*G16H 30/40* (2018.01)
*A61B 34/10* (2016.01)

(52) U.S. Cl.
CPC ............. *G16H 30/20* (2018.01); *G16H 30/40* (2018.01); *A61B 2034/105* (2016.02); *A61B 2034/2046* (2016.02); *A61B 2034/252* (2016.02)

(58) Field of Classification Search
CPC ....... A61B 6/583; A61B 8/0891; A61B 8/587; A61B 5/0066
USPC ........................................................... 348/77
See application file for complete search history.

(56) References Cited

OTHER PUBLICATIONS

International Search Report and Written Opinion of International Application No. PCT/US2023/024613 dated Sep. 29, 2023, 14 pp.
U.S. Appl. No. 19/104,555, filed Feb. 18, 2025, by Delahunty et al.
U.S. Appl. No. 19/104,595, filed Apr. 7, 2023, by Delahunty et al.
U.S. Appl. No. 19/104,920, filed Jun. 6, 2023, by Delahunty et al.
U.S. Appl. No. 19/104,935, filed Jun. 6, 2023, by Delahunty et al.

* cited by examiner

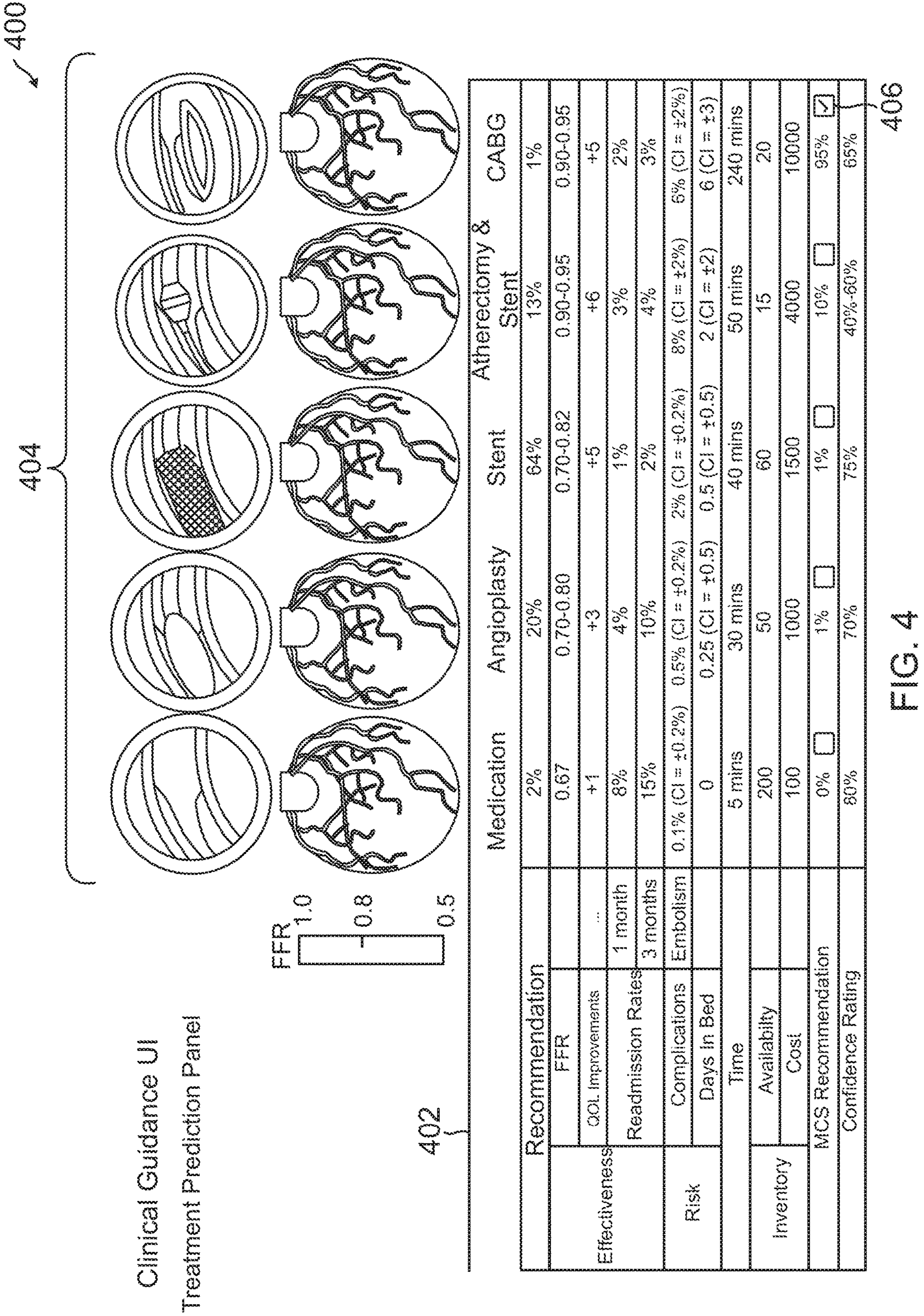

| | | | Medication | Angioplasty | Stent | Atherectomy & Stent | CABG |
|---|---|---|---|---|---|---|---|
| Recommendation | | | 2% | 20% | 64% | 13% | 1% |
| Effectiveness | FFR | | 0.67 | 0.70-0.80 | 0.70-0.82 | 0.90-0.95 | 0.90-0.95 |
| | QOL Improvements | ... | +1 | +3 | +5 | +6 | +5 |
| | Readmission Rates | 1 month | 8% | 4% | 1% | 3% | 2% |
| | | 3 months | 15% | 10% | 2% | 4% | 3% |
| Risk | Complications | Embolism | 0.1% (CI = ±0.2%) | 0.5% (CI = ±0.2%) | 2% (CI = ±0.2%) | 8% (CI = ±2%) | 6% (CI = ±2%) |
| | Days In Bed | | 0 | 0.25 (CI = ±0.5) | 0.5 (CI = ±0.5) | 2 (CI = ±2) | 6 (CI = ±3) |
| Time | | | 5 mins | 30 mins | 40 mins | 50 mins | 240 mins |
| Inventory | Availabilty | | 200 | 50 | 60 | 15 | 20 |
| | Cost | | 100 | 1000 | 1500 | 4000 | 10000 |
| MCS Recommendation | | | 0% ☐ | 1% ☐ | 1% ☐ | 10% ☐ | 95% ☑ |
| Confidence Rating | | | 80% | 70% | 75% | 40%-60% | 65% |

FIG. 4

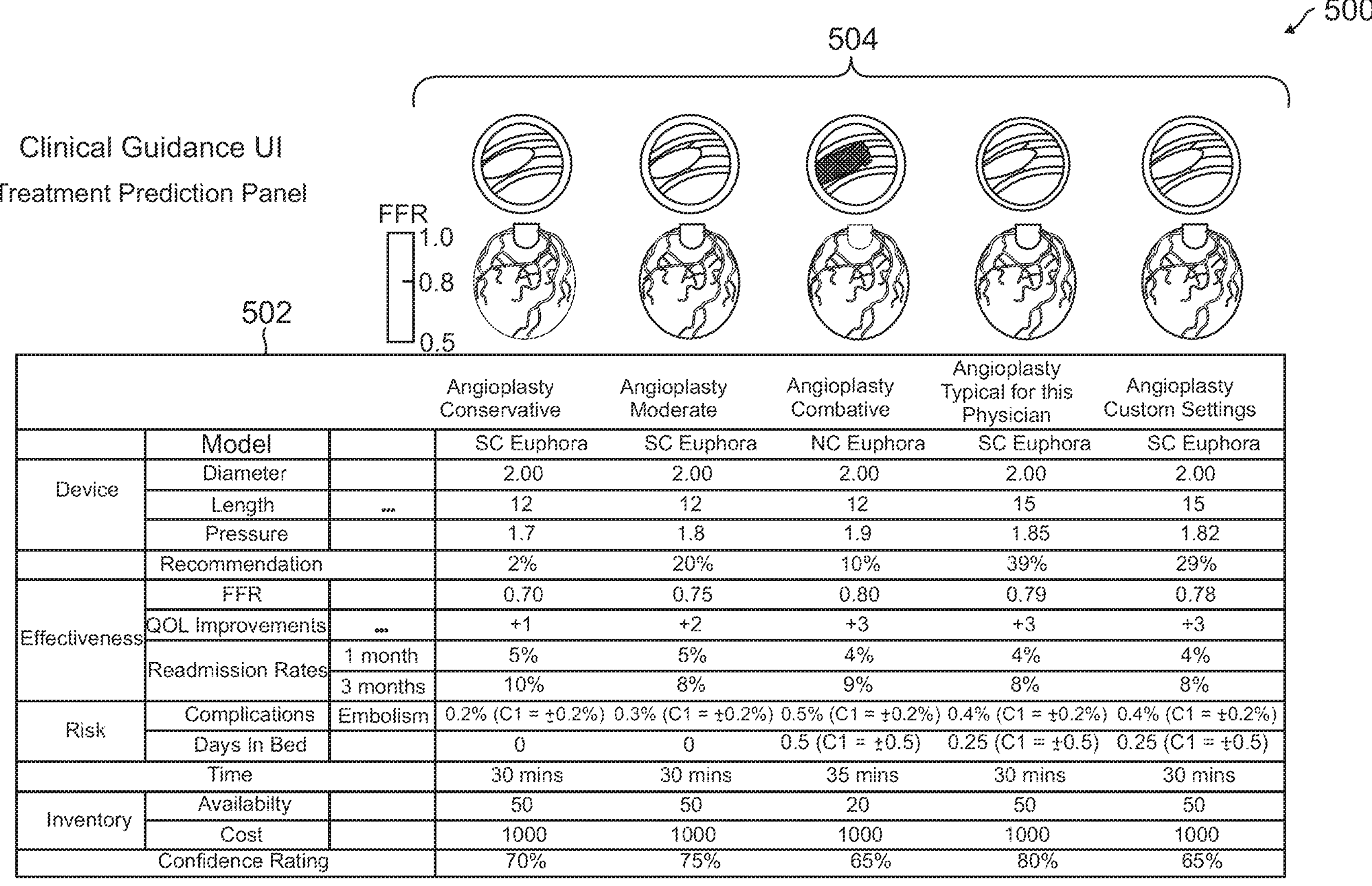

| | | | Angioplasty Conservative | Angioplasty Moderate | Angioplasty Combative | Angioplasty Typical for this Physician | Angioplasty Custom Settings |
|---|---|---|---|---|---|---|---|
| | Model | | SC Euphora | SC Euphora | NC Euphora | SC Euphora | SC Euphora |
| Device | Diameter | | 2.00 | 2.00 | 2.00 | 2.00 | 2.00 |
| | Length | ... | 12 | 12 | 12 | 15 | 15 |
| | Pressure | | 1.7 | 1.8 | 1.9 | 1.85 | 1.82 |
| | Recommendation | | 2% | 20% | 10% | 39% | 29% |
| Effectiveness | FFR | | 0.70 | 0.75 | 0.80 | 0.79 | 0.78 |
| | QOL Improvements | ... | +1 | +2 | +3 | +3 | +3 |
| | Readmission Rates | 1 month | 5% | 5% | 4% | 4% | 4% |
| | | 3 months | 10% | 8% | 9% | 8% | 8% |
| Risk | Complications | Embolism | 0.2% (C1 = ±0.2%) | 0.3% (C1 = ±0.2%) | 0.5% (C1 = ±0.2%) | 0.4% (C1 = ±0.2%) | 0.4% (C1 = ±0.2%) |
| | Days In Bed | | 0 | 0 | 0.5 (C1 = ±0.5) | 0.25 (C1 = ±0.5) | 0.25 (C1 = ±0.5) |
| Time | | | 30 mins | 30 mins | 35 mins | 30 mins | 30 mins |
| Inventory | Availabilty | | 50 | 50 | 20 | 50 | 50 |
| | Cost | | 1000 | 1000 | 1000 | 1000 | 1000 |
| Confidence Rating | | | 70% | 75% | 65% | 80% | 65% |

FIG. 5

| | Model | | SC Euphora | SC Euphora |
|---|---|---|---|---|
| Device | Diameter | | 2.00 | 2.00 |
| | Length | | 15 | 15 |
| | Pressure | | 1.85 | 1.6 |
| | Recommendation | | 39% | 29% |
| Effectiveness | FFR | | 0.79 | 0.74 |
| | QOL Improvements | ... | +3 | +2 |
| | Readmission Rates | 1 month | 4% | 5% |
| | | 3 months | 8% | 9% |
| Risk | Complications | Embolism | 0.4% (C1 = ±0.2%) | 0.3% (C1 = ±0.2%) |
| | Days In Bed | | 0.25 (C1 = ±0.5) | 0.25 (C1 = ±0.5) |
| | Time | | 30 mins | 30 mins |
| Inventory | Availabilty | | 50 | 49 |
| | Cost | | 1000 | 1000 |
| | Confidence Rating | | 80% | 85% |

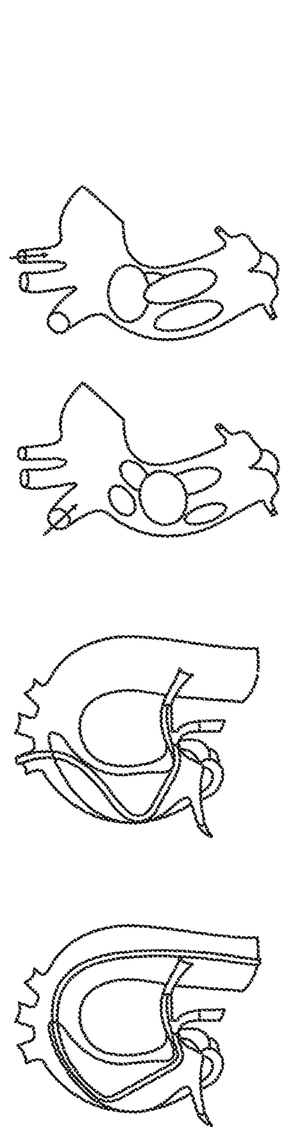
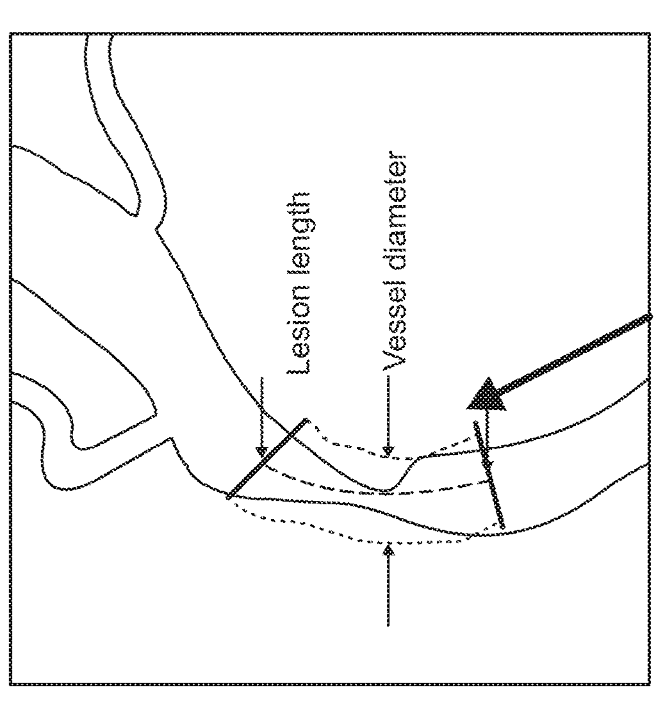
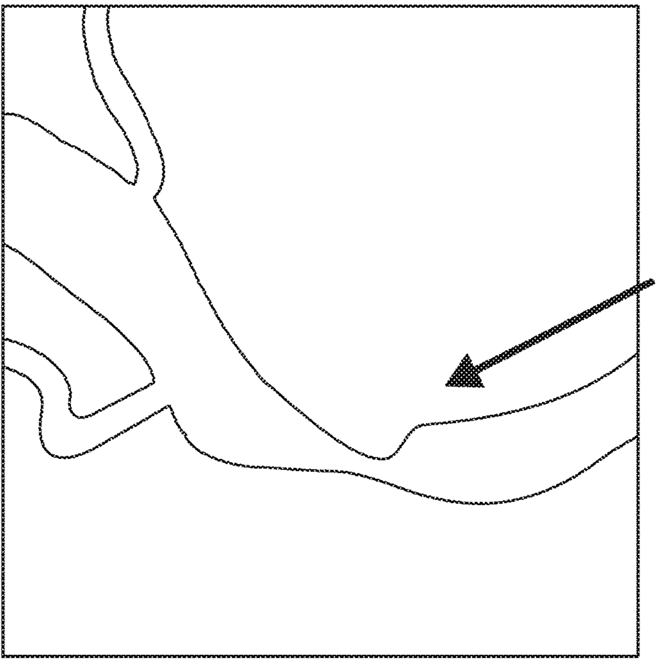
FIG. 24

| Clinical Value | Workflow Value | Economic Value | Overall Concept |
|---|---|---|---|
| -5 -4 -3 -2 -1 0 1 2 3 4 5 | -5 -4 -3 -2 -1 0 1 2 3 4 5 | -5 -4 -3 -2 -1 0 1 2 3 4 5 | -5 -4 -3 -2 -1 0 1 2 3 4 5 |

| Clinical Value | Workflow Value | Economic Value | Overall Concept |
| --- | --- | --- | --- |
| -5 -4 -3 -2 -1 0 1 2 3 4 5 | -5 -4 -3 -2 -1 0 1 2 3 4 5 | -5 -4 -3 -2 -1 0 1 2 3 4 5 | -5 -4 -3 -2 -1 0 1 2 3 4 5 |

Risk Calculator 93.1

| | |
|---|---|
| ## | Age |
| ## | Prior CABG |
| ## | Prior failure |
| ## | Proximal cap |
| ## | Tortuosity |
| ## | Calcification |
| ## | Lesion length |
| ## | Target vessel |
| ## | Collateral quality |
| ## | Other conditions |

Plan vs Actual

| | |
|---|---|
| 45.1s | Time |
| 0.7 mSv | Radiation |
| 3.4 ml | Contrast |
| 5.1 ml/s | Flow rate |
| 1 | Attempts |

Simplified 2D navigation

Plan

Cross section plan

Enhanced IVUS View

Cross section navigation

| Clinical Value | Workflow Value | Economic Value | Overall Concept |
|---|---|---|---|
| -5 -4 -3 -2 -1 0 1 2 3 4 5 | -5 -4 -3 -2 -1 0 1 2 3 4 5 | -5 -4 -3 -2 -1 0 1 2 3 4 5 | -5 -4 -3 -2 -1 0 1 2 3 4 5 |

FIG. 27

| Clinical Value | Workflow Value | Economic Value | Overall Concept |
|---|---|---|---|
| -5 -4 -3 -2 -1 0 1 2 3 4 5 | -5 -4 -3 -2 -1 0 1 2 3 4 5 | -5 -4 -3 -2 -1 0 1 2 3 4 5 | -5 -4 -3 -2 -1 0 1 2 3 4 5 |

| Clinical Value | Workflow Value | Economic Value | Overall Concept |
| --- | --- | --- | --- |
| -5 -4 -3 -2 -1 0 1 2 3 4 5 | -5 -4 -3 -2 -1 0 1 2 3 4 5 | -5 -4 -3 -2 -1 0 1 2 3 4 5 | -5 -4 -3 -2 -1 0 1 2 3 4 5 |

| Clinical Value | Workflow Value | Economic Value | Overall Concept |
|---|---|---|---|
| -5 -4 -3 -2 -1 0 1 2 3 4 5 | -5 -4 -3 -2 -1 0 1 2 3 4 5 | -5 -4 -3 -2 -1 0 1 2 3 4 5 | -5 -4 -3 -2 -1 0 1 2 3 4 5 |

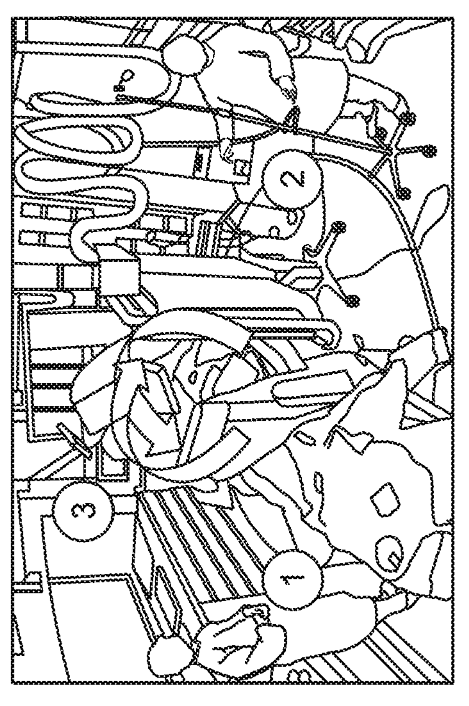
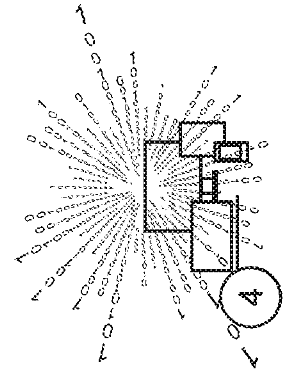
| Clinical Value | Workflow Value | Economic Value | Overall Concept |
|---|---|---|---|
| -5 -4 -3 -2 -1 0 1 2 3 4 5 | -5 -4 -3 -2 -1 0 1 2 3 4 5 | -5 -4 -3 -2 -1 0 1 2 3 4 5 | -5 -4 -3 -2 -1 0 1 2 3 4 5 |
FIG. 33

PROCEDURE INFORMATION OVERLAY OVER ANGIOGRAPHY DATA

This application is a U.S. National Stage entry under 35 U.S.C. § 371 of International Application No. PCT/US2023/024613, filed Jun. 6, 2023, which claims the benefit of 63/375,816, filed Sep. 15, 2022, the entire content of both of which is hereby incorporated by reference.

TECHNICAL FIELD

This disclosure relates to the use of images captured during a medical procedure.

BACKGROUND

During a medical procedure, a clinician may use one or more imaging systems to visualize internal anatomy of a patient. Such imaging systems may display anatomy, medical instruments, or the like, and may be used to diagnose a patient condition or assist in guiding a clinician in moving a device, such as a medical instrument to an intended location inside the patient. Imaging systems may use sensors to capture video images or still images which may be displayed during the medical procedure. Imaging systems include angiography systems, ultrasound imaging systems, computed tomography (CT) scan systems, magnetic resonance imaging (MRI) systems, isocentric C-arm fluoroscopic systems, positron emission tomography (PET) systems, intravascular ultrasound (IVUS) systems, optical coherence tomography (OCT) systems, near infrared spectroscopy (NIRS) systems, dielectric-based imaging systems, as well as other imaging systems.

SUMMARY

In general, this disclosure is directed to various techniques and medical systems for capturing images during a medical procedure and using images captured during a medical procedure to facilitate clinician decision making through enhanced imaging and, in some examples, provide clinical guidance for a clinician for use during such a medical procedure. For example, a system may use images captured during a medical procedure to determine or generate a 3D model of a coronary vasculature of a patient, which 3D model a clinician may use to diagnose a condition, to assist in visualizing areas of the vasculature which are to be addressed during the medical procedure, or the like. The system may use the images captured during the medical procedure to model different treatment pathways, assess risks associated with such treatment pathways, and present such data to the clinician. The system may overlay information, modeled devices, highlighting, or the like on angiogram imaging data for use by the clinician during the medical procedure. As used herein "angiogram imaging data" may be include still image or a moving image, such as a video. Additionally, the angiogram imaging data may be imaging data from a diagnostic procedure and/or an interventional procedure. The system may obtain imaging data from one or more imaging sources, for example, in a cardiac catheterization laboratory (Cath Lab). In other examples, the system may obtain imaging data from other sources, may be used in other healthcare environments (e.g., a surgical suite), or both.

Example medical procedures include, but are not limited to, coronary procedures (angioplasty, stenting, diagnostic catheterization, rotational or laser atherectomy, IVL), denervation procedures (e.g., renal denervation or hepatic denervation or other denervation using electrical, chemical, ultrasonic, or other energy), and structural heart procedures (e.g., catheter-based valve repair or replacement).

This disclosure describes techniques for clinical guidance applications, e.g., for catheter laboratories (Cath labs), including techniques for assembling images from a plurality of sources to create a more detailed three-dimensional (3D) model, virtual procedure modeling, and procedure overlaying on a imaging display, such as a display of a live angiogram.

The system may include one of more artificial intelligence algorithms, machine learning algorithms, computer vision algorithms, or the like which the system may utilize when generating the 3D model, modeling the different treatment pathways, assessing risks associated with such pathways, or the like. The system may update any one or more of the 3D model, the models of treatment pathways, the risks associated with the treatment pathways, the information, modeled devices, or highlighting overlaid on the angiogram imaging data live during the medical procedure.

The computer vision model may be used to identify, classify, and/or score a particular lesion. The machine learning model may be used to determine different treatment pathways, determine risks associated with such pathways, and determine a predicted chance of a successful outcome if each of the given treatment pathways were to be utilized by the clinician. In some examples, the system may be configured to recommend one of the treatment pathways for the clinician to consider, for example the treatment pathway having a relatively high predicted chance of success with a relatively low predicted risk. Such a system may aid a clinician in determining which treatment pathway to utilize for a given coronary vascular issue. For example, the system may present recommendations to the clinician and the clinician may make the final treatment decision and perform the treatment. Alternatively, or additionally, the system may be more automated. For example, the system may make a treatment determination and set one or more attributes of one or more devices within or connected to the system to facilitate or perform the determined treatment. In some examples, the system may be configured to run simulations on the different treatment pathways, such as when the training data set for any of the various algorithms discussed herein is relatively small.

Aspects of this disclosure are applicable to at least Cath Lab procedures. Example Cath lab procedures include, but are not necessarily limited to, coronary procedures, renal denervation (RDN) procedures, structural heart and aortic (SH&A) procedures (e.g., transcatheter aortic valve replacement (TAVR), transcatheter mitral valve replacement (TMVR), and the like), device implantation procedures (e.g., heart monitors, pacemakers, defibrillators, and the like), etc.

In one example, a medical system includes memory configured to store a three-dimensional (3D) model of a coronary vasculature of a patient; and processing circuitry communicatively coupled to the memory, the processing circuitry being configured to: obtain first fluoroscopy with contrast imaging data from a first viewing angle; obtain second fluoroscopy with contrast imaging data from a second viewing angle, the second viewing angle being different than the first viewing angle; determine the 3D model of the coronary vasculature of the patient based on the first fluoroscopy with contrast imaging data and the second fluoroscopy with contrast imaging data; obtain additional imaging data, the additional imaging data comprising imaging data from one or more imagers other than a fluoroscopy imager; update the 3D model based on the additional imaging data; and output for display a representation of the updated 3D model.

In another example, a method includes obtaining first fluoroscopy with contrast imaging data from a first viewing angle; obtaining second fluoroscopy with contrast imaging data from a second viewing angle, the second viewing angle being different than the first viewing angle; determining a 3D model of a coronary vasculature of a patient based on the first fluoroscopy with contrast imaging data and the second fluoroscopy with contrast imaging data; obtaining additional imaging data, the additional imaging data comprising imaging data from one or more imagers other than a fluoroscopy imager; updating the 3D model based on the additional imaging data; and outputting for display a representation of the updated 3D model.

In another example, a non-transitory computer readable medium stores instructions, which, when executed, cause processing circuitry to: obtain first fluoroscopy with contrast imaging data from a first viewing angle; obtain second fluoroscopy with contrast imaging data from a second viewing angle, the second viewing angle being different than the first viewing angle; determine a 3D model of a coronary vasculature of a patient based on the first fluoroscopy with contrast imaging data and the second fluoroscopy with contrast imaging data; obtain additional imaging data, the additional imaging data comprising imaging data from one or more imagers other than a fluoroscopy imager; update the 3D model based on the additional imaging data; and output for display a representation of the updated 3D model.

In another example, a medical system includes memory configured to store a plurality of treatment pathways; and processing circuitry communicatively coupled to the memory, the processing circuitry being configured to: determine the plurality of treatment pathways; determine, for each respective treatment pathway of the plurality of treatment pathways, one or more respective predicted effectiveness indicators associated with the respective treatment pathway, one or more respective predicted risks associated with the respective treatment pathway, and a respective confidence level associated with at least one of the respective predictions; and output for display the plurality of treatment pathways, the one or more respective predicted effectiveness indicators associated with the respective treatment pathway, the one or more respective predicted risks associated with the respective treatment pathway, and the respective confidence level associated with at least one of the respective predictions for each respective treatment pathway of the plurality of treatment pathways.

In another example, a method includes determining a plurality of treatment pathways; determining, for each respective treatment pathway of the plurality of treatment pathways, one or more respective predicted effectiveness indicators associated with the respective treatment pathway, one or more respective predicted risks associated with the respective treatment pathway, and a respective confidence level associated with at least one of the respective predictions; and outputting for display the plurality of treatment pathways, and the one or more respective predicted effectiveness indicators associated with the respective treatment pathway, the one or more respective predicted risks associated with the respective treatment pathway, and the respective confidence level associated with at least one of the respective predictions for each respective treatment pathway of the plurality of treatment pathways.

In another example, a non-transitory computer-readable storage medium stores instructions, which, when executed, cause processing circuitry to: determine a plurality of treatment pathways; determine, for each respective treatment pathway of the plurality of treatment pathways, one or more respective predicted effectiveness indicators associated with the respective treatment pathway, one or more respective predicted risks associated with the respective treatment pathway, and a respective confidence level associated with at least one of the respective predictions; and output for display the plurality of treatment pathways, and the one or more respective predicted effectiveness indicators associated with the respective treatment pathway, the one or more respective predicted risks associated with the respective treatment pathway, and the respective confidence level associated with at least one of the respective predictions for each respective treatment pathway of the plurality of treatment pathways.

In another example, a medical system includes a memory configured to store at least one of clinical guidance or informatics for a percutaneous coronary intervention (PCI) procedure; and processing circuitry communicatively coupled to the memory, the processing circuitry being configured to: obtain angiogram imaging data of a coronary vasculature of a patient; determine the at least one of the clinical guidance or the informatics based at least in part on the angiogram imaging data; and output for display the angiogram imaging data and the at least one of the clinical guidance or the informatics, wherein at least a portion of the at least one of the clinical guidance or the informatics is overlaid onto the angiogram imaging data.

In another example, a method includes obtaining angiogram imaging data of a coronary vasculature of a patient; determining at least one of clinical guidance or informatics based at least in part on the angiogram imaging data; and outputting for display the angiogram imaging data and the at least one of the clinical guidance or the informatics, wherein at least a portion of the at least one of the clinical guidance or the informatics is overlaid onto the angiogram imaging data.

In another example, a non-transitory computer-readable storage medium stores instructions, which, when executed, cause processing circuitry to: obtain angiogram imaging data of a coronary vasculature of a patient; determine at least one of clinical guidance or informatics based at least in part on the angiogram imaging data; and output for display the angiogram imaging data and the at least one of the clinical guidance or informatics, wherein at least a portion of the at least one of the clinical guidance or the informatics is overlaid onto the angiogram imaging data.

These and other aspects of the present disclosure will be apparent from the detailed description below. In no event, however, should the above summaries be construed as limitations on the claimed subject matter, which subject matter is defined solely by the attached claims.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

FIG. 4 is a conceptual diagram illustrating an example page of a user interface according to one or more aspects of this disclosure.

FIG. 5 is a conceptual diagram illustrating another example page of a user interface according to one or more aspects of this disclosure.

FIG. 24 is a conceptual diagram illustrating example device recommendation techniques according to one or more aspects of this disclosure.

FIG. 27 is a conceptual diagram illustrating an example chronic total occlusion (CTO) dashboard according to one or more aspects of this disclosure.

FIG. 33 is a conceptual diagram illustrating an example computer assisted angiogram according to one or more aspects of this disclosure.

DETAILED DESCRIPTION

Figure 1:
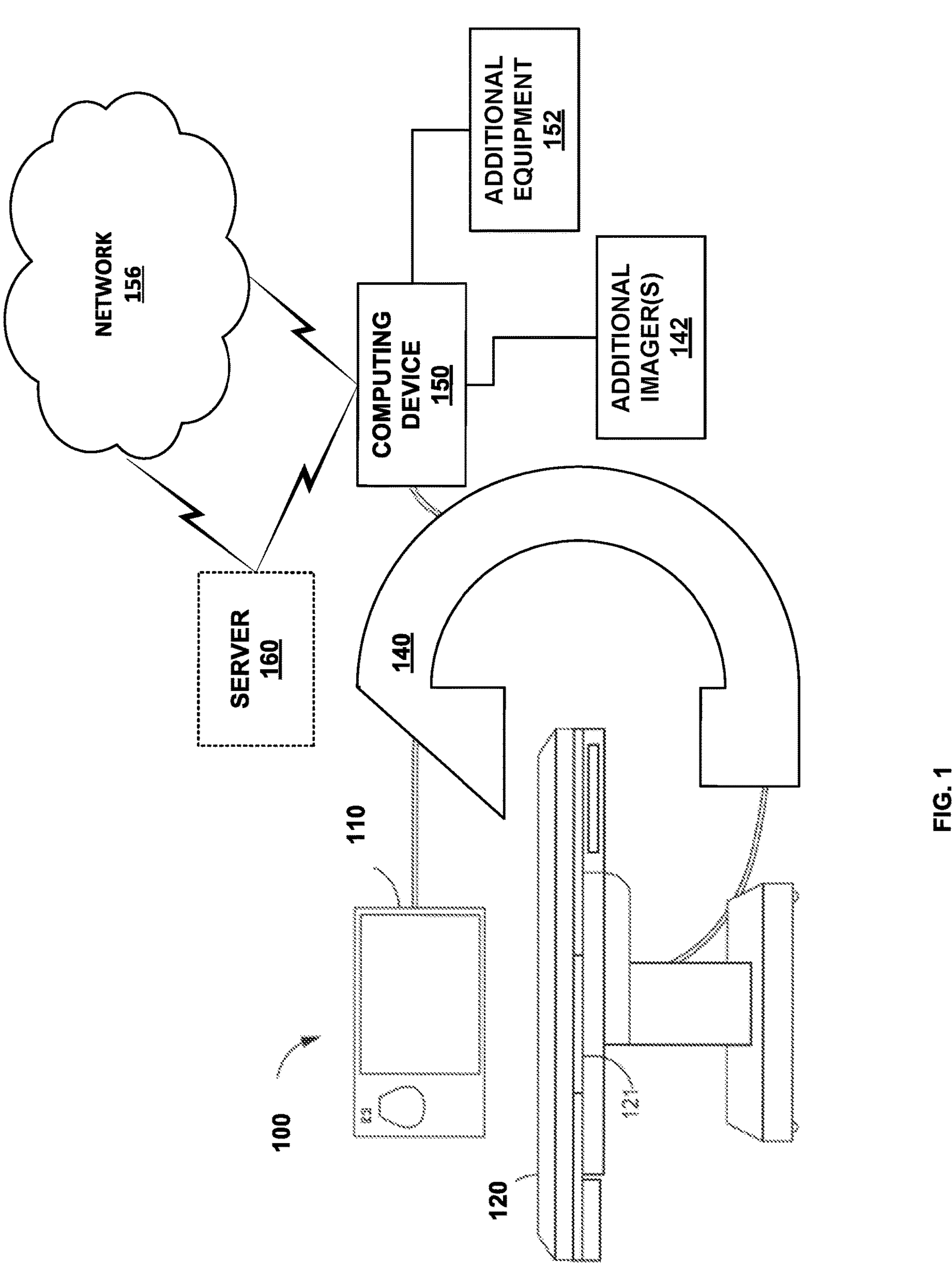
FIG. 1 is a schematic perspective view of an example of a system for performing a percutaneous coronary intervention (PCI) according to one or more aspects of this disclosure.

Imaging systems may be used to assist a clinician in a medical procedure, such as a diagnostic medical procedure, a therapeutic medical procedure, such as a percutaneous coronary intervention (PCI) procedure, an RDN procedure, a structural heart procedure, or the like, or any combination thereof. For example, imaging systems may be used to determine the presence of lesions within a vasculature of a patient that may be limiting or obstructing blood flow within the vasculature of the patient. Imaging systems may also be used when performing an ablation procedure, angioplasty procedure, or other therapeutic medical procedure intended to treat lesions within the vasculature (including the heart) of the patient. While described primarily herein with respect to the vasculature of a patient, imaging systems described herein may be used for other medical purposes and are not limited to cardiovascular purposes.

Imaging systems may generate image and/or video data via sensors. Such image and/or video data is referred to herein as imaging data. This imaging data may be used to construct a 3D model of the vasculature (e.g., coronary vasculature) of the patient, to model virtual procedures to estimate risks and outcomes of performing such procedures, and/or to present information, including imaging data, for example, on a display device.

Imaging data may include fluoroscopy imaging data, including fluoroscopy with contrast imaging data, CT imaging data, X-ray imaging data, IVUS imaging data, OCT imaging data, NIRS imaging data, MRI imaging data, ultrasound imaging data, or other imaging data.

This disclosure describes systems and techniques that may create a 3D virtual model of the coronary vasculature system of a patient. This 3D model may include or may be updated to include information such as vessel morphology, physiology, measurements, or the like. Such updates may be performed during a clinical procedure, such as a medical procedure. The updates may use imaging data from different imaging modalities, e.g., ultrasound imaging data, CT imaging data, X-ray imaging data, IVUS imaging data, OCT imaging data, MRI imaging data, PET imaging data, dielectric-based imaging data, or the like. Thus, in some examples, the 3D model may incorporate imaging data collected using a plurality of imaging modalities. A clinician may interact with the 3D model, for example, through a user interface, to gain additional information (e.g., anatomical dimensions) or insight, which may facilitate more informed planning for the procedure and to facilitate the administration of better care for the patient. In some examples, the 3D model may be used to create different virtual treatment options, predict a risk and/or an outcome for each of the virtual treatment options, and allow a clinician to make an informed selection as to which treatment option the clinician believes would provide a desired (e.g., optimal) result.

Currently, a majority of percutaneous coronary intervention (PCI) procedures, such as a coronary artery disease (CAD) assessment, are completed using only an angiogram. An angiogram provides a 2D image which clinicians may mentally attempt to convert into a 3D image and use such a mental image to determine what the clinician believes is the most effective therapy. However, such a mental conversion of a 2D image into a 3D image is unlikely to be accurate, which may lead to a selection of treatment which may be less than optimal.

The techniques of this disclosure may also provide clinicians with additional information not available in their mental 3D model, such as vessel morphology, plaque location, plaque type, vessel length, vessel diameter, fractional flow reserve (FFR) scores, SYNTAX score, or the like, which may facilitate the clinician to make more informed treatment decisions while planning how to treat a patient or while actually treating the patient. As such, the 3D virtual model techniques of this disclosure may effect a particular treatment or prophylaxis for a disease or medical condition, as such a 3D virtual model may influence a clinician to perform a particular treatment the clinician would not otherwise undertake. Various types of FFR values or scores are set forth in examples discussed herein, such as FFR, diastolic FFR (dFFR), OCT FFR (oFR), etc. It should be understood that any type of FFR may be used according to the techniques of this disclosure and not just the specific type of FFR mentioned in the examples. For example, an FFR, dFFR, vFFR, CFR, IFR, RFR, IMF, oFR, or the like may be used.

This disclosure also describes systems and techniques for virtually modeling procedures and presenting clinicians with estimated risks and outcomes of the virtually modeled procedures. Currently, a clinician may rely on experience to guide which type of procedure and which device(s) they may use when treating a patient for a particular type of lesion. As such, a clinician may choose to use a procedure and/or device(s) they feel more comfortable using even if such procedure and/or device(s) may have higher risks and/or less chance for a successful outcome than another procedure. As such, systems and techniques of this disclosure may provide a more sound and fact-based analysis of potential procedures/devices, associated risks and chances for successful outcomes for viewing and consideration by a clinician. This may lead to the clinician using a less risky and/or more advantageous procedure and/or device(s) which may improve patient outcomes. As such, the procedure modeling techniques of this disclosure may effect a particular treatment or prophylaxis for a disease or medical condition, as such modeled procedures may influence a clinician to perform a particular treatment the clinician would not otherwise undertake.

This disclosure also describes systems and techniques for displaying additional information with an angiogram, for example on a common display device, and in some cases, overlaying such information on an angiogram, such as an angiogram. The additional information may include device heat maps (e.g., indicating where a device has been, what the device has done, how long the device has been there, or the like), procedure information, procedural guidance, lesion histology, length markers, stent information, other imaging data, information from earlier procedures, or the like. By providing such information for display to a clinician, for example, during a procedure, the systems and techniques of this disclosure may facilitate the clinician in making more informed decisions regarding the procedure which may improve patient outcomes. As such, the displaying additional information with the angiogram techniques of this disclosure may effect a particular treatment or prophylaxis for a disease or medical condition, as such additional information may influence a clinician to perform a particular treatment the clinician would not otherwise undertake.

This disclosure also describes a number of user interfaces. Such user interfaces may be used for clinical guidance and/or the presentation of information (e.g., informatics), such as procedure risk(s), statistical prediction of outcome(s), analyses, or the like.

FIG. 1 is a schematic perspective view of an example of a system for performing a PCI according to one or more aspects of this disclosure. Medical system 100 may provide a system for determining a 3D model of the cardiac vasculature of a patient, modeling medical procedures (including predicting effectiveness and risks associated with such procedures), and/or overlaying information on angiogram imaging data. Such a system may facilitate a clinician to make better informed decisions prior to or during a medical procedure which may improve patient outcomes including increased FFR values, improved quality of life (QOL), and/or lower readmission rates.

System 100 includes a display device 110, a table 120, device tracking system 121, imager 140 (which may be an angiography and/or fluoroscopy imager), additional imager(s) 142, computing device 150, additional equipment 152, server 160, and network 156. System 100 may be an example of a system for use in a Cath lab, surgical ward, or other healthcare environment. In some examples, system 100 may include other devices. In some examples, system 100 may be used during a diagnostic session to diagnose cardiovascular issues for a patient. In some examples, system 100 may be used during a medical procedure (e.g., an intervention to treat a cardiovascular issue, such as a lesion).

Computing device 150 may be associated with one or more clinicians, who may be located in the Cath lab during the medical procedure. Computing device 150 may include, for example, an off-the-shelf device, such as a laptop computer, desktop computer, tablet computer, smart phone, or other similar device. In other examples, computing device 150 may be a special purpose computing device, such as one specifically designed to be used in a Cath lab. Computing device 150 includes memory and processing circuitry.

In some examples, computing device 150 may be configured to control an electrosurgical generator, a peristaltic pump, a power supply, or any other accessories and peripheral devices relating to, or forming part of, system 100. In some examples, computing device 150 may perform various control functions with respect to imager 140, additional imager(s) 1042, display device 110, additional equipment 152, and/or the like. Computing device 150 may be communicatively coupled to device tracking system 121, imager 140, additional imager(s) 142, one or more devices of additional equipment 152, display device 110, server 160, and/or network 156.

While a number of features are described herein as being attributed to computing device 150, in some examples, features attributed to computing device 150 may be performed by processing circuitry of any of computing device 150, imager 140, server 160, network 156 (e.g., one or more computing devices forming or connected to network 156), other elements of system 100, or any combinations thereof. In some examples, processing circuitry associated with computing device 150 may be distributed and shared across any combination of computing device 150, imager 140, server 160, network 156, display device 110, and/or other elements of system 100. Additionally, in some examples, processing operations or other operations performed by processing circuitry of computing device 150 may be performed by processing circuitry residing remotely, such as one or more cloud servers or processors. For purposes of ease of discussion herein, such processing circuitry may be considered a part of computing device 150.

System 100 may include network 156, which is a suitable network such as a local area network (LAN) that includes a wired network or a wireless network, a wide area network (WAN), a wireless mobile network, a Bluetooth network, or the Internet. In some examples, network 156 may be a secure network, such as a hospital network, which may limit access by users. In some examples, network 156 may interconnect various devices of system 100.

As discussed above, imager 140 may be an angiography and/or fluoroscopy imager, and may image portions of a patient's body during or before a medical procedure to visualize characteristics and locations of lesions inside, for example a cardiac vasculature of the patient. Additional imager(s) 142 may also be configured to image portions of a patient's body, such as a cardiac vasculature of the patient. Additional imager(s) 142 may be devices other than angiography or fluoroscopy devices. For example, additional imager(s) may be any other type of imaging device, such as an ultrasound device, a CT device, an IVUS device, an OCT device, a NIRS device, an MRI device, a PET device, a dielectric-based imaging device, or the like. Additional imager(s) 142 may capture detail of the coronary vasculature of the patient that may not be captured by imager 140. For example, additional imager(s) 142 may capture more detail (e.g., morphology/type) of plaque structures or other lesion characteristics not captured by imager 140. The additional detail of plaque structures or other lesion characteristics may be utilized by computing device 150 to improve or update a 3D model of the coronary vasculature of the patient and/or to improve procedure modeling (including predicted effectiveness and/or predicted risks for a given medical procedure).

In some implementations, computing device 150 may be configured to capture data from one or more audio sensors (not shown) during the medical procedure, as is discussed later in this disclosure. Audio sensors may be off the shelf components of computing device 150, a laptop, tablet, mobile phone, or the like or may be a part of a Cath Lab.

In some examples, computing device 150 may be configured to obtain information from third-party screens (e.g., screens other than screens of computing device 150) for example by screen capture techniques (e.g., via a camera of computing device 150 or controlling the third-party screen to capture the information) or by receiving information from such third-party screens. In some examples, computing device 150 may be configured to obtain information from any devices of system 100 or devices not included in system 100. Such obtained information may be used in any of the determinations discussed herein.

Computing device 150 may be configured to execute one or more artificial intelligence (AI), machine learning (ML), and/or computer vision algorithms to generate or update a 3D model of the coronary vasculature of a patient, to generate procedural guidance, and/or to determine information to overlay on angiogram imaging data.

Computing device 150 may be configured to execute one or more computer vision algorithm(s) to determine devices of additional equipment 152 that may be used during a medical procedure. For example, computing device 150 may capture images of devices, packaging of devices, QR codes associated with the devices, bar codes associated with the devices, or the like. Computing device 150 executing the one or more computer vision algorithm(s) may determine the devices used and update an inventory of such devices (e.g., deduct the devices from a stored inventory log upon use of the devices).

Computing device 150 may be configured to execute one or more natural language processing algorithms to discern between clinically relevant and non-clinically relevant spoken words or phrases which may be captured during a medical procedure by, for example, one or more microphones of system 100 (e.g., of additional equipment 152).

Additional equipment 152 may include devices configured to be used during a medical procedure, such as a PCI procedure, including, but not limited to, stents, catheters, guide wires, angioplasty devices, ablation devices, atherectomy devices, intravascular lithotripsy (IVL) devices, energy generation devices, smart manifolds, device add-ons, or other such devices.

Display device 110 may be configured to display captured imaging data, from, for example, imager 140 and/or additional imager(s) 142. In some examples, display device 110 may be configured to display a 3D model of the coronary vasculature of a patient, instead of or in addition to captured imaging data. In some examples, display device 110 may be configured to display the various user interfaces disclosed herein. In some examples display device 110 may be configured to display procedural guidance as disclosed herein and/or information overlaid onto angiogram imaging data. Display device 110 may be configured to display any other content discussed as being displayed in this disclosure.

Table 120 may be, for example, an operating table or other table suitable for use during a medical procedure, such as a PCI procedure. Table 120 may include a device tracking system 121, such as a specially designed pad to be placed under, or integrated into, table 120.

Device tracking system 121 may include radio frequency identification (RFID), near field communication (NFC), battery powered sensors, triangulation technology, and/or an electromagnetic (EM) field generator which may be used to generate an EM field during the medical procedure. Such technologies may be used to track the positions of one or more devices within the body of a patient during a medical procedure. For example, device tracking system may track the location of devices (e.g., devices of additional equipment 152) by tracking sensors attached to or incorporated in such devices. In some examples, device tracking system 121 may serve as a charging pad which may wirelessly charge various sensors which may be placed on or in the patient, such as for monitoring patient parameters, during the medical procedure. Such sensors may wirelessly communicate with computing device 150. In this manner, fewer wires may be present in a Cath lab than otherwise may be, lowering a risk of entanglement with the patient or a clinician moving about the Cath lab. In some examples, wired sensors (e.g., of additional equipment 152) may be utilized which may be, via the wires of the wired sensors, connected to or disconnected from one or more devices of system 100, such as computing device 150.

Server 160 may be configured to store data obtained by and/or determined or generated by computing device 150. In some examples, server 160 may be configured to perform techniques attributed to computing device 150. Server 160 may be communicatively coupled to computing device 150, for example, by wired, optical, or wireless communications and/or by network 156. Server 160 may be a hospital server which may or may not be located in a Cath lab, such as a cloud-based server, or the like. Server 160 may be configured to store patient data, electronic patient records, or the like.

In some examples, system 100 may include an automated contrast delivery device (e.g., of additional equipment 152). In such examples, system 100 may monitor an amount of contrast provided to the patient by the automated contrast delivery device or otherwise provided to the patient. Computing device 150, based on the amount of contrast provided to the patient and a first amount of contrast needed or recommended for obtaining further desired imaging data, control the automated contrast delivery device to deliver a second amount of contrast.

Figure 2:
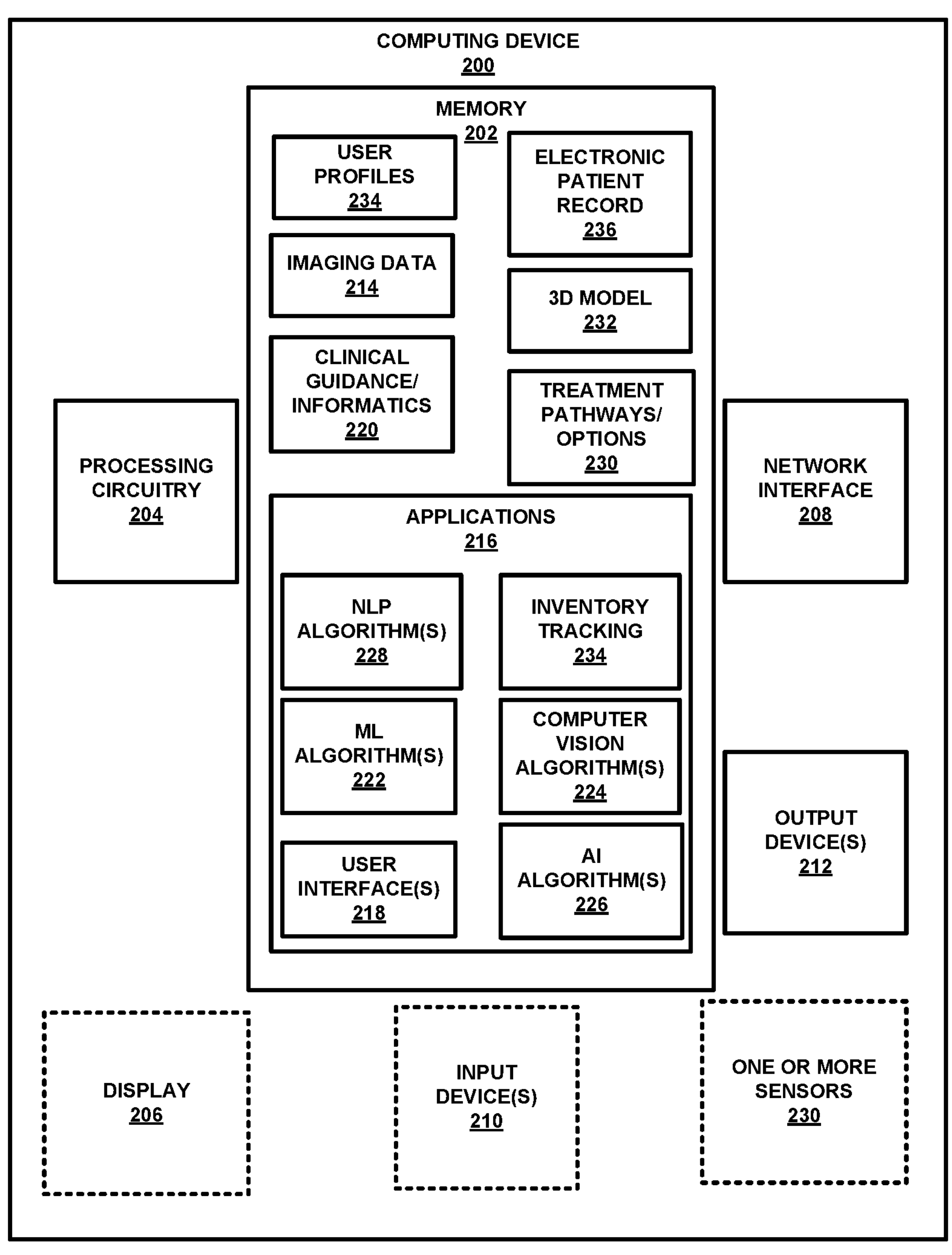
FIG. 2 is a block diagram of an example of a computing device in accordance with one or more aspects of this disclosure.

FIG. 2 is a block diagram of an example of a computing device in accordance with one or more aspects of this disclosure. Computing device 200 may be an example of computing device 150, a computing device of network 156, and/or server 160 of FIG. 1 and may include a workstation, a desktop computer, a laptop computer, a server, a smart phone, a tablet, a dedicated computing device, or any other computing device capable of performing the techniques of this disclosure.

In some examples, computing device 200 may be configured to perform processing, control and other functions associated with various devices of FIG. 1, such as display device 110, imager 140, additional imager(s) 142, additional equipment 152, and/or device tracking system 121. Computing device 200 may include, for example, a memory 202, processing circuitry 204, a display 206, a network interface 208, an input device(s) 210, or an output device(s) 212, each of which may represent any of multiple instances of such a device within the computing system, for ease of description.

While processing circuitry 204 appears in computing device 200 in FIG. 2, in some examples, features attributed to processing circuitry 204 may be performed by processing circuitry of any of computing device 150, imager 140, server 160, computing devices of network 156, or other components of FIG. 1. In some examples, one or more processors associated with processing circuitry 204 in computing device 200 may be distributed and shared across any combination of computing device 150, imager 140, server 160, computing devices of network 156, or other components of FIG. 1. Additionally, in some examples, processing operations or other operations performed by processing circuitry 204 may be performed by one or more processors residing remotely, such as one or more cloud servers or processors, each of which may be considered a part of computing device 200. Computing device 200 may be used to perform any of the techniques described in this disclosure, and may form all or part of devices or systems configured to perform such techniques, alone or in conjunction with other components, such as components of computing device 150, imager 140, server 160, computing devices of network 156, other components of FIG. 1, or a system including any or all of such devices.

Memory 202 of computing device 200 includes any non-transitory computer-readable storage media for storing data or software that is executable by processing circuitry 204 and that controls the operation of computing device 150. In one or more examples, memory 202 may include one or more solid-state storage devices such as flash memory chips. In one or more examples, memory 202 may include one or more mass storage devices connected to the processing circuitry 204 through a mass storage controller (not shown) and a communications bus (not shown).

Although the description of computer-readable media herein refers to a solid-state storage, it should be appreciated by those skilled in the art that computer-readable storage media may be any available media that may be accessed by the processing circuitry 204. That is, computer readable storage media includes non-transitory, volatile and non-volatile, removable and non-removable media implemented in any method or technology for storage of information such as computer-readable instructions, data structures, program modules, or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium that may be used to store the desired information and that may be accessed by computing device 200. In one or more examples, computer-readable storage media may be stored in the cloud or remote storage and accessed using any suitable technique or techniques through at least one of a wired or wireless connection.

Memory 202 may store NLP algorithm(s) 228, ML algorithm(s) 222, AI algorithm(s) 226, computer vision algorithm(s) 224, inventory tracking algorithm(s) 234, and/or user interface(s) 218. In some examples, any of ML algorithm(s) 222, AI algorithm(s) 226, computer vision algorithm(s) 224, and/or NLP algorithm(s) 228 may be the same. In some examples, any of ML algorithm(s) 222, AI algorithm(s) 226, computer vision algorithm(s) 224, and/or NLP algorithm(s) 228 may be the different.

Memory 202 may also store user interface(s) 218 and/or inventory tracking algorithm(s) 234. User interface(s) 218 may include one or more user interfaces which processing circuitry 204 may output for display by display 206 and/or display device 110. Inventory tracking algorithm(s) 234 may be used to track inventory of devices used during a medical procedure. For example, a clinician may scan a QR code or a bar code of a device using input device(s) 210 and processing circuitry 204 executing inventory tracking algorithm(s) 234 may update inventory of such devices. In some examples, processing circuitry 204 may execute computer vision algorithm(s) 224 to determine which devices are being used during the procedure and update inventory tracking algorithm(s) 234 (or an inventory otherwise in memory 202) to track inventory, for example, of additional equipment 152.

Memory 202 may store imaging data 214, clinical guidance/informatics 220, electronic patient record 236, 3D model 232, user profiles 234, and/or treatment pathways/options 230. Imaging data 214 may be captured by imager 140 and/or additional imager(s) 142 (FIG. 1) during a medical procedure of a patient. Processing circuitry 204 may obtain imaging data 214 from imager 140 and/or additional imager(s) 142 and store imaging data 214 in memory 202. Processing circuitry 204 may use imaging data 214 to determine 3D model and/or update 3D model 232. For example, processing circuitry 204 may determine 3D model 232 using imaging data 214 from imager 140 and update 3D model 232 using imaging data 214 from additional imager(s) 142 or both imager 140 and additional imager(s) 142. Processing circuitry 204 may also use imaging data 214 to determine clinical guidance/informatics 220, treatment pathways/options 230, and/or the like. Processing circuitry 204 may use information obtained during a medical procedure to automatically update electronic patient record 236 such that a clinician does not need to enter all pertinent information into electronic patient record 236 manually. In some examples, electronic patient record 236 may include a post procedure report including information relating to a medical procedure. In some examples, electronic patient record 236 may include patient metadata, such as demographic information like patient age, weight, height, or the like, health records, previously implanted medical devices, and/or the like. User profiles 234 may store user preferences specific to a given clinician as discussed later herein.

Any or all of ML algorithm(s) 222, computer vision algorithm 224, and/or AI algorithm(s) 226, may be trained using data collected from past medical procedures, such as imaging data, device data (e.g., including device parameters such as device size, length, device settings, etc.), procedure outcomes, patient outcomes, or the like. Device settings may include time used, pressure used, or the like. For example, ML algorithm(s) 222, computer vision algorithm 224, and/or AI algorithm(s) 226, may be trained on data from actual procedures, reflecting actual treatments and actual outcomes from past medical procedures. Such algorithms may be utilized to determine 3D model 232, clinical guidance/informatics 220, and/or treatment pathways/options 230.

For example, ML algorithm(s) 222 may include a k-means clustering model which may have a plurality of clusters: one for each particular treatment technique (e.g., treatment pathway or treatment option) using one or more particular devices. Each identified lesion may be associated with a vector that includes variables for, e.g., type of coronary issue, severity of the coronary issue, complexity of the coronary issue, location of the coronary issue, classification of a lesion, anatomy in the area of the coronary issue, other anatomy, comorbidities of the patient, cholesterol level, blood pressure, blood oxygenation, age, physical exercise level, and/or the like. The location of the vector in a given one of the clusters may be indicative of a particular treatment using one or more particular devices. For example, if the vector falls within the cluster for angioplasty using a particular device, machine learning model(s) 222 may include angioplasty as a treatment pathway and angioplasty with the particular device as a treatment option which processing circuitry 204 may store in treatment pathways/options 230.

Alternatively, the k-means clustering algorithm may have a plurality of clusters, one for each type of lesion. Each treatment strategy may be associated with a vector that includes variables for, e.g., type of coronary issue, severity of the coronary issue, complexity of the coronary issue, location of the coronary issue, anatomy in the area of the coronary issue, other anatomy, comorbidities of the patient, cholesterol level, blood pressure, blood oxygenation, age, physical exercise level, and/or the like.

Other potential machine learning or artificial intelligence techniques that may be used include Naïve Bayes, k-nearest neighbors, random forest, support vector machines, neural networks, linear regression, logistic regression, classification models, anomaly detection, Convolutional neural networks (CNNs), object detection, natural language processing (NLP), facial recognition, Recommender systems, optical character recognition (OCR) to read text & characters from other systems and/or screens, or any other similar techniques. Such models may be train using batch gradient descent, stochastic gradient descent, mini-batch gradient descent, or any other similar techniques.

Processing circuitry 204 may execute any of user interface(s) 218 so as to cause display 206 (and/or display device 110 of FIG. 1) to present that UI of user interface(s) 218 to one or more clinicians performing the therapeutic medical procedure. Several example UIs are presented later in this disclosure.

Processing circuitry 204 may be implemented by one or more processors, which may include any number of fixed-function circuits, programmable circuits, or a combination thereof. In various examples, control of any function by processing circuitry 204 may be implemented directly or in conjunction with any suitable electronic circuitry appropriate for the specified function. Fixed-function circuits refer to circuits that provide particular functionality and are preset on the operations that may be performed. Programmable circuits refer to circuits that may programmed to perform various tasks and provide flexible functionality in the operations that may be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits.

Instructions may be executed by one or more processors, such as one or more digital signal processors (DSPs), general purpose microprocessors, application specific integrated circuits (ASICs), field programmable gate arrays (FPGAs), graphics processing units (GPUs) or other equivalent integrated or discrete logic circuitry. Accordingly, the term processing circuitry 204 as used herein may refer to one or more processors having any of the foregoing processor or processing structure or any other structure suitable for implementation of the techniques described herein. In addition, in some aspects, the functionality described herein may be provided within dedicated hardware or software modules configured for encoding and decoding, or incorporated in a combined codec. Also, the techniques could be fully implemented in one or more circuits or logic elements.

Display 206 may be touch sensitive or voice activated, enabling display 206 to serve as both an input and output device. Alternatively, a keyboard (not shown), mouse (not shown), joystick (not shown) or other data input device(s)s (e.g., input device(s) 210) may be employed. In some examples, display 206 may include a virtual reality and/or augmented reality headset. In some examples, display 206 may include a hologram device.

Network interface 208 may be adapted to connect to a network (e.g., network 156) such as a local area network (LAN) that includes a wired network or a wireless network, a wide area network (WAN), a wireless mobile network, a Bluetooth network, or the internet. In some examples, network interface 208 may include one or more application programming interfaces (APIs) for facilitating communication with other devices. For example, computing device 200 may receive imaging data 214 from imager 140 and/or additional imager(s) 142 during a medical procedure via network interface 208. Computing device 200 may interact with server 160 via network interface 208. Computing device 200 may receive updates to its software, for example, applications 216, via network interface 208. Computing device 200 may also display notifications on display 206 that a software update is available.

Input device(s) 210 may include any device that enables a user to interact with computing device 200, such as, for example, a mouse, joystick, keyboard, foot pedal, touch screen, augmented-reality input device(s) receiving inputs such as hand gestures or body movements, or voice interface.

Output device(s) 212 may include any connectivity port or bus, such as, for example, parallel ports, serial ports, universal serial busses (USB), or any other similar connectivity port known to those skilled in the art.

Applications 216 may include one or more software programs stored in memory 202 and executed by processing circuitry 204 of computing device 200.

In some examples, processing circuitry 204 may provide real-time clinical guidance to a clinician. For example, processing circuitry 204 may use or execute computer vision algorithm(s) 224 to determine characteristics of a lesion and/or determine a location of a lesion and execute ML algorithm(s) 222 and/or AI algorithm(s) 226 to provide the clinician with proposed treatment strategies (e.g., clinical guidance/informatics 220 and/or treatment pathways/options 230).

Figure 3:
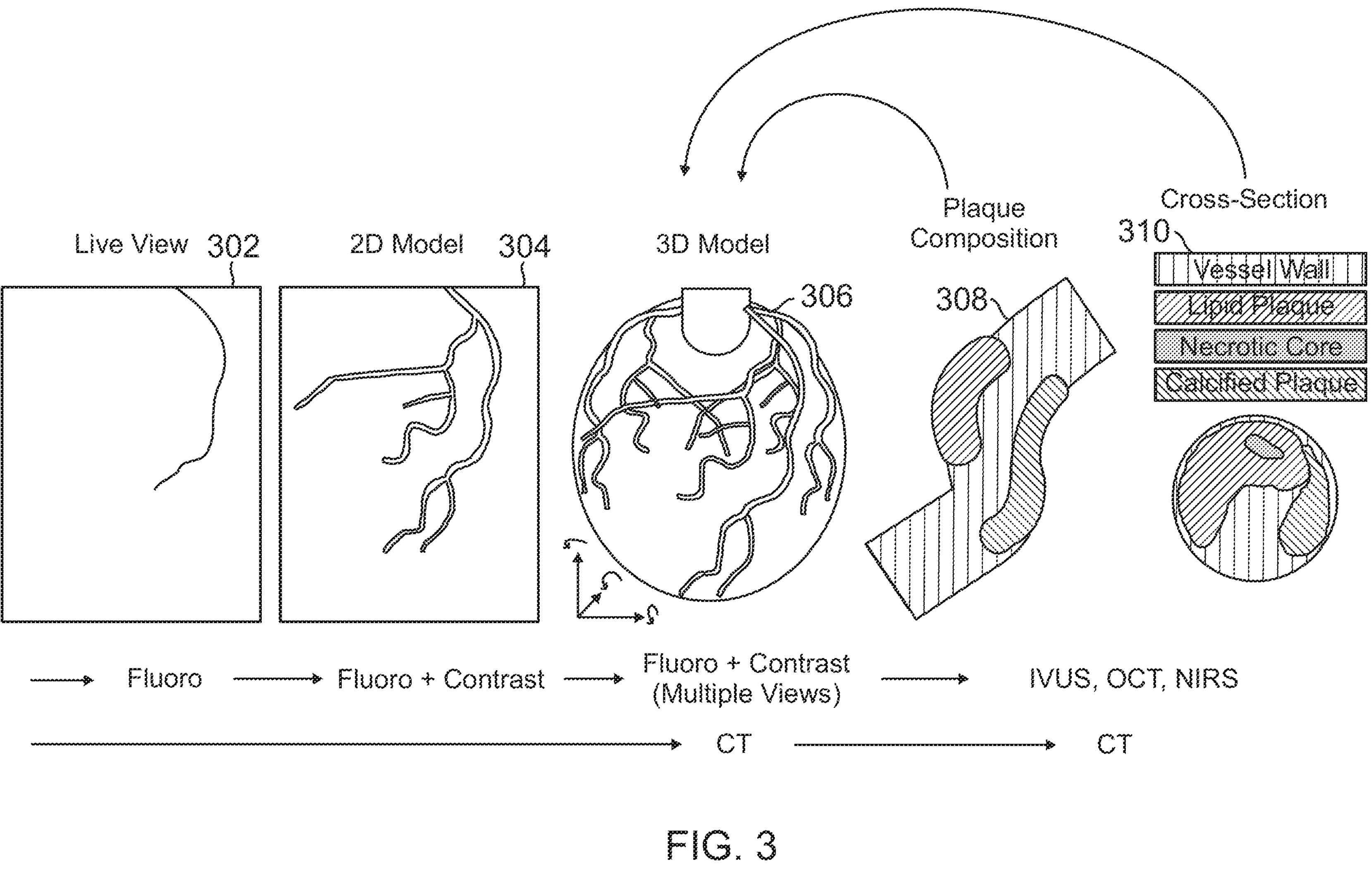
FIG. 3 is a conceptual diagram illustrating example elements of the construction of a 3D model of cardiac vasculature of a patient and updates to the 3D model according to one or more aspects of this disclosure.

FIG. 3 is a conceptual diagram illustrating example elements of the construction of a 3D model of cardiac vasculature of a patient and updates to the 3D model according to one or more aspects of this disclosure. Certain aspects of the example of FIG. 3 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

Imager 140 may capture a live fluoroscopy view of the cardiac vasculature of a patient. A clinician or system 100 may inject contrast into the patient (e.g., into a selected portion of vasculature of a patient) which may improve contrast of the captured fluoroscopy imaging data. In some examples, this captured fluoroscopy with contrast imaging data may be viewed as 2D model 304 of the cardiac vasculature of the patient as the fluoroscopy with contrast imaging data may be displayed on a 2D display device, for example, in a Cath lab.

In some examples, imager 140 may include a plurality of imaging sensors which may be oriented to a patient at different angles. As such, processing circuitry 204 may employ epipolar geometry (e.g., stereo vision) to determine 3D model 306 of the cardiac vasculature of the patient based on fluoroscopy imaging data captured by imager 140 from imaging sensors positioned to face the patient at different angles. If imager 140 does not include a plurality of imaging sensors placed at different angles, processing circuitry 204 may prompt a clinician, e.g., via output device(s) 212 or display 206 to reposition imager 140 to capture fluoroscopy with contrast imaging data at a different angle and processing circuitry 204 may determine 3D model 306 based on the fluoroscopy with contrast imaging data captured at the two (or more, e.g., three) different angles. Alternatively, processing circuitry 204 may automatically control imager 140 to capture fluoroscopy with contrast imaging data at a different angle and processing circuitry 204 may determine 3D model 306 based on the fluoroscopy with contrast imaging data captured at the two (or more, e.g., three) different angles. For example, by using two different viewing angles (either from a same imaging sensor at different times, or from two different imaging sensors having different viewing angles) processing circuitry 204 may determine a 3D view of the coronary vasculature of a patient, similarly to the way a human may perceive an object in 3D based on two eyes each viewing an object from different viewing angles. Processing circuitry 204 determined 3D model 306 may be more accurate than any mental 3D model a clinician may think of from 2D model 304. For example, a human mind is not be capable of determining 3D model 306, as there are inherent properties (e.g., vessels traveling at angles from a 2D plane of 2D model 304) which a human mind will not perceive from 2D model 304. Even if a human were to try to generate a mental 3D image based on fluoroscopy with contrast images taken from more than one viewing angle, the vast number of differences between each of the images would not be translatable into a mental 3D image by a human mind.

For example, processing circuitry 204 may generate 3D model 306 of the coronary vasculature of a patient from captured fluoroscopy imaging data. Additionally, or alternatively, processing circuitry 204 may generate 3D model 306 based on other imaging data captured from additional imager(s) 142, based on information from additional equipment 152, electronic patient record 236, and/or information entered by a clinician, such as patient metadata, including demographic information like patient age, weight, height, or the like, health records, previously implanted medical devices, and/or the like. Processing circuitry 204 may update 3D model 306 from time to time, periodically, or continuously throughout the procedure as more information is collected. In some examples, processing circuitry 204 may perform 3D coordinate averaging, interpolation, or other techniques to generate a more accurate 3D model 306.

In some examples, processing circuitry 204 may generate 3D model 306 from sequential frames of captured imaging data 214, such as sequential frames of video data. In this manner 3D model 306 may include a model of the anatomy state of patient anatomy in the systolic phase, the diastolic phases, as well as a spectrum of dimensions throughout the full cardiac cycle between these phases.

In some examples, 3D model 306 may include anatomical dimension information. In such examples, processing circuitry 204 may be configured to control display 206 to display anatomical dimension information of 3D model 306 with or without displaying 3D model 306. In some examples, a clinician may input a query to computing device 150 and processing circuitry 204, may, in response to query, control display 206 to display anatomical dimension information of 3D model 306. Anatomical dimension information may include an indication of one or more dimensions of anatomy represented by 3D model 306.

In some examples, processing circuitry 204 may use a checklist approach to improve 3D model 306 quality. For example, processing circuitry 204 may maintain a checklist of data and/or data sources with which processing circuitry 204 may enhance or improve 3D model 306. If processing circuitry 204 has not received such data or data from such data sources, processing circuitry 204 may suggest, to a clinician via output device(s) 212 and/or display 206, additional sources of information to improve the quality of 3D model 306. For example, if system 100 has not captured other imaging data, processing circuitry 204 may suggest to the clinician to capture other imaging data, for example, from one or more of other imager(s) 142. In other examples, processing circuitry 204 may automatically control one or more of other imager(s) 142 to capture other imaging data.

For example, processing circuitry 204 may determine initial 2D model 302 based on fluoroscopy imaging with a single contrast injection to the patient. Processing circuitry 204 may suggest a second (and/or third) view with contrast to the clinician to be captured by imager 140 (or may automatically control imager 140 to capture the second view), which processing circuitry 204 may use to generate 3D model 306. If the clinician desires the 3D image, the clinician may follow the suggested course of action and processing circuitry 204 may determine or generate 3D model 306 based on the first fluoroscopy with contrast imaging data and the imaging data resulting from the suggested course of action (e.g., the second and/or third fluoroscopy with contrast imaging data). As mentioned above, if imager 140 includes a plurality of imaging sensors at different angles with respect to the patient, computing device may determine or generate 3D model 306 without having to suggest that the clinician make an adjustment to the angle of imager 140 capturing the fluoroscopy with contrast imaging data.

In other examples, rather than creating 3D model 306 from fluoroscopy with contrast imaging data, processing circuitry 204 may create 3D model 306 using other imaging data (e.g., CT imaging data, MRI imaging data, or the like), or may receive a 3D model 306 from another computing device or retrieve 3D model 306 from a data source.

Processing circuitry 204 may output for display 3D model 306 for viewing by the clinician. For example, processing circuitry 204 may control display 206 to display 3D model 306. In some examples, display 206 represents a 2D screen which may display 3D model 306. In such examples, the clinician may manipulate 3D model 306 on display 206 to view 3D model 306 from different viewpoints and/or forwards and backwards in time through an input device of input device(s) 210, such as a mouse or joystick. In some examples, display 206 represents a virtual reality or augmented reality headset configured to display 3D model 306 for viewing by the clinician. In some examples, display 206 may represent a hologram device and model 306 may be displayed as a hologram. 3D model 306 may be based on more than one imaging source or more than one imaging angle, thereby providing a more accurate 3D model of the coronary vasculature of the patient than a mental model which may be thought of by the clinician based on one or more 2D images or 2D model 304.

In some examples, if other imaging data already exists (e.g., from an earlier diagnostic procedure), such as computed tomography (CT) data, computing device 150 may update 3D model 306 based on the other imaging data.

The displayed 3D model 306 may provide the clinician with a map showing a geometry of the coronary vasculature of the patient, including an inner diameter of a blood flow path. However, when such a 3D model is based solely upon fluoroscopy with contrast imaging data, the 3D model may not include lesion dimensions, such as thickness, orientation with respect to the vessel walls, composition, or the like.

A clinician may conduct IVUS, OCT, near infrared spectroscopy (NIRS), or the like, on their own, or as suggested by processing circuitry 204, to provide additional information to processing circuitry 204. For examples, other imager(s) 142 may capture IVUS imaging data, OCT imaging data, NIRS imaging data, or other imaging data. Additionally, or alternatively, processing circuitry 204 may retrieve other imaging data, e.g., from a previous imaging session the patient has undergone. The other imaging data may include, for example, CT imaging data, MRI imaging data, or the like. Processing circuitry 204 may utilize such additional imaging data from other imager(s) 142 to enhance the 3D model to include information such as lesion dimensions, orientation with respect to the vessel walls, lesion composition (e.g., lipid, fibrous, calcific, etc.), or the like. For example, processing circuitry 204 may obtain additional imaging data, including imaging data other than fluoroscopy with contrast imaging data and update 3D model 306 based on the additional imaging data. For example, processing circuitry 204 may obtain CT imaging data, IVUS imaging data, OCT imaging data, or NIRS imaging data which processing circuitry 204 may use to update 3D model 306 to include such enhancements as plaque composition 308 and/or cross-section 310 (e.g., the updating of 3D model 306 is represented by the arrows in FIG. 3). Such an updated 3D model (e.g., 3D model 306) updated to include plague composition 308 and cross-section 301, may be much more complex than 3D model 306 prior to such enhancements and is not capable of being determined by or held in a human mind.

At any stage during the generation, updating, or maintaining of 3D model 306 (e.g., prior to the addition of the additional imaging data, during the addition of the additional imaging data, or after the addition of the additional imaging data), processing circuitry 204 may model procedures to generate procedural guidance for a clinician. As part of modeling such procedures, processing circuitry 204 may determine a plurality of predictive treatment pathways based on 3D model 306. In some examples, processing circuitry 204 may automatically determine predictive treatment pathways from time to time, periodically, or continuously. In some examples, processing circuitry 204 may determine predictive treatment pathways based on clinician input, such as a request to determine predictive treatment pathways via input device(s) 210. Such predictive treatment pathways may be used by a clinician to make better informed decisions about how to treat a given lesion or other cardiovascular issue, thereby improving patient outcomes.

Processing circuitry 204 may provide, e.g., via display 206, determined predictive treatment pathways. For example, in response to physician input, processing circuitry 204 may display predictive treatment pathways, which is discussed in more detail later in this disclosure.

As part of generating or updating 3D model 306, processing circuitry 204 may determine vessel physiology, vessel morphology, vessel dimensions, lesion physiology, lesion morphology, lesion dimensions, implanted devices, such as stents, devices currently in use, such as specific or generalized catheter devices a clinician is controlling, and/or the like. In some examples, computing device 150 may use Digital Imaging and Communications in Medicine (DICOM) files and/or captured imaging data to determine vessel physiology, morphology, vessel dimension morphology and/or physiology of atherosclerotic lesions, implanted devices, such as stents, devices currently in use, such as specific or generalized catheter devices a clinician is controlling, and/or the like. Where DICOM files are not available, computing device 150 may perform calibration(s) of the captured imaging data based on known device measurement references.

In some examples, processing circuitry 204 may overlay imaging data onto other imaging data and/or 3D model 306, or overlay a treatment option onto imaging data and/or 3D model 306. In some examples, processing circuitry 204 may co-register imaging data with other imaging data and/or 3D model 306. For example, processing circuitry 204 may execute computer vision algorithm(s) 224 to determine common reference structures in the imaging data and/or the 3D model and anchor the common reference structures together as part of co-registering imaging data and/or 3D model 306.

In some examples, processing circuitry may execute computer vision algorithm(s) 224 to determine common reference structures in additional imaging data from imaging devices other than fluoroscopy imaging devices and the 3D model and anchor the common reference structures together to co-registering the additional imaging data and 3D model 306. Processing circuitry 204 may then update the 3D model based on additional information contained in the co-registered additional imaging data.

In some examples, processing circuitry 204 may identify one or more potential high-risk areas within the imaging data which may need additional morphology data and/or geometry data before treatment. For example, processing circuitry 204 may execute one or more of ML algorithm(s) 222, AI algorithm(s) 226, and/or computer vision algorithm(s) 224 to identify such potential high-risk areas. In such examples, processing circuitry 204 may suggest to the clinician that the clinician acquire additional information which may be used by processing circuitry 204 to determine the additional morphology data. In some examples, processing circuitry 204 may automatically control additional imager(s) 142 and/or additional equipment 152 to acquire such additional information.

For example, processing circuitry 204 may process obtained imaging information and may employ one or more AI algorithm(s) 226, ML algorithm(s) 222 and/or computer vision algorithm(s) 224. For example, processing circuitry 204 may receive CT imaging data (e.g., from other imager(s) 142) and fluoroscopy with contrast imaging data and/or angiogram imaging data (e.g., from imager 140) and process such imaging data using one or more AI algorithm(s) 226, ML algorithm(s) 222, and/or computer vision algorithm(s) 224. In some examples, processing circuitry 204 may obtain fluoroscopy with contrast imaging data or angiogram imaging data, obtain additional imaging data, such as CT imaging data IVUS, OCT imaging data, and/or NIRS imaging data, and receive or compute FFR values based on obtained imaging data, and process such imaging data using one or more AI algorithm(s) 226, ML algorithm(s) 222, and/or computer vision algorithm(s) 224. AI algorithm(s) 226 and/or ML algorithm(s) 222 may include multi-body dynamics, finite element analysis (FEA), an optimized physics engine, reinforcement learning AI, graphics engine image processing, gesture/voice control virtual model manipulation, or the like.

In some examples, processing circuitry 204 may also determine or generate 3D, scaled models of devices which may be used during the procedure (e.g., of additional equipment 152), including geometry and, optionally, key defining characteristics of such devices (e.g., catheter flexibility, conformity to the anatomy, size, etc.).

In some examples, imager 140 may, after 3D model 306 is initially generated, provide processing circuitry 204 with relatively low frame rate updates of imaging data. For processing circuitry 204 may control imager 140 to, rather than capture fluoroscopy with contrast imaging data at 15 frames/second, capture fluoroscopy with contrast imaging data at less than 15 frames/second, such as less than 1 frame/second, 1 frame/second, 2 frames/second, or the like. Such updates may be used to update 3D model 306 and/or to track movement of device(s) in the vasculature of the patient. For example, processing circuitry 204 may execute computer vision algorithm(s) 224 to analyze obtained lower frame rate fluoroscopy with contrast imaging data. By utilizing fluoroscopy with contrast imaging data at a lower frame rate, and processing such imaging data with computer vision algorithm(s) 224, fluoroscopy with contrast imaging data may be of relatively high quality despite being captured at a lower frame rate and imager 140 may require less contrast to produce such imaging data, thereby reducing an amount of radiation to which the patient (and the clinician) may be exposed.

Processing circuitry 204 may create a 3D virtual model of the coronary vasculature system of a patient with which a clinician may interact with to gain additional information (e.g., vessel morphology, physiology, measurement, etc.) to allow more informed planning and to facilitate the administration of better care. Processing circuitry 204 may create different virtual treatment options and predict outcomes (e.g., effectiveness) and/or risks for each such virtual treatment options, allowing a clinician to select a treatment option which the clinician may believe provides an optimal result.

These 3D modeling techniques may provide clinicians with more accurate information and additional information not available in a mental 3D model, such as vessel morphology, lesion location, lesion morphology (e.g., type), lesion size, vessel length, vessel diameter, fractional flow reserve (FFR) scores, SYNTAX score, or the like, which may facilitate the clinician to make more informed treatment decisions while planning how to treat or treating a patient.

Processing circuitry 204 may execute ML algorithm(s) 222, AI algorithm(s) 226, and/or computer vision algorithm(s) 224 to model virtual procedures. For example, computing device 150 may execute ML algorithm(s) 222, AI algorithm(s) 226, and/or computer vision algorithm(s) 224 determine probabilistic statistics, estimates of characteristics of one or more lesions, and provide such statistics and estimates to a clinician via display 206. For example, ML algorithm(s) 222, AI algorithm(s) 226, and/or computer vision algorithm(s) 224 may be trained on previous imaging data and/or data from previous procedures. Such probabilistic statistics and estimates may be based on similar anatomy from the training data. Processing circuitry 204 may also inform the clinician of areas of uncertainty and provide suggestions to the clinician to collect more data to address any areas of uncertainty. For example, processing circuitry 204 may determine that certain data is missing from the data collected for the current patient and that a data set from a previous patient included such data. To improve the accuracy of the probabilistic statistics and estimates, processing circuitry 204 may output for display a suggestion that the clinician collect X data in Y region, for example, via output device(s) 212 and/or display 206. Alternatively, processing circuitry 204 may automatically control additional imager(s) 142 and/or additional equipment 152 to collect X data in Y region.

In general, more data may improve model certainty upon which processing circuitry 204 may determine treatment procedure suggestions. In some examples, processing circuitry 204 may determine a level of confidence for each suggested treatment procedure and output, via output device(s) 212 and/or display 206, an indication of the determined levels of confidence. A level of confidence may be a measure of certainty which processing circuitry 204 has in predicted risks and/or outcomes associated with a given treatment procedure suggestion.

Processing circuitry 204 may output for display a range of treatment pathways, probabilities of outcomes (which may be based on a graphically modelled prediction and/or reflect predicted effectiveness), risks associated with each treatment pathway (e.g., stenting at high pressure will fully relieve flow, but incur a 0.5% risk of an embolic particle during the procedure, while ballooning at moderate pressure will mildly relive flow, but incur a 0.01% chance of an embolic particle), and confidence levels associated with each treatment pathway and/or each prediction. For example, computing device may output for display angioplasty over X region, stent over Y region, and/or atherectomy over Z region.

Processing circuitry 204 may determine and output for display preferred devices for use during a suggested procedure and preferred device parameters (including device settings), such as use a 3 mm non-compliant (NC) balloon and inflate the NC balloon to 3.14 bar. Processing circuitry 204 may predict the flow after the lesion is opened (e.g., using a balloon, stent, atherectomy, etc.) and the effects of such an opening of the lesion on other blood vessels.

In some examples, processing circuitry 204 may utilize data from electronic healthcare records (EHR) to link pre-procedure history, medications, patient metadata, etc., to patient outcomes. Such data may be used to train ML algorithm(s) 222, AI algorithm(s) 226, and/or computer vision algorithm(s) 224, thereby providing for continuous improvement of the predictions and suggestions generated by executing such algorithms.

For example, processing circuitry 204 may determine performance predictions based on the 3D model and AI, ML, and/or computer vision, matching previous similar scenarios and analyzing outcomes (e.g., effectiveness) when performed in a specified manner. Processing circuitry 204 may determine performance predictions based on computational simulations, using one or more of ML algorithm(s) 222, AI algorithm(s) 226, and/or computer vision algorithm(s) 224, such as an FEA, multi-body dynamics, custom algorithms, or the like. In some implementations, processing circuitry 204 may use 3D model 306 in combination with computational simulations, using one or more of ML algorithm(s) 222, AI algorithm(s) 226, and/or computer vision algorithm(s) 224, such as am FEA, multi-body dynamics, custom algorithms, or the like. In some examples, processing circuitry 204 may run a plurality of combinations of scenarios to determine a best predicted outcome. In examples where there is insufficient training data to provide a performance prediction at a specific confidence level, processing circuitry 204 may provide a generally wide confidence interval on predictions, for example 20%-80%, rather than a specific confidence level, such as 56%.

FIG. 4 is a conceptual diagram illustrating an example page of a user interface (UI) according to one or more aspects of this disclosure. Certain aspects of the example of FIG. 4 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

For example, processing circuitry 204 may control display 206 to display a UI, such as page 400. Page 400 may be one page of a UI for clinical guidance, such as a treatment prediction panel and may represent a UI of user interface(s) 218 (FIG. 2). Page 400 may display a plurality of treatment pathways 404, such as medication, angioplasty, stent, atherectomy and stent, coronary artery bypass graft (CABG), or the like. Such displays may be textual, graphical, combinations of textual and graphical (as shown), or the like.

Page 400 may include table 402 which may display various information relating to plurality of treatment pathways 404. In the example shown in FIG. 4, the information is textual. In some examples, the information may be displayed in forms other than tabular. For example, table 402 may include a row indicating a recommendation rating. A recommendation rating may be displayed for each of plurality of treatment pathways 404. In the example of FIG. 4, the recommendation ratings are relative to each other such that the total of all the recommendation ratings equals 100%. In some examples, processing circuitry 204 may control display 206 to only display recommendation ratings meeting a ratings threshold. For example, recommendation ratings not meeting the ratings threshold (e.g., a programmable threshold, such as 10%) would not be displayed. Processing circuitry 204 may determine the recommendation ratings for each of plurality of treatment pathways 404 based on information such as any of, or any combination of, predicted effectiveness of the treatment, predicted risk of the treatment, predicted time to perform the treatment, inventory, and/or mechanical circulatory support (MCS) recommendation. An MCS recommendation may be an indication of how strongly processing circuitry 204 may recommends using an MCS device to provide mechanical support for blood flow during (or potentially for a period before/after) the associated procedure. For example, processing circuitry 204 may determine a relatively high MCS recommendation for scenarios with a high risk of ischemia (e.g., blood flow restriction) for a sustained period of time or potentially for patients who are identified as being immediately ischemic. In some examples, an MCS recommendation checkbox, such as MCS recommendation checkbox 406, may provide a clinician with an option to select (e.g., check off) if the clinician desires to view predicted outcomes/risks based on whether or not MCS is used. For example, when a clinician clicks MCS recommendation checkbox 406, processing circuitry 204 may control display 206 to display a view of predicted outcomes/risks determined by processing circuitry 204 based on whether or not MCS is used for, for example, the CABG procedure.

Table 402 may also include effectiveness predictions. For example, processing circuitry 204 may predict one or more effectiveness ratings of each of the plurality of treatment pathways. In the example of FIG. 4, table 402 includes a plurality of effectiveness predictions for each of the plurality of treatment pathways. For example, table 402 includes a predicted FFR value (or range) which may exist for the vessel after treatment. For example, the predicted FFR value for medication is indicated as 0.67, which is the lowest FFR value in table 402, indicating that the other treatment pathways are predicted as yielding better FFR values. Table 402 also includes quality of life (QOL) improvements predictions. While the examples provided in table 402 for the QOL improvement predictions are based on a generic scale, the scale used for a QOL improvement may include any of a generic QOL scale, a custom-designed QOL scale, a Short-Form Health Survey (SF-36) scale (which accounts for factors such as physical functioning, pain, vitality, etc., on a scale of 0-100), or the like. In some examples, the QOL improvement predictions may include separate predictions for individual factors, an overall average score, and/or most relevant of factors for the given patient or procedure. In some examples, table 402 may include a link or icon which may allow a clinician to select an QOL improvement prediction, such as an overall average score, to access a more detailed breakdown of the QOL improvement factors. For example, if a clinician clicks on or selects a QOL improvement prediction, such as an overall average score, processing circuitry 204 may control display 206 to display a more detailed breakdown of the QOL improvement factors and predictions associated therewith.

For example, the predicted QOL improvements for medication is indicated as +1, which is the lowest QOL improvements value in table 402, indicating that the other treatment pathways are predicted as yielding better QOL improvements. Table 402 also includes readmission rates predictions, at both 1 month and 3 months out from the procedure. Again, the predicted readmission rates for medication, at 8% for 1 month and 15% for 3 months are the worst among the plurality of treatment pathways. Combined, this suggests that medication is a less effective treatment pathway compared to angioplasty, stent, atherectomy and stent, or CABG.

Table 402 also includes risk predictions. For example, processing circuitry 204 may predict risks associated with each of the plurality of treatment pathways. In table 402, the risks displayed include predicted risks of complications (embolism) and predicted days in bed after the procedure. For example, the predicted risk of embolism for medication is 0.1%±0.2% which is the lowest risk of embolism of the plurality of treatment pathways. The predicted number of days in bed for medicine is 0, which is also the lowest among the plurality of treatment pathways. Thus, table 402 indicates that medicine is a relatively ineffective procedure for the patient, but with relatively low risk.

Table 402 also includes predictions of time to complete each of the plurality of treatment pathways. For example, the prediction to complete medication is 5 minutes, which is the least amount of time of the time predictions for the plurality of treatment pathways.

Table 402 also includes an inventory section. The inventory section may include an on-hand inventory of device(s) needed or likely to be used for the procedure. For example, there may be 200 of the doses or other units of medication that may be used in the medication treatment pathway available to the Cath lab where the procedure is performed. In some examples, table 402 may also include a cost of the device(s) to be used for the procedure. In this example, the dose or other unit of medication may cost 100 US Dollars.

Table 402 may also include an MCS recommendation as discussed above.

Table 402 may also include confidence ratings. Confidence ratings may be an indication of a level of confidence for each treatment pathway of plurality of treatment pathways 404. For example, a level of confidence may be a measure of certainty which processing circuitry 204 has in predicted risks and/or outcomes associated with a given treatment pathway. For example, table 402 displays a confidence rating of 80% for the medication treatment pathway. In some examples, the confidence ratings may be set forth in a row of table 402 as shown. Additionally, or alternatively, confidence ratings may be presented as confidence intervals for each individual metric. For example, for the medication treatment pathway, table 402 shows complication of embolism at 0.1% (CI=±0.2%). In this example, CI denotes a confidence interval for the individual metric of the complication of embolism. In some examples, the confidence intervals may be displayed in a separate column, or only shown when a user hovers over the metric. In some examples, the confidence intervals might be shown in a fainter or smaller font or in another color. In some examples, a confidence interval may be the most suitable metric for certainty of predictions of processing circuitry 204 (e.g., based on statistical data processed through ML algorithm(s) 222, AI algorithm(s) 226, computer vision algorithm(s) 224, or the like). In some examples, processing circuitry 204 may use other statistical metrics to indicate certainty such as prediction interval, standard error, coefficient of determination (R2), etc.

However, applying the confident rating as a separate metric for the overall prediction (as currently indicated in the documentation) is also a valid option we may want to go with. In a sense, this would be about the same as putting a confidence interval beside the "Recommendation" metric—only positioned in a separate row.

In some examples, each of the entries into table 402 corresponding to a given treatment pathway may be color coded (e.g., the text may be of a colored font) indicating a relative standing of the prediction or inventory information amongst the plurality of treatment pathways. For example, predictions of relatively good effectiveness may be colored in green, predictions of relatively average effectiveness may be colored in yellow, and predictions of relatively poor effectiveness may be colored in red. Similarly, predictions of relatively little risk may be colored in green, predictions of relatively average risk may be colored in yellow, and predictions of relatively high risk may be colored in red. The same coloring may be used for recommendations, time to complete, inventory, MCS recommendations, or the like. In some examples, an icon or check box associated with each of the plurality of treatment pathways may be presented on page 400 which may be selectable or checkable by a clinician via input device(s) 210.

FIG. 5 is a conceptual diagram illustrating another example page of a user interface according to one or more aspects of this disclosure. Certain aspects of the example of FIG. 5 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

Based on a clinician selecting or checking such an icon or check box of page 400 of FIG. 4 or a clinician otherwise indicating a particular type of treatment pathway, such as "angioplasty," processing circuitry 204 may control display 206 to display user interface page 500 which may be a UI of user interfaces 218. Page 500 may display more options and associated information regarding a selected treatment pathway, such as angioplasty, as shown in the example of FIG. 5. For example, processing circuitry 204 may control display 206 to display page 500 if a clinician were to select the "angioplasty" treatment pathway of page 400.

Page 500 may include a plurality of options 504 for a given treatment pathway, such as angioplasty. For example, the options for angioplasty may include conservative, moderate, combative, typical for this physician (e.g., clinician), custom settings, or the like. For example, processing circuitry 204 may keep track of past procedures by a given clinician and display an option which may be a most common, a most common for a similar situation, or an average of the selected treatment pathway (e.g., angioplasty). The custom settings may be programmable by the clinician via input device(s) 210 and may be used to evaluate other options not displayed to the options displayed.

Page 500 may include table 502 including information similar to that of table 402 (e.g., recommendation, effectiveness, risk, time, inventory, and/or confidence rating), but this information may be specific to each of the displayed options, rather than the treatment pathway in general. For example, processing circuitry 204 may determine recommendation rankings, predicted effectiveness ratings, predicted risks, predicted time to complete, and/or track inventory for each treatment option of plurality of treatment options 504. Processing circuitry 204 may also determine recommended device(s) and device parameters (including settings) to be used for each displayed option. Table 502 may include the determined recommended device(s) and device parameters.

For example, table 502 may include a device section. The device section may include a recommended make and/or model of a device to be used during the procedure for each option (e.g., an SC Euphora device). The device section may include device parameters, such as specifications or settings to be used during the procedure. For example, table 502 may include a suggest length of a balloon of 12 mm, a suggested expanded diameter of the balloon of 2 mm, and a pressure to be used during the procedure of 1.7 ATM.

As in the example of FIG. 4, each of the entries into table 502 corresponding to a given treatment option may be color coded indicating a relative standing of the entry (e.g., prediction or inventory information) amongst plurality of treatment options 504. For example, predictions of relatively good effectiveness may be colored in green, predictions of relatively average effectiveness may be colored in yellow, and predictions of relatively poor effectiveness may be colored in red. Similarly, predictions of relatively little risk may be colored in green, predictions of relatively average risk may be colored in yellow, and predictions of relatively high risk may be colored in red. The same coloring may be used for recommendations, time to complete, inventory, confidence ratings, or the like. In some examples, an icon or check box associated with each of plurality of treatment options 504 may be presented on page 500 which may be selectable or checkable by a clinician via input device(s) 210.

Figure 6:
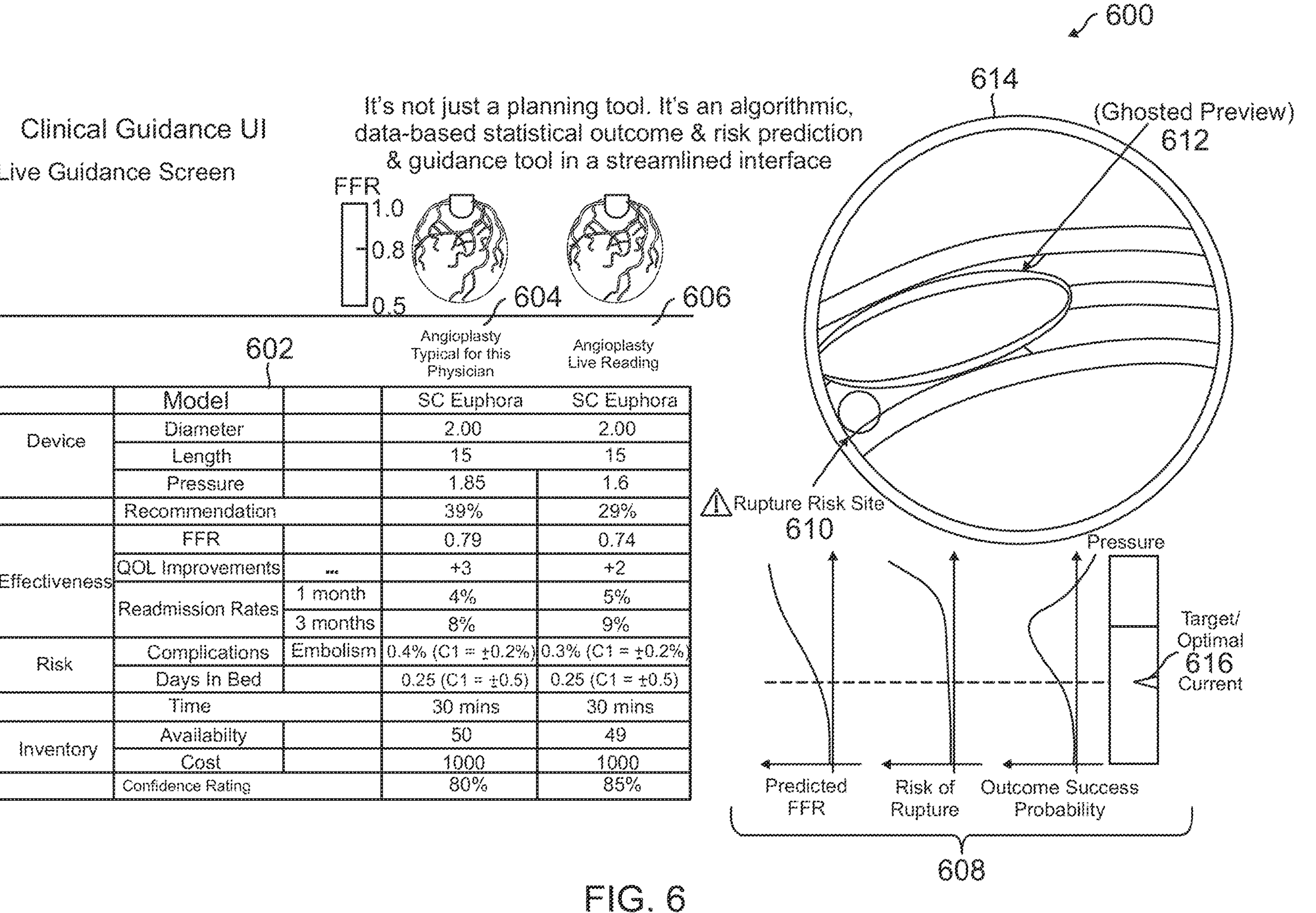
FIG. 6 is a conceptual diagram illustrating yet another example page of a user interface according to one or more aspects of this disclosure.

FIG. 6 is a conceptual diagram illustrating yet another example page of a user interface according to one or more aspects of this disclosure. Certain aspects of the example of FIG. 6 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

Based on a clinician selecting or checking such an icon or check box of page 500 of FIG. 5 or otherwise indicating a selected treatment pathway, processing circuitry 204 may control display 206 to display another user interface page, such as page 600, which may be a UI of user interface(s) 218. Page 600 may display the selected option 604 and associated information regarding selected option 604, as well as live reading 606 and associated information with respect to a procedure as the procedure is underway. For example, processing circuitry 204 may control display 206 to display page 600 if a clinician were to select the "typical for this physician" treatment option of page 500. Likewise, if the clinician were to select the "moderate" treatment option of page 500, processing circuitry 204 may control display 206 to display the "moderate" treatment option of page 500 instead of the "typical for this physician" treatment option as shown in FIG. 6. In some examples, processing circuitry 204 may automatically control display 206 to display the "typical for this physician" treatment option on page 600.

As can be seen from FIG. 6, table 602 contains the same information for selected option 604 as is included in table 502 for the "typical for this physician" treatment option. Live reading 606 may include live information relating to the ongoing procedure. For example, table 602 displays pressure of 1.6 for live reading 606. This pressure may be indicative of an actual pressure of the balloon at that time (or approximately at that time). For example, table 602 shows a recommendation of 29%, which may be indicative of a lower recommendation at the current pressure than would be for a balloon pressure of 1.85 ("typical for this physician"). For example, processing circuitry 204 may track current device settings and usage, determine a recommendation rating, predicted effectiveness rating(s), predicted risk(s), predicted time to complete, track current inventory, and control display 206 to display such information in table 602 in real time during the procedure.

Additionally, or alternatively, processing circuitry 204 may control display 206 to display other information. For example, display 206 may display one or more graphical representations 608. One or more graphical representations 608 may include a predicted FFR, a predicted risk of rupture, and/or a predicted outcome of success. In some examples, one or more graphical representations 608 may include an indication of a target or optimal device setting (e.g., pressure) and an indication of a current device setting in relation to the target or optimal device setting. Page 600 may also include depiction of target vasculature 614 which may include ghosted preview 612 of a device (e.g., balloon) and an identification of a rupture risk site 610 which may be used by the clinician when guiding and/or utilizing the device so as to better avoid a rupture.

In some examples, processing circuitry 204, via one or more of input device(s) 210 and/or display 206 may facilitate a clinician moving triangle 616 (or caret) to another position in the pressure bar to permit the clinician to visualize, e.g., vie page 600, where the predicted FFR, risk of rupture, and outcome of success probability would be at the pressure indicated by the moved triangle 616. In some examples, processing circuitry 204 may automatically output a control signal to an automated inflator/deflator (e.g., of additional equipment 152) to control a balloon (e.g., also of additional equipment 152) being used in an angioplasty procedure to inflate or deflate based on any of or any combination of a predicted FFR, a risk of rupture, or an outcome success probability at the current pressure of the balloon. In some examples, processing circuitry 204 may automatically output a control signal to the automated inflator/deflator to control a balloon being used in an angioplasty procedure to inflate or deflate so as to reach a target pressure. For example, processing circuitry 204 may determine the target pressure based on determined predicted FFR, risk of rupture, and/or outcome of success probability. In some examples, processing circuitry 204 may automatically output a control signal to automatically affect other devices and/or other device parameters.

As in FIGS. 4 and 5, information in page 600, including information in table 602, may be color coded. Additionally, one or more graphical representations 608 may be color coded. Depiction of target vasculature 614 may be color coded such that different anatomy, any lesions, devices or the like may be readily identifiable and distinguishable from each other.

A system which will makes suggestions on what devices to use, settings to apply, or warning of potential adverse events for a PCI procedure may be desirable. Such a system may help less experienced clinicians perform routine procedures with less supervision or more experienced physicians to have the confidence to take on and compete more complex procedures. A computing system that tracks device use, such as which device was used, and device settings such as the time of usage, pressure, other settings that were applied, and the outcomes, may auto populate patient medical records, and thus reduce the paperwork burden on clinicians post-procedure, thereby saving resources and costs.

As such, in some examples, processing circuitry 204 may determine and provide, to a clinician, treatment guidance and real time feedback on progress during the procedure. For example, processing circuitry 204 may determine and provide a clinician with device preparation instructions, instructions for use (IFU) information and live IFU walkthrough guidance, suggestions of on sizes and/or shapes of devices for use on the specific patient anatomy, or the like. Such devices may include guide wires, guide catheters, support catheters, balloons, or the like. For example, processing circuitry 204 may use or execute computer vision algorithm(s) 224 to determine characteristics of a lesion and/or determine a location of a lesion and execute ML algorithm(s) 222 and/or AI algorithm(s) 226 to provide the clinician with proposed treatment strategies (e.g., clinical guidance/informatics 220 and/or treatment pathways/options 230). In some examples, processing circuitry 204 may provide the treatment guidance and real time feedback on a same display as an angiogram, such as overlayed on an angiogram, or in the case of a hologram, integrated within the hologram.

For example, processing circuitry 204 may determine and provide, to a clinician via a display device (e.g., display 206), a location to treat and suggested position of one or more device(s) in the coronary vasculature of the patient, and/or device settings to apply, such as inflation pressure in the case of an angioplasty balloon. For example, processing circuitry 204 may provide a clinician with one or more suggested device(s) for predicted optimal support for the specific patient anatomy, for example, based on angulation and/or tortuosity. Processing circuitry 204 may control display 206 to display one or more device heat maps, indicating where a device has been, what the device has done, how long the device has been there, or the like. Processing circuitry 204 may control display 206 to display one or more suggested bifurcation techniques, chronic total occlusion (CTO) crossing techniques, or the like. Processing circuitry 204 may track devices in the patient in real time (e.g., via device tracking system 121) and control display 206 to display the location of devices in the patient (e.g., based on imaging data or other device tracking techniques), including feedback on how the procedure is progressing, warnings and live risk evaluation of potential adverse events based on real time procedure monitoring. Processing circuitry 204 may control display 206 to display lesion histology, length markers, stent information, other imaging data, information from earlier procedures, results of a completed current procedure, or the like.

Processing circuitry 204 may be configured to automatically determine, in real time, plaque morphology and vessel physiology from IVUS, OCT, CT, FFR, and/or other data, and output for display the plaque morphology and vessel physiology on angiogram imaging data during a procedure. For example, processing circuitry 204 may control display 206 to display determined plaque morphology and vessel physiology overlaid on live angiogram imaging data. In some examples, processing circuitry 204 may control display 206 to display determined plaque morphology and vessel physiology overlaid on the 3D model.

Processing circuitry 204 may suggest an entry point (e.g., radial and/or femoral) into the vasculature of the patient. Processing circuitry 204 may suggest an on-screen overlay of device shapes and/or sizes (e.g., guide catheter shape(s) and/or size(s), balloon shape(s) and/or size(s), or the like) to be displayed from which a clinician may select via input device(s) 210. Processing circuitry 204 may suggest an identification, for example, of a device, and/or location in a sterile field in the Cath lab. Processing circuitry 204 may suggest a time for which one of more device(s) are used and which device settings to be applied. Processing circuitry 204 may suggest the shape and size of guide catheter(s) to be used, properties of guidewires to be used (such as stiffness, support, tip, or the like) properties of stents to be used (such as length, diameter, pressure, or the like) and/or properties of balloons to be used (such as compliance, length, diameter, pressure, or the like).

Processing circuitry 204 may output dimensional measures on the angiogram display (e.g., display 206) to represent distance, such as overall dimensions, lengths, distances within the vasculature accounting for curves and/or views, or the like. For example, processing circuitry 204 may facilitate users interacting with system 100 via input devices 210 (e.g., via a peripheral device, by verbal commands via a microphone, by hand gestures via a camera, or the like) and/or display 206 to select which dimensions or parts of the anatomy, atheroma, device(s) or the like, from which the user may desire to see dimensional measurements.

Processing circuitry 204 may provide system guidance. For examples, computing device may provide suggestions for what sizes and/or shape of guide wires, guide catheters, support catheters, balloons, or the like, to be use for specific patient anatomy. Such suggestions may include an inflation pressure and position of the device to be used.

Processing circuitry 204 may track one or more device(s) in real time (e.g., via device tracking system 121) and may, via a display device such as display 206, provide indication(s) of such device(s) on the angiogram in real time. For example, processing circuitry 204 may highlight the tips of each guidewire and/or other device in real time in the displayed angiogram on display 206.

In some examples, processing circuitry 204 may determine or recognize a previously implanted medical device in imaging data 214 based on the characteristics of the imaging data 214 and information in electronic patient record 236 or entered by a clinician via input device(s) 210 or network interface 208, the information being indicative of the identity of the previously implanted medical device.

Processing circuitry 204 may provide predictions based on location of device in relation to specific patient anatomy.

For example, such predictions may be different if using the proximal end of a balloon on a lesion than if using the distal end. Processing circuitry 204 may control display 206 to display such predictions in real time.

Processing circuitry 204 may auto-calculate radiation dye (e.g., contrast) flow required based on what kind of image a clinician or processing circuitry 204 determines is desirable and how much radiation to which the patient has already been exposed. In some examples, processing circuitry 204 may also control a contrast injector (e.g., of additional equipment 152) to auto inject the calculated amount of contrast. Processing circuitry 204 may track medication and/or contrast which has been administered during the procedure, such as tracking the time it was administered, the volume administered, and/or the type administered. For example, processing circuitry 204 may employ computer vision algorithm(s) 224 to determine medication and/or contrast which has been administered during the procedure, obtain such information from one or more other devices of system 100, or obtain such information from input device(s) 210. For example, a clinician may input information regarding which medication and/or contrast has been administered during the procedure.

Processing circuitry 204 may recommend position(s) for imager 140 or other imager(s) 142, such as C-arm positions, based on a first angiogram, to obtain better or optimal views. Processing circuitry 204 may suggest, for rotational atherectomy, a speed, forcefulness, target reduction, and/or a predicted time to ablate based on lesion composition, lesion geometry, or the like.

Processing circuitry 204 may determine a predictive comparison of atherectomy methods, for example, rotational atherectomy compared with laser ablation. Such a prediction may be based on lesion composition, geometry, or the like. Processing circuitry 204 may control display 206 to display risk rates for each prediction. Processing circuitry 204 may account for the specific clinician performing the procedure and their level of experience and/or success at a particular procedure. For example, if the clinician performing the procedure is experienced with rotational atherectomy and/or has previously shown better than average success with rotational atherectomy, processing circuitry 204 may reduce predicted complication rates for a rotational atherectomy procedure. If the clinician is not experienced with rotational atherectomy and/or has previously shown worse than average success with rotational atherectomy, processing circuitry 204 may increase predicted complication rates for a rotational atherectomy procedure, or otherwise suggest a laser ablation or other type of procedure.

In some examples, processing circuitry 204 may output training/experience metrics to clinicians. For example, processing circuitry 204 may control display 206 to inform a clinician that if they practice rotational atherectomy x times per week, the clinician may be more able to handle highly complex cases when such cases arise. Processing circuitry 204 may also control display 206 to inform the clinician when a suitable, safe practice opportunity arises. Processing circuitry 204 may facilitate a clinician opportunities to optimize outcomes for all procedures (e.g., statistically), not just on a case-by-case basis.

In some examples, processing circuitry 204 may control display 206 to provide pop-up boxes (or other shapes) on the angiogram display identifying objects in the angiogram, such as vessel, calcium, a previous stent, or the like. In some examples, the display of such pop-up boxes may be selectable—in other words, a clinician may turn on or off the pop-up boxes, based on their personal preference via input device(s) 2010.

Processing circuitry 204 may be configured to automatically identify, in real time, plaque morphology, and control display 206 to highlight any vessel vulnerability (e.g., dissection, perforation risk, or the like) in the displayed angiogram.

In some examples, processing circuitry 204 may control display 206 to display ghost image(s) of previous device placement(s). For example, processing circuitry 204 may control display 206 to display a heat map of rotational atherectomy runs, ablations, balloon inflations, or the like.

Processing circuitry 204 may display warnings and suggestions during the procedure on the angiogram screen. In some examples, warnings may include alerts or alarms. In some examples, processing circuitry 204 may, alternatively or additionally, issue such warnings via one or more speakers, lights, or other output devices of output device(s) 212 or other output devices of system 100. For example, processing circuitry 204 may highlight stent apposition/position (e.g., using red/yellow/green colors) based on angiogram and a stent size. Processing circuitry 204 may identify and track each individual device in the patient (e.g., via device tracking system 121). For example, if multiple wires are used in the patient, processing circuitry 204 may separately identify them on the angiogram display so that the clinician may tell them apart.

Processing circuitry 204 may co-register other data such as IVUS, OCT, FFR, NIRS, or the like, with each other and/or with the angiogram imaging data and control display 206 to display the other data with the angiogram imaging data. For example, processing circuitry 204 may execute computer vision algorithm(s) 224 to determine common reference structures in the imaging data and anchor the common reference structures together as part of co-registering the imaging data.

In some examples, processing circuitry 204 may generate atherosclerosis morphology and/or composition data such as the lipid, fibrous, calcified, necrotic or other such characteristics. Processing circuitry 204 may control display 206 to display the atherosclerosis morphology and/or composition data with a certainty (e.g., confidence rating) or as a probabilistic estimate. Processing circuitry 204 may similarly identify and control display 206 to display vessel dissections, implanted devices (such as stents), highlight malposed (or otherwise imperfect) implanted devices, embolisms, thrombus, or the like. Processing circuitry 204 may control display 206 to highlight regions of the atherosclerosis or anatomy as being at risk of incurring such features, and indicate an estimated probability of this risk. These features may be informed by data from devices such as such as IVUS, OCT, NIRS, CT devices, and/or other such devices and may be updated live or informed by previously captured data (such as from a DICOM file or otherwise). In some cases, processing circuitry 204 may identify and control display 206 to display a representation of this data (e.g., overlaid on) the angiogram imaging data, for example, in a real time feedback loop. In some examples, processing circuitry 204 may control display 206 to display such features using semi-opaque and/or color-coded morphological features in a virtual 3D model (e.g., 3D model 232 or 3D model 306).

In some examples, processing circuitry 204 may provide easy access to past angiograms and/or other data. For example, processing circuitry 204 may make inferences based on changes to patient history and/or imaging-based input to estimate a nature of a lesion, such as whether the lesion is calcified, or the like. Processing circuitry 204 may control display 206 to highlight changes between a past angiogram and a current angiogram. Processing circuitry 204 may determine and recommend a lesion preparation strategy (e.g., rate of disease progression, predict probable future problem areas based on patient's disease history and current flow data, or the like) and may control display 206 to display the recommended lesion preparation strategy, e.g., overlaid on the angiogram imaging data.

In some examples, processing circuitry 204 may be configured to act as a live instructions for use (IFU) system. For example, processing circuitry 204 may employ one or more computer vision algorithm(s) 224 and/or inventory tracking algorithm(s) 234 to determine specific device(s) in use and a current stage of the procedure. For example, computer vision algorithm(s) may be trained on specific devices of additional equipment 152 so as to recognize one device of additional equipment from another. One or more cameras of input device(s) 210 or additional equipment may be used to capture images of devices of additional equipment 152 that are used during the medical procedure. Processing circuitry 204 executing one of more of computer vision algorithm(s) 224 may determine a specific device being used and update an accounting of inventory in memory to deduct the used device, for example, in inventory tracking algorithm(s) 234.

In some examples, inventory tracking may be implemented via NLP algorithm(s) 228, rather than, or in addition to, computer vision algorithm(s) 224. For example, a clinician may verbally state which device they are using. One or more microphones of input device(s) 210 and/or additional equipment 152 may capture such speech. NLP algorithm(s) 228 may determine which device is being used based on the captured speech and interact with inventory tracking algorithm(s) 234 to update an accounting of inventory accordingly. Processing circuitry 204 may output for display the next steps of the procedure for the clinician to take. In some examples, processing circuitry 204 may control display 206 to provide visual (in some cases, animated) and/or textual-based instructions which may be derived from or taken directly from a specific device IFU. In some examples, processing circuitry 204 may control display 206 to provide separate panels (e.g., windows) on a display screen or control multiple displays (display 206, display device 110, output device(s) 212, etc.) with a specific panel or display being associated with a specific person in the Cath lab (physician, nurse, etc.) with IFU for the device(s) for which that person may be responsible. As such, processing circuitry 204 may optimize or improve a workflow for the full Cath lab team concurrently. For example, processing circuitry 204 may provide a panel for a physician to review patient details and procedure plans, a panel for a first nurse to collect a specified guide catheter which may be suitable for the patient and to pass the specified guide catheter into a sterile field to a second nurse, a panel for the second nurse to prepare the patient as specified, or the like. As each of the team members complete their instructed step, processing circuitry 204 may control display 206 to update their respective panel to the next step automatically, or by clinician input, such as by voice command). Such techniques may provide for a "lean lab" by providing procedural optimization. Such techniques may also provide useful training and guidance on basic procedural steps for less experienced team members. Such techniques may also ease the cognitive burden on senior members, thereby reducing the need for the senior members to instruct junior members on basic use of devices.

In some examples, computing device 150 may track clinician positions and movement in the Cath lab and provide a warning regarding radiation exposure in order to support the reduction of radiation exposure to Cath lab clinicians. More details on tracking clinician positions and movement in the Cath lab and provide a warning regarding radiation exposure may be found in U.S. Provisional Patent No. 63/375,758, entitled RADIATION EXPOSURE MAPPING SYSTEM, filed Sep. 15, 2022, the entirety of which is hereby incorporated by reference.

In some examples, processing circuitry 204 may determine and provide real time device manipulation guidance, tips, and/or suggestions for clinicians. For example, processing circuitry 204 may control display 206 to display such guidance, tips and/or suggestions together with the angiogram imaging data. In some examples, processing circuitry 204 may control display 206 to display such guidance, tips and/or suggestions overlayed on the angiogram imaging data.

In some examples, system 100 may collect information for robotic and/or automated device control. System 100 may also control these robotic and/or automated devices. Such robotic and/or automated devices may be devices of additional equipment 152. Systems 100 may use ML/AI features to train and control robotic and/or automated devices, such as Reinforcement Learning, Deep Evolutionary Reinforcement Learning (DERL), Heuristic-Guided Reinforcement Learning, in addition to other ML/AI techniques such as those described herein.

Processing circuitry 204 may identify one or more devices using computer vision algorithm(s) 224, QR code, bar code, or the like. Processing circuitry 204 may track the device(s) during the procedure, for example, using device tracking system 121. Processing circuitry 204 may use passive measurement sensor attachments on devices to track the device(s) during the procedure. For example, processing circuitry 204 may use Bluetooth, wired, QR code, barcode, EPROM, NFC, camera sensor(s), or the like to identify the device(s) and/or track device(s). In some examples, processing circuitry 204 may control display 206 to display a representation of device location(s) overlaid on the angiogram imaging data.

Processing circuitry 204 may track the live workflow in real time for optimization and synchronizing IFU guidance prompts and/or warnings. For example, processing circuitry 204 may utilize lab monitoring camera(s), an IFU database, computer vision algorithm(s) 224, or the like, to track the live workflow. Processing circuitry 204 may utilize displays available in the Cath lab (e.g., display 206, display device 110, output device(s) 212, etc.) to provide synchronized IFU guidance prompts to Cath lab clinicians and/or warnings. Processing circuitry 204 may provide such a warning, for example, when computing device predicts a risk is relatively high based on activity during a procedure.

Processing circuitry 204 may track and record device settings using: pressure, flow, on screen data, device captured information, or clinician feedback, electronic signals, energy delivered the body or measured from any sensor, or other information. Processing circuitry 204 may track pharmacological agents (e.g., medicines, contrasts, etc.) using, for example, flow, pressure, ultrasound, timing information, or the like. For example, processing circuitry 204 may apply time stamps when devices or pharmacological agents are used and/or when therapy is applied.

In some examples, processing circuitry 204 may control display 206 to display a "ghosted" version of one or more virtual device(s) over a target treatment area. For example, processing circuitry 204 may determine a 3D, scaled model of devices being used in the procedure with defining characteristics of each of the devices (e.g., catheter flexibility and conformity to the anatomy). For example, processing circuitry 204 may use multi-body dynamics, FEA, optimized physics engine, reinforcement learning AI, graphics engine image processing, gesture and/or voice control virtual model manipulation, to generate such virtual target devices and/or a 3D model of the patient anatomy. Processing circuitry 204 may obtain and utilize CT imaging data, angiogram imaging data, and AI data processing to determine device location(s) in anatomy of the patient and generate the virtual devices for display. In some examples, processing circuitry 204 may obtain and utilize FFR values, CT imaging data and angiogram imaging data and process such imaging data using one or more AI algorithms to determine device location(s) in anatomy of the patient and generate the virtual devices for display. In some examples, processing circuitry 204 may obtain and utilize FFR values, angiogram imaging data, IVUS and/or OCT imaging data and process such imaging data using one or more AI algorithms to determine device location(s) in anatomy of the patient and generate the virtual devices for display. In some examples, processing circuitry 204 may alternatively or additionally obtain and utilize NIRS imaging data.

Processing circuitry 204 may determine performance predictions based on AI algorithm(s) 226, ML algorithm(s) 222, and/or computer vision algorithm(s) 224 which may match previous similar scenarios and analyze outcomes when performed in a specified manner. For example, processing circuitry 204 may determine performance predictions based on computational simulations (FEA, Multibody Dynamics, custom algorithms, or the like). In some examples, processing circuitry 204 may run a plurality of combinations of simulations of different scenarios to determine a best predicted outcome. In examples where there is not enough training data to provide a performance prediction at a specific confidence level, processing circuitry 204 may provide a generally wide confidence interval on predictions, for example 20%-80%, rather than a specific confidence level, such as 56%.

Processing circuitry 204 may automatically generate electronic patient record 236 using information collected during the procedure and/or using NLP algorithm(s) 228. For example, system 100 may include one or more microphones (e.g., of input device(s) 210) which may capture spoken words during the procedure which processing circuitry 204 may obtain and use to fill out various fields in an electronic patient record of the procedure. In some examples, processing circuitry 204 may filter out language that is not clinically relevant so that only clinically relevant language is recorded and/or input into the patient record. In some examples, processing circuitry 204 facilitate a user to review the recorded and/or transcribed data and manually choose relevant data to include or exclude from electronic patient record 236. For example, processing circuitry 204 may execute one or more software tools of applications 216 designed to facilitate and streamline this selection process. Processing circuitry 204 may also execute automated algorithms of application s 216 to speed the review and editing process up and allow for guided and/or supervised automation for the review and editing process.

In some examples, processing circuitry 204 may be configured to recognize hand gestures from camera captured imaging data through the use of computer vision algorithm(s) 224 and/or voice commands through the use of natural language processing. In some examples, input device(s) 2010 may include a touch screen, which may allow multiple touch options.

In some examples, processing circuitry 204 may link real world outcomes to previous treatments and scenarios to optimize future predictions. For example, previous treatments and scenarios and resulting outcomes may be used to train ML algorithm(s) 222 used by processing circuitry 204 to suggest procedures and/or outcomes.

For example, processing circuitry 204 may transform all obtained data during the procedure into the virtual 3D model of the patient anatomy. For example, processing circuitry 204 may generate 3D model 232 using information from a plurality of sources, such as imaging data 214 from imager 140 and/or additional imager(s) 142, information from additional equipment 152, electronic patient record 236, and/or other information discussed herein. In some examples, 3D model 232 may be referred to as a "digital twin" of the patient anatomy.

In some examples, processing circuitry 204 may preprocess and standardize training data for ML algorithm(s) 222. In some examples, processing circuitry 204 may match a format of inference data (e.g., data from which processing circuitry 204 may make predictions and/or recommendations.

Figure 7:
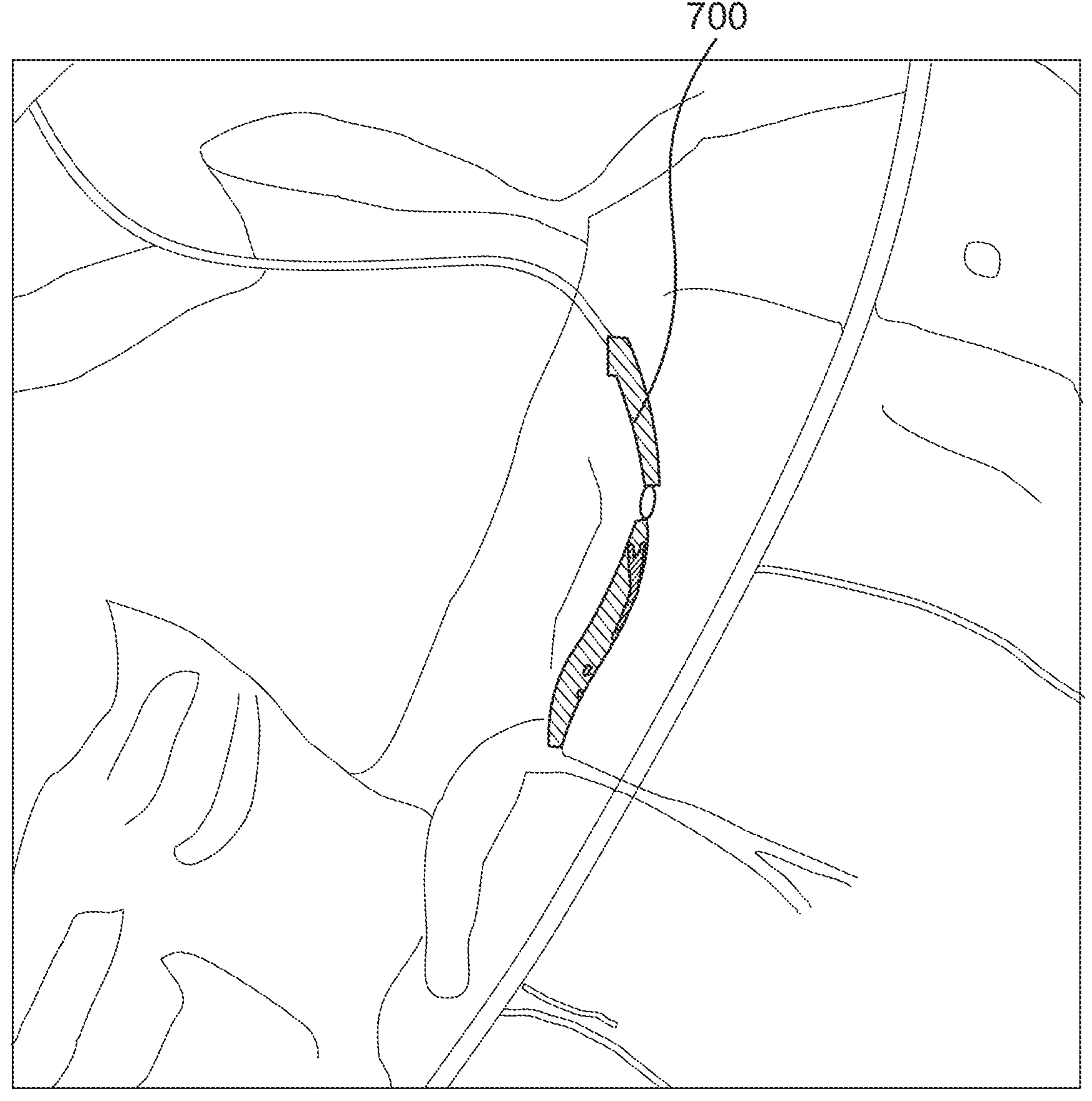
FIG. 7 is a conceptual diagram illustrating an example heat map in accordance with one or more aspects of this disclosure.

FIG. 7 is a conceptual diagram depicting an example heat map according to one or more aspects of this disclosure. Certain aspects of the example of FIG. 7 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

Processing circuitry 204 may determine a heat map 700. Processing circuitry 204 may control display 206 to display heat map 700 overlaid on the angiogram imaging data. Heat map 700 may be a live map which may track locations of device(s) within the coronary vasculature of the patient, including, for example where the devices were, where the devices are, and/or where the devices are going in a vessel. For example, it may be useful to see where devices have been, and what area(s) have been treated, for energy delivery devices, plaque removal, or the like. For example, it may be desirable to track where treatment has been delivered live on screen when using an atherectomy device, an intravascular lithotripsy (IVL) device, or the like. For example, processing circuitry 204 may track on heat map 700 where an atherectomy device has treated, where power was delivered and lithotripsy for an IVL device, where energy was delivered for renal denervation (RDN), wire movement history, or the like.

Heat map 700 may display different areas of treatment in different colors or greyscale, or in other ways to differentiate between the type of treatment, the intensity or extent of treatment, or the like. For example, processing circuitry 204 may display areas of no treatment in grey scale, areas of light treatment in green, areas of medium treatment in yellow, and areas of high treatment in red.

Figure 8:
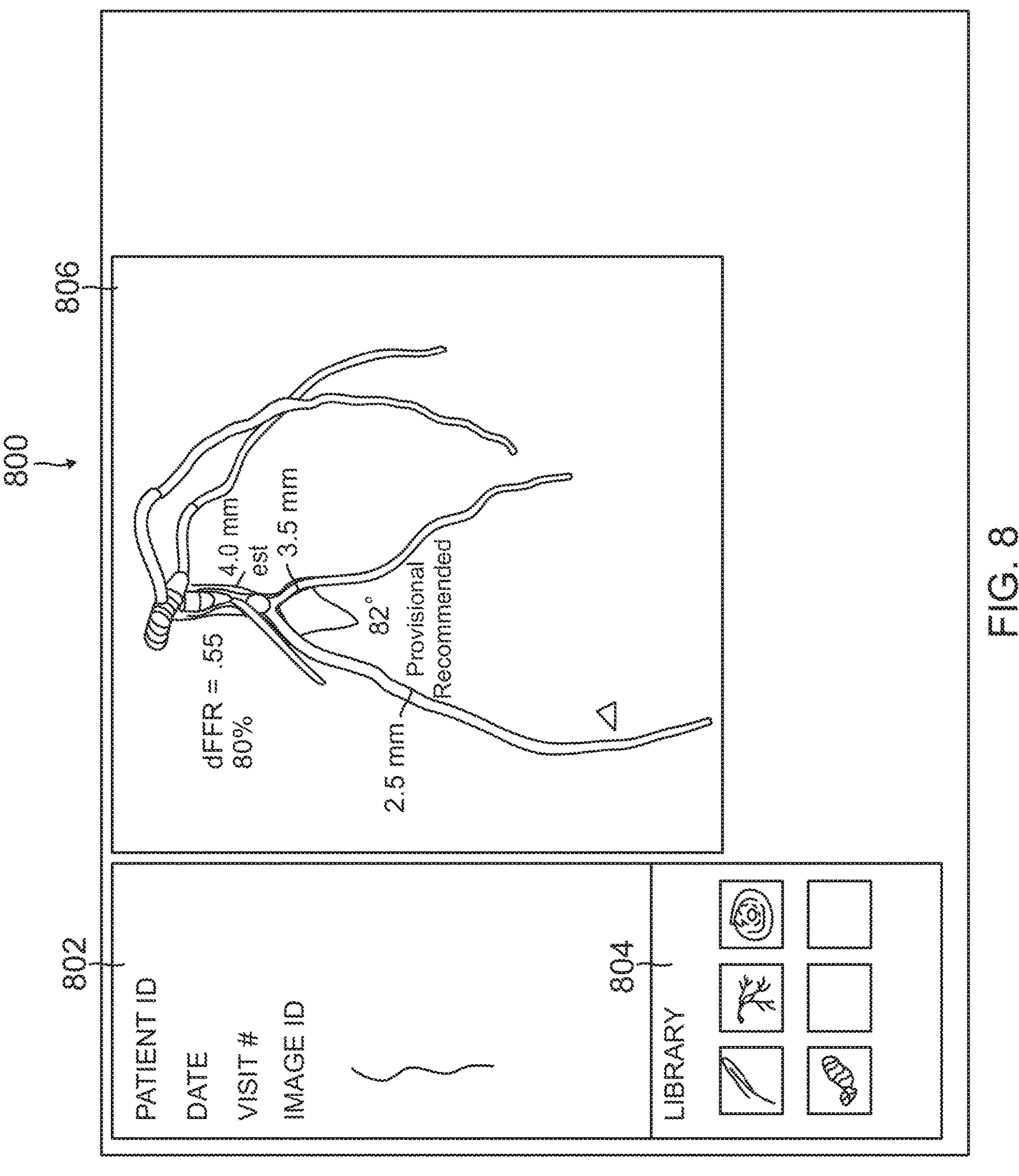
FIG. 8 is a conceptual diagram illustrating example bifurcation guidance in accordance with one or more aspects of this disclosure.

FIG. 8 is a conceptual diagram of an example user interface for a bifurcation procedure according to one or more aspects of this disclosure. Certain aspects of the example of FIG. 8 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

UI 800 may be a UI of user interface(s) 218. For example, display 206 may display UI 800 which may include a plurality of panels or windows. First panel 802 may include procedure details, such as patient ID, date, visit number, image ID, or the like. Processing circuitry 204 may store such procedure details in clinical guidance/informatics 220 along with other information relating to the procedure or collected during the procedure, such as other imaging data, 3D model 306, or the like. Such information may also be used by processing circuitry 204 to automatically fill out electronic patient record 236 (FIG. 2). A second panel may include a library 804 displaying graphical user interfaces (GUIs) and/or other representations of other information which, when selected (e.g., via input device(s) 210) cause other information to be displayed in a main panel or in a pop-up panel. Such other information may include recommendations for procedures, imaging data, the 3D virtual model, or the like.

Main panel 806 may display a representation of vessels of patient associated with the bifurcation procedure and associated information. For example, main panel 806 may display target anatomy, surrounding anatomy, diastolic FFR (dFFR) values, vessel diameters, angles of bifurcation, or the like. In some examples, vessels displayed for the bifurcation procedure may be highlighted in different colors. For example, the target anatomy for treatment may be highlighted in one color while surrounding anatomy may be highlighted in different color(s). In some examples, the colors may be indicative of a predicted need for treatment. For example, the bifurcation vessel may be highlighted in red, vessels in need of other treatment may be highlighted in orange, vessels in lesser need of treatment may be highlighted in yellow, vessels not in need of treatment may be highlighted in white, or the like. In some examples, main panel 806 may display angiogram imaging data with additional information, such as dFFR values, vessel diameters, angles of bifurcation, or the like, overlaid upon or otherwise displayed with the angiogram imaging data. In some examples, processing circuitry 204.

Processing circuitry 204 may track device utilization, such as atherectomy device passes. In some examples, system 100 may include smart manifold(s) or device add-on(s) (e.g., of additional equipment 152) to track start and stop times, if the devices do not already track such information. The system may overlay any of this information on a graphical display. In some examples, processing circuitry 204 may facilitate users to customize and choose which of such metrics they want to have displayed on display 206. For example, processing circuitry, via input device(s) 210 or display 206, may permit a user to customize selected elements of a UI to suit their preferences. Processing circuitry may allow for the creation of user profiles with a saved set of customized settings. For example, processing circuitry may obtain user input (e.g., via input device(s) 210 or display 206) and save such customized settings in user profiles 234 of memory 202. These settings might be used by processing circuitry 204 to determine the metrics shown, views displayed, and other such preferences. A used may select their user profile via a username/password system which may draw information from an existing hospital IT system. In some examples, processing circuitry 204 may determine which user profile of user profiles 234 to use automatically via facial or voice recognition, for example, by executing one or more of computer vision algorithm(s) 224. These custom settings may be persistently saved and reactivated on later use. Each user may have the ability to create numerous combinations of settings which can be saved, edited, and selected depending on their situational preferences.

As previous described for stent and balloon inflation examples above, for bifurcation guidance, processing circuitry 204 may utilize imaging data, such as imaging data acquired before or during a procedure, to identify key vessel physiology, morphology, dimensions, and/or attributes which may help facilitate better decision making before treating a bifurcation. For example, processing circuitry 204 may utilize the 3D virtual model to test treatment strategies and provide suggestions. Processing circuitry 204 may display a 3D virtual model showing a target end point and may track process of the actual devices during the procedure.

For example, processing circuitry 204 may determine MEDINA score(s), branch size(s), branch angle(s), suggested landing zone(s), suggested approach(es), or the like, immediately prior to the procedure and/or during the procedure, or off-line (e.g., prior to the procedure). For example, processing circuitry 204 may generate a 3D coronary tree model. Processing circuitry 204 may determine a size of vessels in major-minor axis and include such sizes in the 3D model. Processing circuitry 204 may estimate stenosis levels and/or FFR (e.g., digital FFR) values. Processing circuitry 204 may determine or measure side branch angles. In some examples, processing circuitry 204 may control display 206 to display such additional information overlaid upon or otherwise displayed with the angiogram imaging data in main panel 806.

Figure 9:
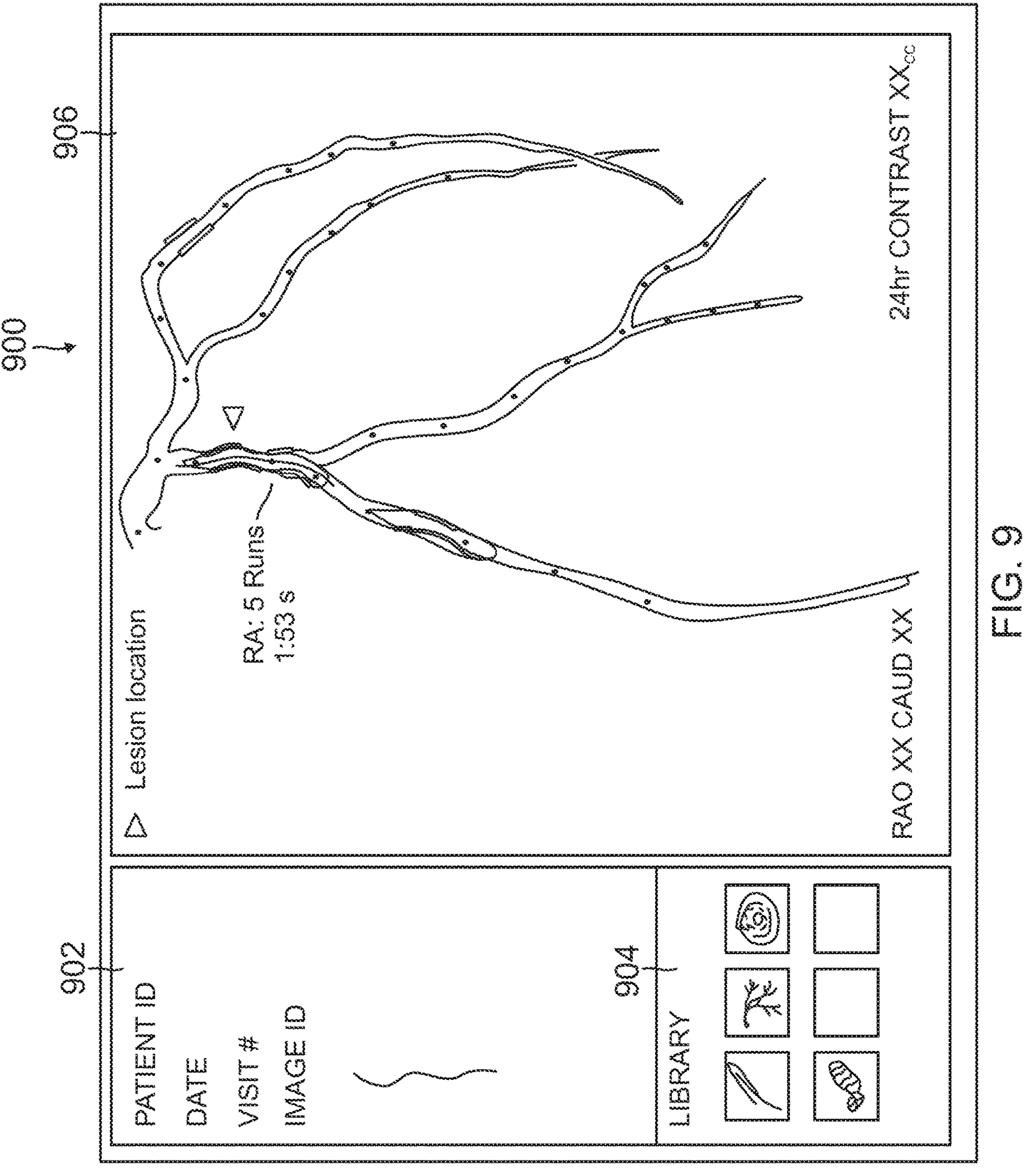
FIG. 9 is a conceptual diagram illustrating another example of bifurcation guidance in accordance with one or more aspects of this disclosure.

FIG. 9 is a conceptual diagram of another example user interface for a bifurcation procedure according to one or more aspects of this disclosure. Certain aspects of the example of FIG. 9 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

UI 900 may be a UI of user interface(s) 218. As in FIG. 8, display 206 may display UI 900 which may include a plurality of panels or windows. In the example of FIG. 9, main panel 906 depicts the angiogram imaging data with virtual model(s) of the device(s) being used superimposed on the angiogram imaging data. For example, main panel 906 may display a virtual model 908 of an atherectomy device in the vasculature of the patient overlaid on the angiogram imaging data. Main panel 906 may be accessible from the library of the example of FIG. 8. Main panel 806 of FIG. 8 may be represented in and selectable from library 904 of FIG. 9.

Similar to the example of FIG. 8, UI 900 of FIG. 9 includes first panel 902 including procedure details and second panel 904 includes a library with GUIs and/or other representations of other information which may lead to other information which may be displayed in a main panel or in a pop-up panel when selected by a clinician, e.g., via input device(s) 210.

Main panel 906 may include an identifier of the lesion location, such as an arrow or carat pointing to the lesion, a highlighting or outlining of the lesion, or the like, overlaid on the angiogram imaging data. For example, virtual model 908 may be overlaid on the angiogram imaging data and usage may be displayed, such as "RA: 5 Runs 1:52 s," which may indicate that the indicated area was subjected to 5 runs of ablation for a total of 1.52 seconds. Other information typically displayed with angiogram data may also be displayed in the UI, such as the viewing perspective (right anterior oblique (RAO), caudal (CAUD)), amount of contrast used over the last predetermined period of time, etc.

Figure 10:
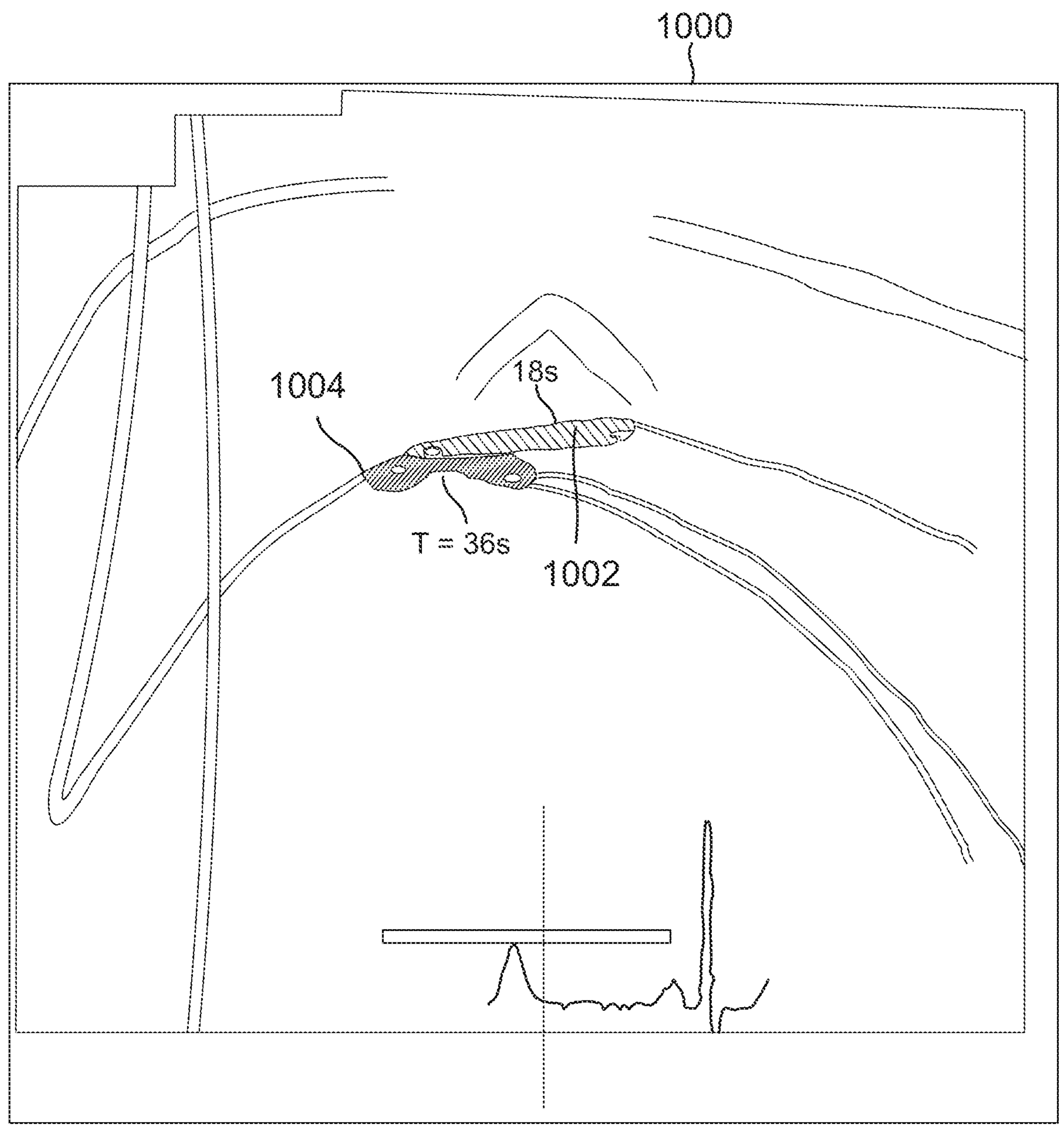
FIG. 10 is a conceptual diagram illustrating an example of balloon guidance according to one or more aspects of this disclosure.

FIG. 10 is a conceptual diagram illustrating an example of balloon treatment guidance according to one or more aspects of this disclosure. Certain aspects of the example of FIG. 10 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

For example, processing circuitry 204 may control display 206 to display UI 1000 depicting a plurality of proposed balloon treatments for a patient. UI 1000 may be a UI of user interface(s) 218 (FIG. 2). UI 1000 may be selectable from a library, such as library 804 and/or library 904 FIGS. 8 and 9, respectively. In some examples, UI 1000 may be displayed in a main panel of a UI rather than occupy an entire screen. In the example of FIG. 10, two suggested balloon treatments are depicted. First treatment 1002 at an indicated location is proposed for 18 seconds. Such a treatment may be a relatively lighter treatment than second treatment 1004 and may be represented, for example in a different color to differentiate first treatment 1002 treatment and/or to indicate first treatment 1002 is lighter than second treatment 1004. Second treatment 1004 is at a second location and is proposed for 36 seconds. Second treatment 1004 may be a relatively heavier treatment than first treatment 1002 and may be represented, for example in a different color to differentiate second treatment 1004 from first treatment 1002 and/or to indicate second treatment 1004 is heavier than first treatment 1002. In some examples, processing circuitry 204 may control display 206 to display UI 1000 in a main panel, such as main panel 806 or 906, of a UI.

Figure 11:
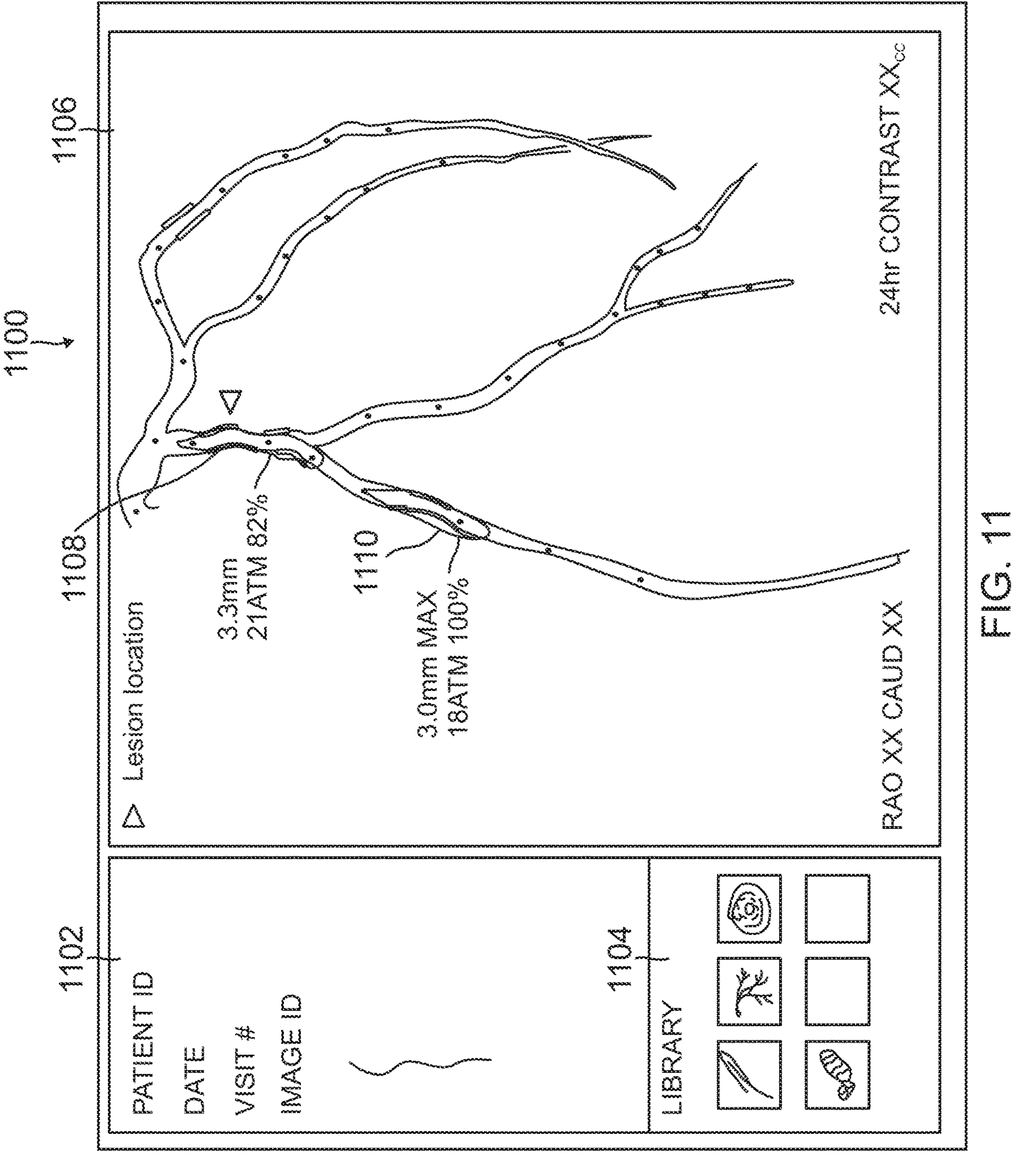
FIG. 11 is a conceptual diagram illustrating an example of a balloon guidance UI according to one or more aspects of the present disclosure.

FIG. 11 is a conceptual diagram illustrating an example user interface for use with a balloon procedure. Certain aspects of the example of FIG. 11 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

UI 1100 may be a UI of user interface(s) 218 (FIG. 2). As in FIGS. 8 and 9, UI 1100 may include a plurality of panels or windows. UI 1100 includes main panel 1106 which depicts angiogram imaging data with virtual models 1108 and 1110 of the balloons overlaid on the angiogram imaging data. Main panel 1106 may be accessible from library 804 and/or library 904 of the examples of FIGS. 8 and 9, respectively.

Similar to the examples of FIGS. 8 and 9, UI 1100 of FIG. 11 includes first panel 1102 including procedure details. Second panel 1104 includes a library with GUIs and/or other representations which may lead to other information which may be displayed in main panel 1106 or in a pop-up panel when selected by a clinician, e.g., via input device(s) 210.

Main panel 1106 may display the angiogram imaging data, including locations of lesion(s) and balloon positions (e.g., virtual models 1108 and 1110) overlaid on the angiogram imaging date. For example, the balloon positions may be overlaid on the angiogram imaging data. Main panel 1106 may include a predicted (or actual) diameter of the vessel after treatment with the balloon and/or a pressure to be used (or actually used) and/or a percentage of maximum pressure for the balloon. For example, an upper balloon treatment area in the vicinity of virtual model 1108 is shown with a diameter of the vessel shown as 3.3 mm and a pressure of the balloon at 21 ATM which may be 82% of the maximum pressure for the balloon. A lower balloon treatment area in the vicinity of virtual model 1110 is shown with a diameter of the vessel shown as 3.0 mm and a pressure of the balloon at 18 ATM which may be 100% of the maximum pressure for the balloon. Main panel 1106 may also suggest the estimated optimal setting to use for devices, based on an algorithm which analyses historical clinical data of anatomy, patient data, outcome data, and devices and settings applied previously. For example, an estimated optimal setting may include the estimated optimal balloon pressure the user should apply in order to optimize patient outcomes vs risk of adverse events. Panel 1106 may visually highlight this estimated optimal value using a line or marker on display 206.

For example, processing circuitry 204 may employ computer vision algorithm(s) 224 and/or a smart manifold to track balloon deployment in 3D. Processing circuitry 204 may control display 206 to display in main panel 1106 ghosts or virtual models 1108 and 1110 indicating balloon positions in the vasculature of the patient overlaid on the angiogram imaging data. Processing circuitry 204 may estimate balloon maximum expansion, determine predicted dog boning (e.g., the expansion of a balloon at the distal and proximal ends such that the balloon resembles a dog bone), or the like. Processing circuitry 204 may control display 206 to display representations of the estimated balloon maximum expansion, dog boning (e.g., such as in virtual model 1110), or the like, in main panel 1106 overlaid on angiogram imaging data. Processing circuitry 204 may track contrast and pressures and/or identify changes in flow. After treatment, processing circuitry 204 may recalculate an estimated dFFR, highlight any dissections, or changes in Thrombolysis in Myocardial Infarction (TIMI) flows, and/or compare current results of the balloon treatment to previous results (e.g., of the same or prior procedures), and may control display 206 to display the results in main panel 1110, for example, overlaid on the angiogram imaging data.

Figure 12:
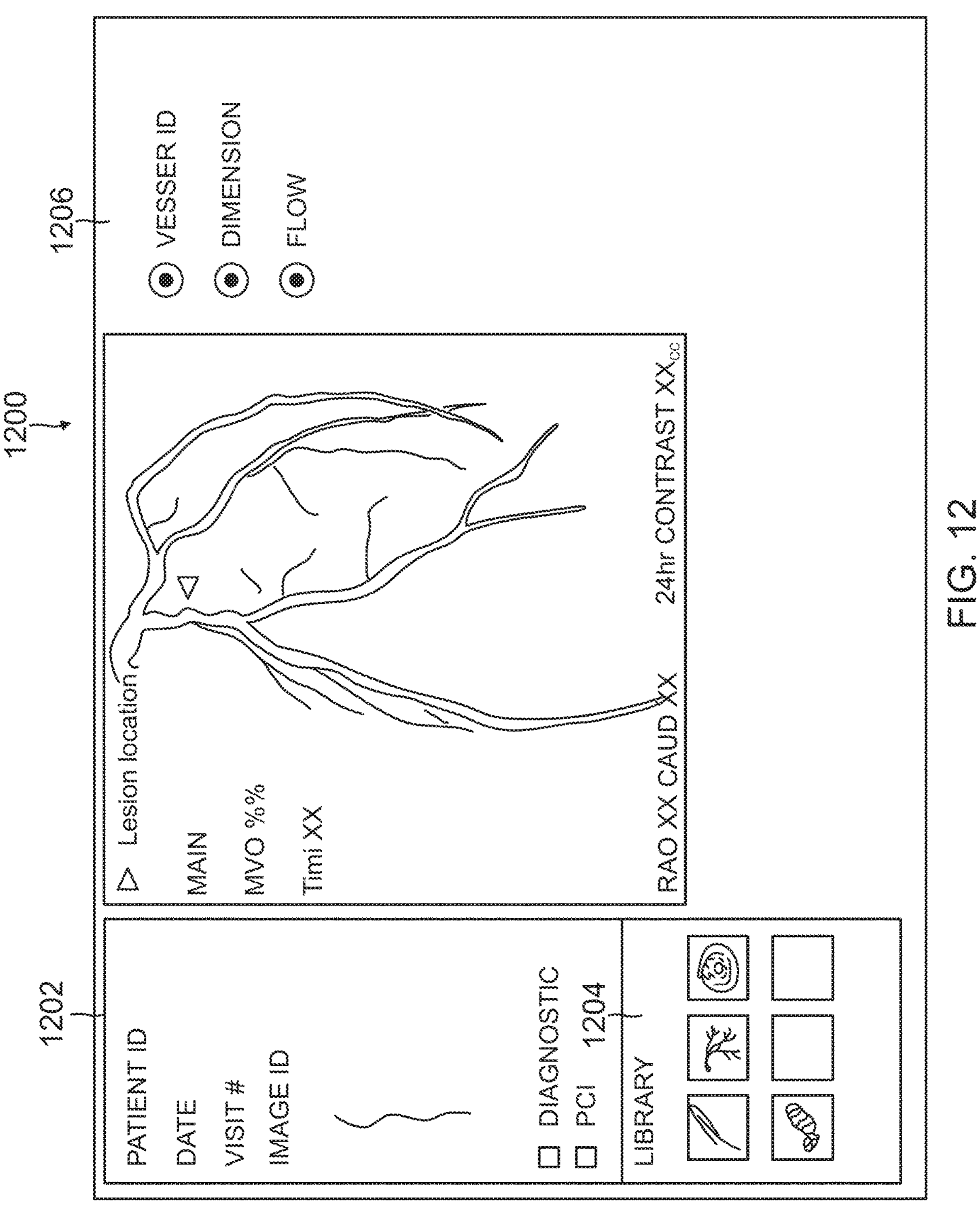
FIG. 12 is a conceptual diagram illustrating another example of a balloon guidance UI according to one or more aspects of the present disclosure.

FIG. 12 is a conceptual diagram of another example user interface for use with a balloon procedure according to one or more aspects of this disclosure. Certain aspects of the example of FIG. 12 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

UI 1200 may be a UI of user interface(s) 218 (FIG. 2). Similar to the example of FIG. 11, UI 1200 includes first panel 1202 including procedure details. Second panel 1204 includes a library with GUIs and/or other representations which may lead to other information which may be displayed in main panel 1206 or in a pop-up panel when selected by a clinician, e.g., via input device(s) 210. In some examples, main panel 1206 is selectable in library 1104. In other examples, processing circuitry 204 automatically displays main panel 1206 in place of main panel 1106 once all of the balloon treatments have occurred.

Main panel 1206 depicts the angiogram imaging data after the balloon treatment(s) with additional information overlaid thereon or depicted along-side of the angiogram imaging data. For example, main panel 1206 may include outlines or highlights of the main vessel(s) in the angiogram imaging data and may include information such as microvascular obstruction (MVO) percentage and TIMI values. Main panel 1206 may also include such other information as a vessel ID, dimensions of the vessel, and/or flow information.

For example, processing circuitry 204 may identify vessels, such as main vessels, secondary vessels, or the like. Processing circuitry 204 may capture positions of vessels. Processing circuitry 204 may use a smart manifold to track contrast usage and devices. Processing circuitry 204 may estimate TIMI flow from image recordings. Processing circuitry 204 may match current angiogram imaging data to previous CT and/or angiogram data, for example, to determine a degree of success of a treatment.

Figure 13:
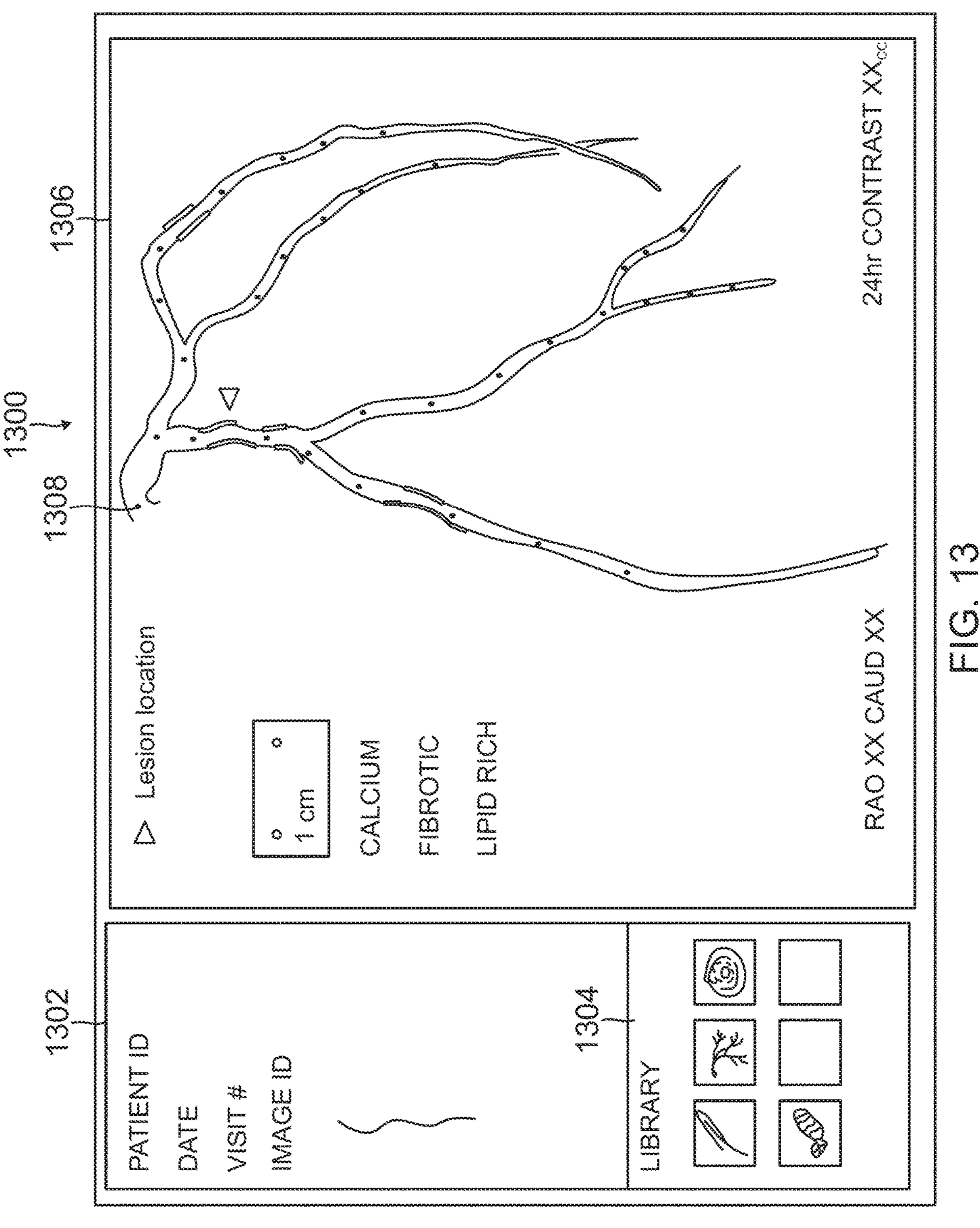
FIG. 13 is a conceptual diagram illustrating an example overlay UI according to one or more aspects of the present disclosure.

FIG. 13 is a conceptual diagram illustrating an example user interface for displaying lesion history according to one or more aspects of this disclosure. Certain aspects of the example of FIG. 13 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

UI 1300 may be a UI of user interface(s) 218 (FIG. 2). Like several earlier examples, UI 1300 includes first panel 1302 displaying procedural information and second panel 1302 displaying a library. Main panel 1306 displays information overlaid on angiogram imaging data. The information included in main panel 1306 may include distance markers. Distance markers may be useful because a 3D image displayed on a 2D display may distort distances. For example, if a vessel travels perpendicular to the direction of the 2D display, the distance traveled by that vessel would appear to be 0 although that vessel has some length in the perpendicular direction. For example, main panel 1306 depicts distance markers (represented with dots), such as distance marker 1308, within the displayed vessels of the angiogram imaging data at 1 cm intervals. Main panel 1306 may also display different properties of lesions, such as calcium, fibrotic, and lipid rich areas, for example using color coded highlights. For example, each property may be represented by highlights overlaid on the angiogram imaging data using a different color.

For example, processing circuitry 204 may control display 206 to place distance markers in or along the vessels displayed to highlight foreshortening. Processing circuitry 204 may co-register the coronary tree of the angiogram imaging data with a 3D model. For example, processing circuitry 204 may execute computer vision algorithm(s) 224 to determine common reference structures in the angiogram imaging data and 3D model 306 and anchor the common reference structures together as part of co-registering the angiogram imaging data and 3D model 306.

For example, processing circuitry 204 may control display 206 to display vessel ghosts without contrast. Processing circuitry 204 may visually estimate lesions, calcifications, or the like, or may utilize intravascular imaging (IVI) to determine such information and may control display 206 to overlay such information on the angiogram imaging data.

Figure 14:
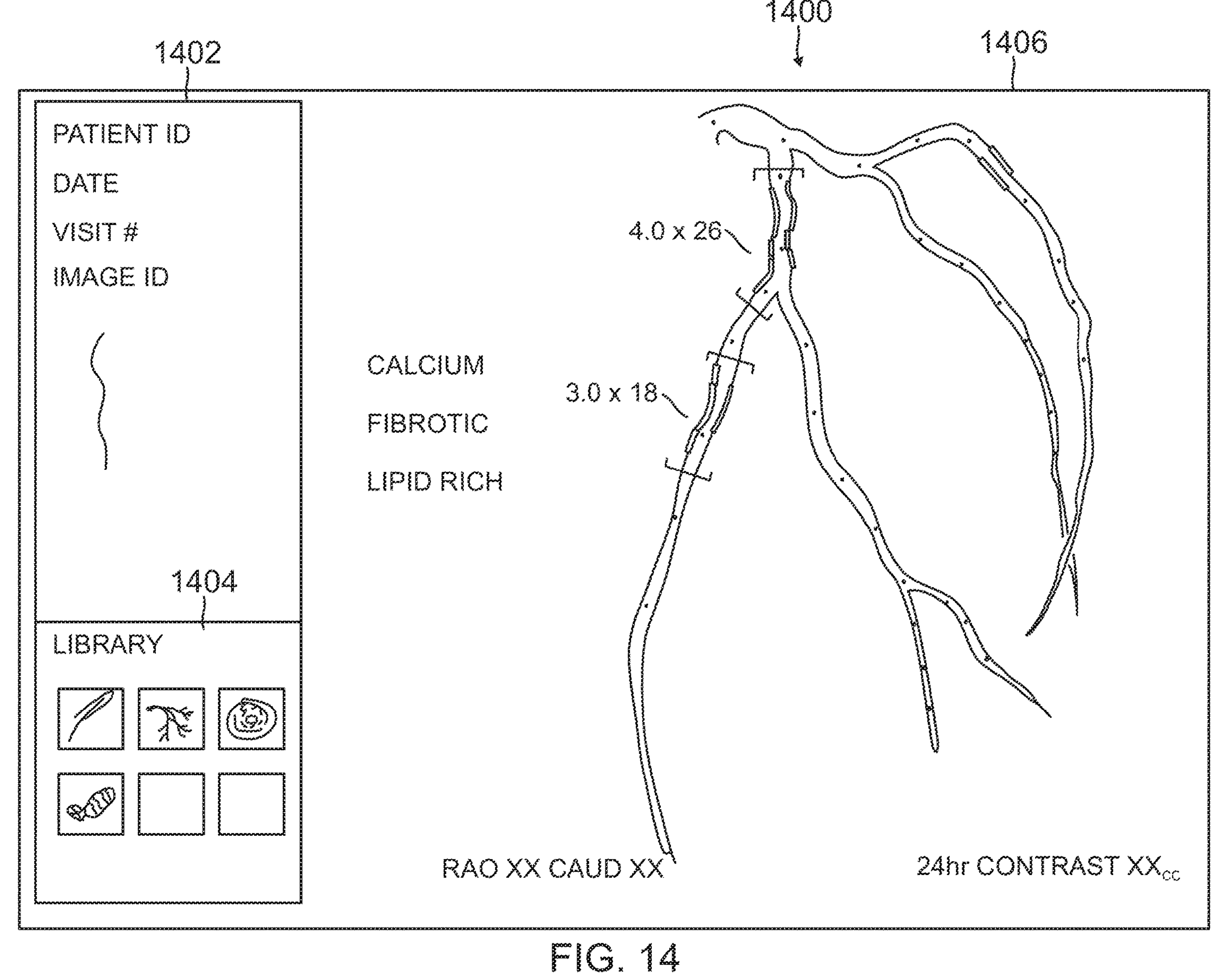
FIG. 14 is a conceptual diagram illustrating another example overlay UI according to one or more aspects of the present disclosure.

FIG. 14 is a conceptual diagram illustrating an example user interface for displaying lesion history according to one or more aspects of this disclosure. Certain aspects of the example of FIG. 14 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

UI 1400 may be a UI of user interface(s) 218 (FIG. 2). Similar to several earlier examples, UI 1400 includes first panel 1402 displaying procedural information and second panel 1404 displaying a library. Main panel 1406 displays information overlaid on angiogram imaging data. Such information may include distance markers and properties of lesions as in main panel 1306 of FIG. 13. Main panel 1406 may further display measurements of lesions (e.g., the displayed brackets). Main panel 1406 may also display suggested landing zones (e.g., via highlighting) and device sizing for stents and/or balloons. For example, processing circuitry 204 may suggest a stent of 4.0 mm in diameter and 26 mm long for an upper lesion and a stent of 3.0 mm in diameter and 18 mm long for a lower lesion via main panel 1406.

Processing circuitry 204 may review dFFR values, lesions to treat, or the like. Processing circuitry 204 may identify and measure lesions of interest and control display 206 to mark and display the lesions of interest, for example, by bracketing, highlighting or the like, overlaid on the angiogram imaging data in main panel 1406. Processing circuitry 204 may determine and control display 206 to display suggested landing zones and/or device sizing for stents or balloons overlaid on the angiogram imaging data in main panel 1406.

Figure 15:
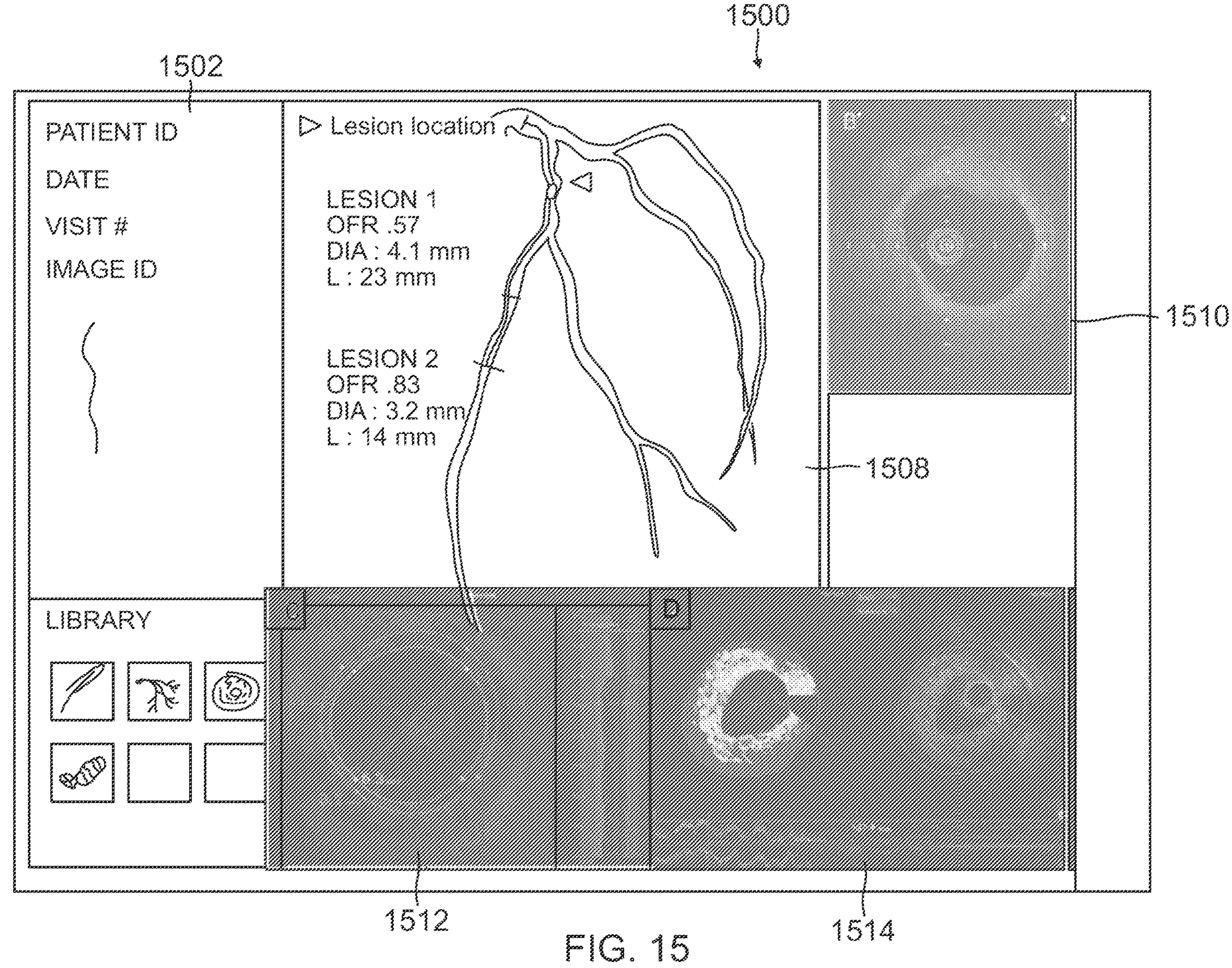
FIG. 15 is a conceptual diagram illustrating another example UI including angiography and other imaging data according to one or more aspects of the present disclosure.

FIG. 15 is a conceptual diagram illustrating an example user interface for displaying imaging data from a plurality of sources according to one or more aspects of this disclosure. Certain aspects of the example of FIG. 15 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

UI 1500 may be a UI of user interface(s) 218 (FIG. 2). Similar to several earlier examples, UI 1500 includes first panel 1502 displaying procedural information and second panel 1504 displaying a library. In the example of FIG. 15, a plurality of other imaging data panels (or sub-panels) are displayed. Processing circuitry 204 may co-register imaging data from each imaging source and/or from each imaging run. For example, processing circuitry 204 may mark where an imaging sensor starts and ends runs. For example, processing circuitry 204 may co-register each of angiogram imaging data shown in panel or sub-panel 1508, imaging data B' in panel or sub-panel 1510, imaging data C in panel or sub-panel 1512, and imaging data D in panel or sub-panel 1514. Processing circuitry 204 may facilitate a clinician to jog back and forth with imaging (e.g., rewind and forward) the imaging data in a coordinated manner such that each image remains co-registered with each other, for example, via input device(s) 210. For example, processing circuitry 204 may integrate multiple imaging modes into a single UI—UI 1500. In some examples, processing circuitry 204 may calculate actual sizes of vessels and control display 206 to display such sizes overlayed on the various imaging data. In some examples, processing circuitry 204 may calculate oFR (e.g., an OCT-based FFR) values and display such oFR values in UI 1500. For example, processing circuitry 204 may display via UI 1500 information relating to lesions, such as for lesion 1 an oFR of 0.57, diameter of 4.1 mm, and length of 23 mm and for lesion 2, an oFR of 0.83, diameter of 3.2 mm, and length of 14 mm.

Figure 16:
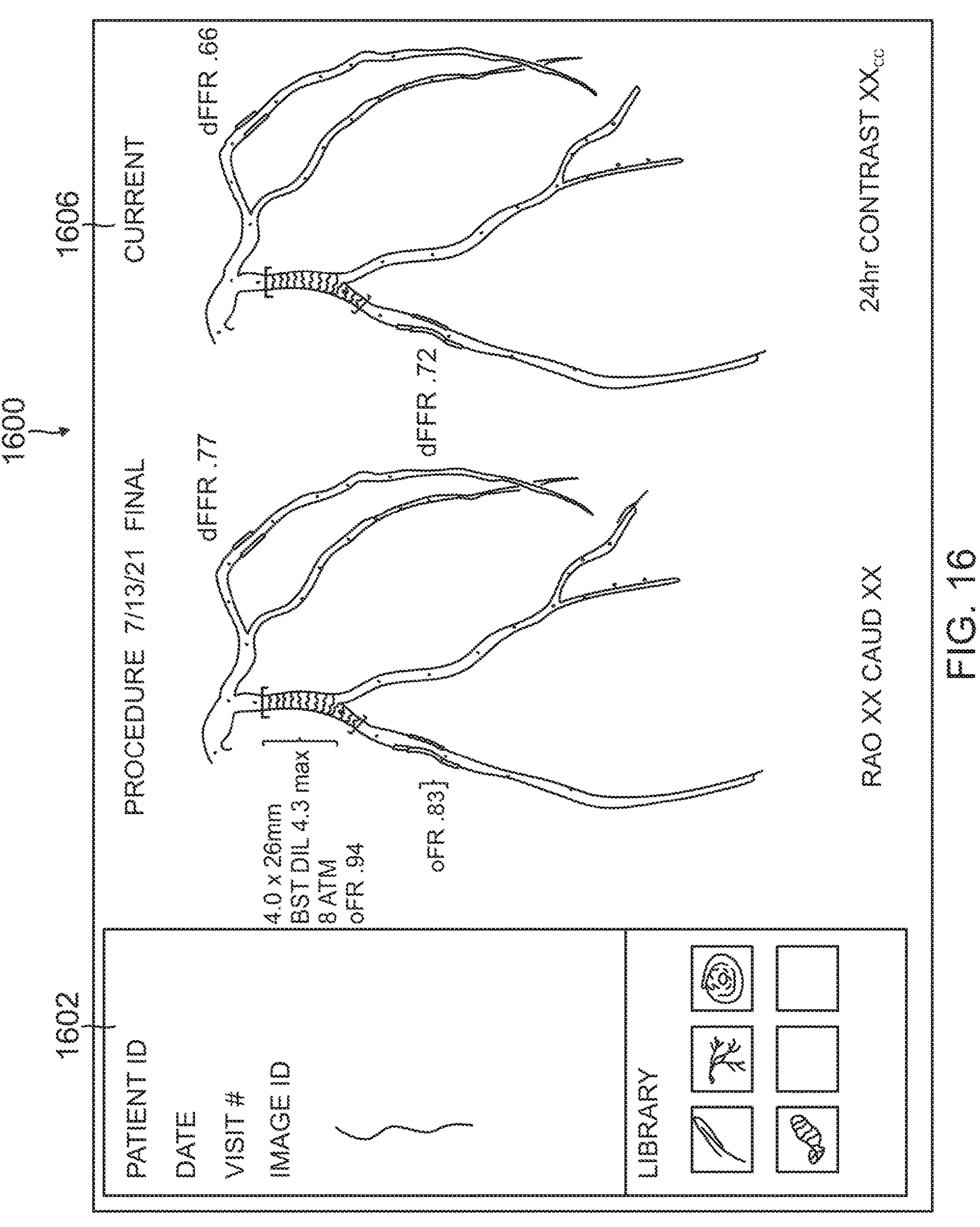
FIG. 16 is a conceptual diagram illustrating an example post-procedure UI according to one or more aspects of the present disclosure.

FIG. 16 is a conceptual diagram illustrating an example user interface to be displayed post procedure according to one or more aspects of this disclosure. Certain aspects of the example of FIG. 16 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

UI 1600 may be a UI of user interface(s) 218 (FIG. 2). Similar to several earlier examples, UI 1600 includes first panel 1602 displaying procedural information and second panel 1604 displaying a library. Main panel 1606 displays information overlaid on angiogram imaging data. In some examples, main panel 1606 displays a final view of one or more previous procedures and a final view of a current procedure. In the case where there is not a previous procedure, mail panel may display the final view of the current procedure. The displayed views may include distance markers and may identify areas which have been treated and parameters associated with such areas and/or properties associated with additional areas that the clinician may be tracking over time. For example, in the angiogram imaging data of the procedure of Jul. 15, 2021, displayed on the left of main panel 1606, a bracketed area is overlaid on the angiogram imaging data of the procedure of Jul. 15, 2021, which was treated. This area shows parameters of 4.0 mm diameter and 26 mm in length with additional properties associated with that area. An area of an upper portion of a right branch of the angiogram imaging data of the procedure of Jul. 15, 2021, is shown as having a dFFR value of 0.77 and an area of a lower portion of a left branch is shown as having an oFR value of 0.83. In the post-procedural view of the current procedure on the right of main panel 1606, the same area of the upper portion of the right branch is shown as narrower than after the previous PCI with a dFFR value of 0.66 and the same area of the lower portion of the left branch is shown as being narrower with a dFFR of 0.72. As such, a clinician may track anatomy of the patient over time to aid the clinician in determining whether further intervention or continued observation is desirable. Processing circuitry 204 may control display 206 to highlight such areas by overlaying highlights on either or both of the previous angiogram imaging data or the current angiogram imaging data so that a clinician may easily identify such areas.

For example, processing circuitry 204 may track stent deployment locations. Processing circuitry 204 may control display 206 to identify any edge dissections, under expansions, malpositions, or the like, with color codes, such as yellow, orange, red, etc. overlaid on the angiogram imaging data. Such color codes may be indicative of a severity of an issue or need for treatment of an issue in the area of the vasculature being color coded. Processing circuitry 204 may determine post PCI dFFR and/or oFR values and control display 206 to display such values overlaid on the angiogram imaging data. In some examples, processing circuitry 204 may compare previous and current procedures and control display 206 to highlight areas of change, for examples, using different color codes, which may be indicative of a severity of a vasculature issue. Processing circuitry 204 may compare myocardial blush grades for microvascular obstruction (MVO) estimations. Myocardial blush may be a visual assessment of myocardial perfusion in a given area. In some examples, processing circuitry 204 may control display 206 to display MVO estimations and/or myocardial blush grades or a representation thereof overlaid on angiogram imaging data.

While a number of examples have been set forth where information, highlights, virtual models, or the like may be overlaid on angiogram imaging data, in some examples, such information, highlights, virtual models, or the like, may be additionally, or alternatively, overlaid on other imaging data or 3D model 306.

Figure 17:
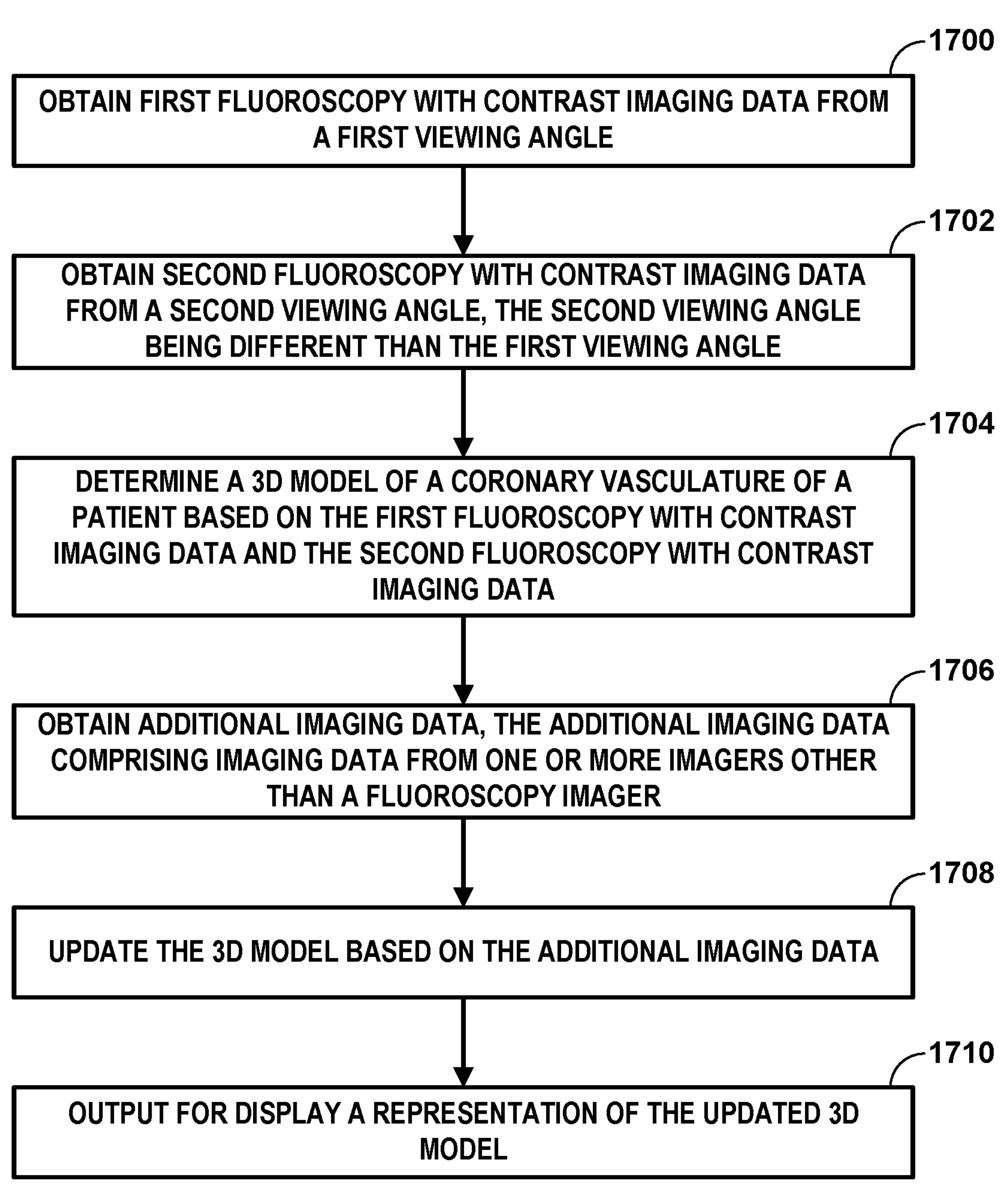
FIG. 17 is a flow diagram illustrating example techniques for 3D modeling of a coronary vasculature of a patient according to one or more aspects of the present disclosure.

FIG. 17 is a flow diagram illustrating example techniques for 3D modeling of a coronary vasculature of a patient according to one or more aspects of the present disclosure. Certain aspects of the example of FIG. 17 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

Processing circuitry 204 may obtain first fluoroscopy with contrast imaging data from a first viewing angle (1700). For example, processing circuitry 204 may receive or extract from imager 140 first fluoroscopy with contrast imaging data from a first viewing angle. For example, imager 140 may have a plurality of sensors arranged at different viewing angles towards a patient and one of those sensors may be oriented at the first viewing angle. Processing circuitry 204 may obtain the first fluoroscopy with contrast imaging data from a first viewing angle from that sensor oriented at the first viewing angle of imager 140. Alternatively, processing circuitry may obtain the first fluoroscopy with contrast imaging data from the first viewing angle by receiving or extracting the fluoroscopy with contrast imaging data at a first time when imager 140 is oriented to capture fluoroscopy with contrast imaging data from the first viewing angle.

Processing circuitry 204 may obtain second fluoroscopy with contrast imaging data from a second viewing angle, the second viewing angle being different than the first viewing angle (1702). For example, processing circuitry 204 may receive or extract from imager 140 second fluoroscopy with contrast imaging data from a second viewing angle. For example, imager 140 may have a plurality of sensors arranged at different viewing angles towards a patient and one of those sensors may be oriented at the second viewing angle. Processing circuitry 204 may obtain the second fluoroscopy with contrast imaging data from a second viewing angle from that sensor oriented at the second viewing angle of imager 140. Alternatively, processing circuitry 204 may obtain the second fluoroscopy with contrast imaging data from the second viewing angle by receiving or extracting the fluoroscopy with contrast imaging data at a second time when imager 140 is oriented to capture fluoroscopy with contrast imaging data from the second viewing angle. In some examples, processing circuitry 204 may obtain one or more further fluoroscopy with contrast imaging data from one or more further viewing angles. For example, processing circuitry may obtain third fluoroscopy with contrast imaging data from a third viewing angle from the sensor oriented at a third viewing angle of imager 140.

Processing circuitry 204 may determine a 3D model of a coronary vasculature of a patient based on the first fluoroscopy with contrast imaging data and the second fluoroscopy with contrast imaging data (1704). For example, the first fluoroscopy with contrast imaging data and the second fluoroscopy with contrast imaging data may be captured from different angles and processing circuitry 204 may employ epipolar geometry (e.g., stereo vision) to determine 3D model 306 of the cardiac vasculature of the patient.

Processing circuitry 204 may obtain additional imaging data, the additional imaging data including imaging data from one or more imagers other than a fluoroscopy imager (1706). For example, processing circuitry 204 may obtain the additional imaging data from one of more of an ultrasound device, a CT device, an IVUS device, an OCT device, a NIRS device, an MRI device, a PET device, or a dielectric-based imaging device. In some examples, the additional imaging data include at least one of CT imaging data, IVUS imaging data, OCT imaging data, NIRS imaging data, ultrasound imaging data, MRI data, or PET imaging data.

Processing circuitry 204 may update the 3D model based on the additional imaging data. In some examples, processing circuitry 204 may co-register at least one of the first fluoroscopy with contrast imaging data, the second fluoroscopy with contrast imaging data, or the 3D model with the additional imaging data. Processing circuitry 204 may output for display the additional imaging data and the at least one of the first fluoroscopy imaging data, the second fluoroscopy imaging data, or the representation of the updated 3D model.

Processing circuitry 204 may output for display a representation of the updated 3D model (1710). For example, processing circuitry 204 may control display 206 to display a representation of the updated 3D model.

In some examples, processing circuitry 204 may identify at least one area of the coronary vasculature of the patient. Processing circuitry 204 may prompt a clinician to utilize additional equipment, the additional equipment being configured to determine additional information relating to the identified at least one area of vasculature of the patient. Processing circuitry 204 may obtain the additional information and update the 3D model based on the additional information.

In some examples, as part of at least one of determining the 3D model or updating the 3D model, processing circuitry 204 may determine at least one of vessel morphology, plaque location, plaque type, vessel length, vessel diameter, FFR scores, lesion dimensions, orientation of one or more lesions with respect to vessel walls, lipid composition, or SYNTAX scores. In some examples, as part of at least one of determining the 3D model or updating the 3D model, processing circuitry 204 may at least one of utilize at least one DICOM file or calibrate at least one measurement off at least one known device measurement reference. In some examples, processing circuitry 204 may update the 3D model during a PCI procedure.

In some examples, processing circuitry 204 may obtain third fluoroscopy with contrast imaging data during a PCI procedure, the third fluoroscopy with contrast imaging data having a lower frame rate than at least one of the first fluoroscopy with contrast imaging data or the second fluoroscopy with contrast imaging data. Processing circuitry 204 may update the 3D model based on the third fluoroscopy with contrast imaging data.

In some examples, processing circuitry 204 may determine a scaled model for each device used during a PCI procedure and output for display a representation of the scaled model for each device used during the PCI procedure. For example, processing circuitry 204 may output for display a representation of the scaled model for each device overlaid or embedded within the 3D model or overlaid on any of the imaging data.

In some examples, as part of at least one of determining the 3D model or updating the 3D model, processing circuitry 204 is configured to execute an artificial intelligence algorithm. In some examples, as part of updating the 3D model, processing circuitry 204 is configured to obtain additional fluoroscopy with contrast imaging data (e.g., from imager 140 and of imaging data 214) and update the 3D model based on the third fluoroscopy with contrast imaging data.

Figure 18:
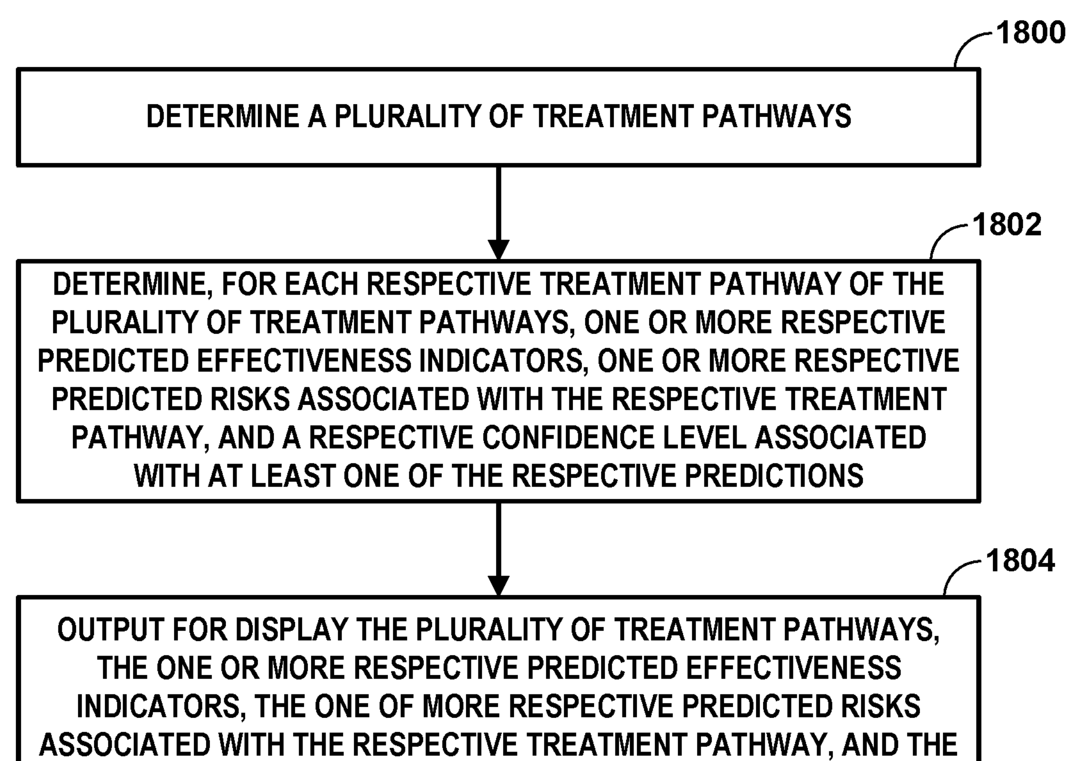
FIG. 18 is a flow diagram illustrating example techniques for virtual procedure modeling according to one or more aspects of the present disclosure.

FIG. 18 is a flow diagram illustrating example techniques for virtual procedure modeling according to one or more aspects of the present disclosure. Certain aspects of the example of FIG. 18 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

Processing circuitry 204 may determine the plurality of treatment pathways (1800). For example, processing circuitry 204 may determine plurality of treatment pathways 404 (FIG. 4), such as medication, angioplasty, stent, atherectomy and stent, and/or CABG.

Processing circuitry 204 may determine, for each respective treatment pathway of the plurality of treatment pathways, one or more respective predicted effectiveness indicators associated with the respective treatment pathway, one or more respective predicted risks associated with the respective treatment pathway, and a respective confidence level associated with at least one of the respective predictions (1802). For example, processing circuitry 204 may determine a predicted FFR value, a predicted QOL value, a predicted 1 month readmission rate and/or a predicted 3 month readmission rate as effectiveness indicators. For example, processing circuitry 204 may determine a predicted risk of complications, such as embolism, and a predicted number of days in bed as predicted risks. For example, processing circuitry 204 may determine a confidence level of each of the predictions, the confidence level of the predicted effectiveness indicators and/or the predicted risks, or an overall confidence level of the predictions associated with a respective treatment pathway.

Processing circuitry 204 may output for display the plurality of treatment pathways, the one or more respective predicted effectiveness indicators associated with the respective treatment pathway, the one or more respective predicted risks associated with the respective treatment pathway, and the respective confidence level associated with at least one of the respective predictions for each respective treatment pathway of the plurality of treatment pathways (1804). For example, processing circuitry 204 may control display 206 to display plurality of treatment pathways 404 and table 402 of FIG. 4.

In some examples, processing circuitry 204 may determine a recommended treatment pathway of the plurality of treatment pathways and output for display an indication of the recommended treatment pathway. In some examples, as part of determining the one or more respective predicted effectiveness indicators associated with the respective treatment pathway, the one or more respective predicted risks associated with the respective treatment pathway, and the respective certainty level associated with at least one of the respective predictions, processing circuitry 204 may execute a machine learning algorithm. In some examples, as part of determining the one or more respective predicted effectiveness indicators associated with the respective treatment pathway, the one or more respective predicted risks associated with the respective treatment pathway, and the respective certainty level associated with at least one of the respective predictions, processing circuitry 204 may generate a 3D model of vasculature of a patient and execute the machine learning algorithm, using input derived from the 3D model of the vasculature of the patient.

In some examples, as part of determining the one or more respective predicted effectiveness indicators associated with the respective treatment pathway, the one or more respective predicted risks associated with the respective treatment pathway, and the respective certainty level associated with at least one of the respective predictions, processing circuitry 204 may run a plurality of simulations.

In some examples, processing circuitry 204 may determine the one or more respective predicted effectiveness indicators associated with the respective treatment pathway based on a device performance prediction. In some examples, the one or more respective predicted effectiveness indicators associated with the respective treatment pathway includes at least one of a respective predicted FFR, a respective predicted quality of life improvement, or at least one respective predicted readmission rate. In some examples, each of the plurality of treatment pathways further includes at least one of a respective inventory availability or cost.

In some examples, in response to clinician input of a selected one of the plurality of treatment pathways, processing circuitry 204 may determine a plurality of treatment options of the selected treatment pathway, each of the plurality of treatment options including one or more respective predicted effectiveness indicators associated with the respective treatment option, one or more respective predicted risks associated with the respective treatment option, a respective confidence level associated with at least one of the respective predictions for the respective treatment option, and suggested device parameters for the respective treatment option. Processing circuitry 204 may output for display the plurality of treatment options of the selected treatment pathway, and the one or more respective predicted effectiveness indicators associated with the respective treatment option, the one or more respective predicted risks associated with the respective treatment option, the respective confidence level associated with at least one of the respective predictions for the respective treatment option, and the suggested device parameters for the respective treatment option.

In some examples, processing circuitry 204 may, during a PCI procedure, determine a live reading, the live reading including one or more live predicted effectiveness indicators associated with the PCI procedure, one or more live risks associated with the PCI procedure, a live certainty level associated with at least one of the respective predictions for the PCI procedure, and live suggested device parameters for the PCI procedure. Processing circuitry 204 may output for display one of the plurality of treatment options and the live reading.

In some examples, processing circuitry 204 may determine at least one of a ghosted preview of the procedure, a graphical predicted FFR, a graphical predicted risk of rupture, or a graphical predicted probability of a successful outcome. Processing circuitry 204 may output for display, during a PCI procedure, at least one of the ghosted preview of the procedure, the graphical predicted FFR, the graphical predicted risk of rupture, or the graphical predicted probability of a successful outcome. For example, processing circuitry 204 may determine the at least one of a ghosted preview of the procedure, a graphical predicted FFR, a graphical predicted risk of rupture, or a graphical predicted probability of a successful outcome via a calculated simulation or via historical clinical data of anatomy, patient data, outcome data, and devices and settings applied previously. In some examples, system 100 may include other graphical processing features such as video stabilization, edge detection, edge enhancement, pixel subtraction, etc.

Figure 19:
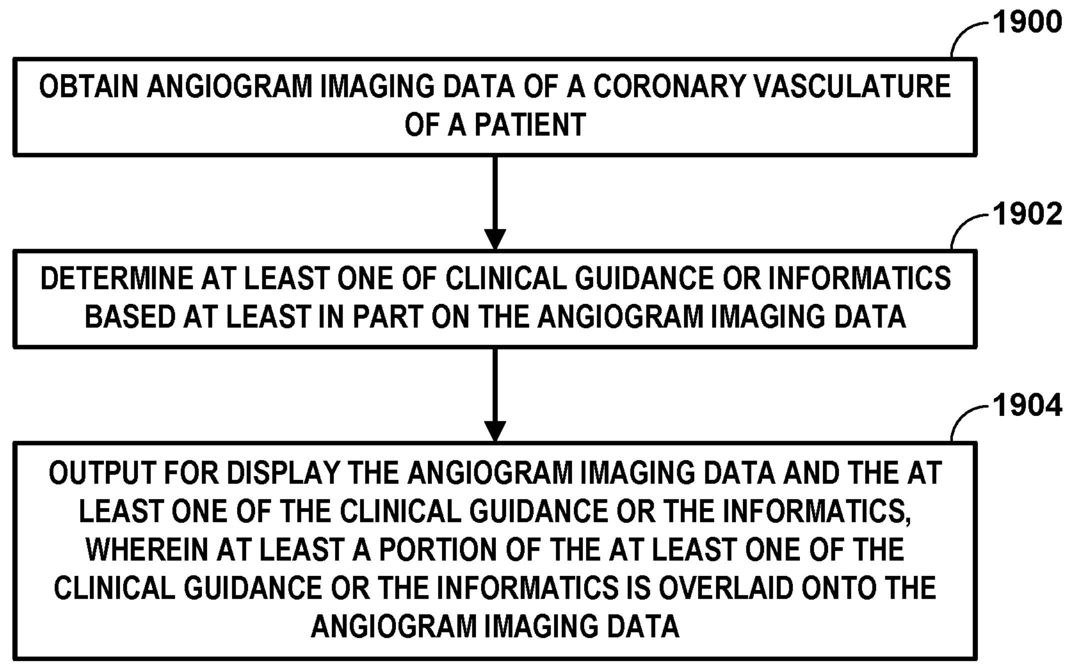
FIG. 19 is a flow diagram illustrating example techniques for presenting angiogram imaging data with other information to a clinician according to one or more aspects of the present disclosure.

FIG. 19 is a flow diagram illustrating example techniques for presenting angiogram imaging data with other information to a clinician according to one or more aspects of the present disclosure. Certain aspects of the example of FIG. 19 are described herein with respect to computing device 200 of FIG. 2 for ease of explanation. It should be noted that the techniques attributed to computing device 200 or components thereof, may be performed by any device of FIG. 1, other devices not shown in FIG. 1 which may be capable of performing such techniques, or any combination thereof.

Processing circuitry 204 may obtain angiogram imaging data of a coronary vasculature of a patient (1900). For example, processing circuitry may extract or receive angiogram imaging data of the coronary vasculature of the patient from imager 140.

Processing circuitry 204 may determine at least one of clinical guidance or informatics based at least in part on the angiogram imaging data (1902). For example, processing circuitry 204 may execute machine learning algorithm(s) 222, artificial intelligence algorithm(s) 226, computer vision algorithm(s) 224, or the like to determine the at least one of the clinical guidance or the informatics.

Processing circuitry 204 may output for display the angiogram imaging data and the at least one of the clinical guidance or the informatics, wherein at least a portion of the at least one of the clinical guidance or the informatics is overlaid onto the angiogram imaging data (1904). For example, processing circuitry 204 may control display 206 to display the angiogram imaging data with at least a portion of the clinical guidance and/or at least a portion of the informatics overlaid onto the angiogram imaging data.

In some examples, the at least a portion of the at least one of the clinical guidance or the informatics includes a heat map, the heat map including at least one ghost image of previous device placements or previous device locations. In some examples, the at least a portion of the at least one of the clinical guidance or the informatics includes procedural guidance for at least one of a bifurcation procedure or a balloon procedure. In some examples, the at least a portion of the at least one of the clinical guidance or the informatics includes at least one of a lesion histology overlay, length markers, or a stent overlay.

In some examples, the at least one of the clinical guidance or the informatics includes at least one suggestion of a device to be used during a clinical procedure, the suggestion including at least one of device type, a device shape, or a device size. In some examples, the at least one of the clinical guidance or the informatics includes instructions for use of a device to be used during a clinical procedure. In some examples, the at least one of the clinical guidance or the informatics includes at least one suggestion of a location to treat, positioning of a device, or device settings.

In some examples, processing circuitry 204 may track one or more locations, in real time, of one or more devices in the coronary vasculature of the patient. The at least a portion of the at least one of the clinical guidance or the informatics may include a representation of the one or more devices at the one or more locations in the coronary vasculature of the patient during a clinical procedure.

In some examples, the at least one of the clinical guidance or the informatics includes at least one of real time feedback during the clinical procedure, wherein the real time feedback includes live risk evaluation of at least one action during the clinical procedure, or at least one prediction based on a device location with respect to specific anatomy of the coronary vasculature of the patient.

In some examples, processing circuitry 204 may track any substances administered. As part of tracking any substances administered, processing circuitry 204 may track a time administered, track a volume administered, and track a type of substance administered. The any substances may include at least one of medication or contrast.

In some examples, processing circuitry 204 may determine an amount of radiation the patient has been exposed to in a predetermined time period. Processing circuitry 204 may determine a first amount of contrast for imaging. Processing circuitry 204 may automatically control an injection device to inject a second amount of contrast based on the determined amount of radiation the patient has been exposed to in the predetermined time period and the determined first amount of contrast.

In some examples, the at least one of the clinical guidance or the informatics includes one or more recommendations of positioning, based on a first angiogram of the angiogram imaging data, of imaging equipment, for generation of additional imaging data. In some examples, the at least one of the clinical guidance or the informatics includes one or more recommendations of a procedure to be performed. In some examples, the at least one of the clinical guidance or the informatics includes one or more real time suggestions on one or more devices to be used during the procedure. In some examples, the at least one of the clinical guidance or the informatics includes a comparison of predicted outcomes of at least two potential procedures. In some examples, the at least one of the clinical guidance or the informatics includes personalized guidance based on a clinician to be performing a procedure. In some examples, the at least one of the clinical guidance or the informatics includes one or more lesion preparation strategies.

In some examples, the at least a portion of the at least one of the clinical guidance or the informatics includes at least one pop-up box, the at least one pop-up box identifying at least one of a vessel, calcium, or a previously implanted stent. In some examples, the at least one of the clinical guidance or the informatics includes real time auto-identified plaque morphology and the at least a portion of the at least one of the clinical guidance or the informatics includes a highlighted vessel vulnerability. In some examples, the at least one of the clinical guidance or the informatics includes additional information co-registered with the angiogram imaging data, the additional information including at least one of IVUS imaging data, OCT imaging data, one or more FFR values, or NIRS imaging data.

In some examples, processing circuitry 204 may output for display information from a previous procedure of the patient and information from a current procedure. The information from the current procedure may include highlighted changes in the coronary vasculature of the patient from the previous procedure to the current procedure. Processing circuitry 204 may determine a nature of a lesion based at least in part on at least one of the changes in the coronary vasculature of the patient or the angiogram imaging data.

In some examples, processing circuitry 204 may allow a user to recall for display similar case scenarios and review relevant case information from the similar case scenarios, including anatomical data, device data, procedure data, outcome data, etc. Similar cases may be identified via one or more of ML algorithm(s) 222, AI algorithm(s) 226, and/or computer vision algorithm(s) 224, which may be trained to compare features and identify critical features to determine similarity.

The system may also allow users to specify what key features they want to use in this search for similar cases (e.g., a user may request cases in which a rotational atherectomy was performed on a bend with a similar bend radius to the one they are currently viewing).

Figure 20:
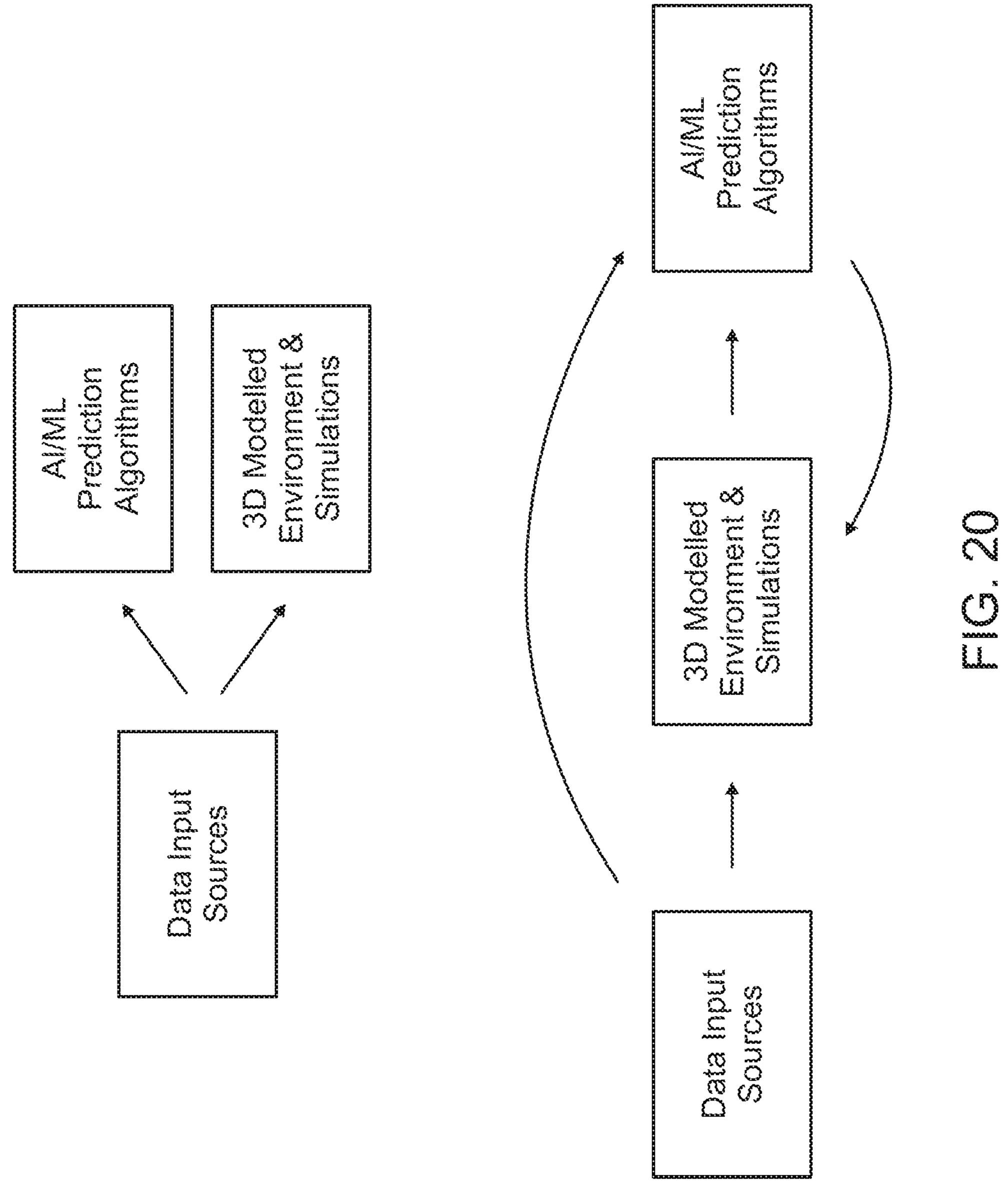
FIG. 20 is a flow diagram illustrating example uses of a 3D model according to one or more aspects of this disclosure.

FIG. 20 is a flow diagram illustrating example uses of a 3D model according to one or more aspects of this disclosure. For example, processing circuitry 204 may use 3D model 232, for example, by feeding 3D model 232 into a computational model for a procedure and/or outcome simulation or to train one or more of ML algorithm(s) 222, AI algorithm(s) 226, and/or computer vision algorithm(s) 224 to predict outcomes and/or risks. In some examples, processing circuitry 204 may use clinical procedure and/or patient outcome data to train to train one or more of ML algorithm(s) 222, AI algorithm(s) 226, and/or computer vision algorithm(s) 224.

Figure 21:
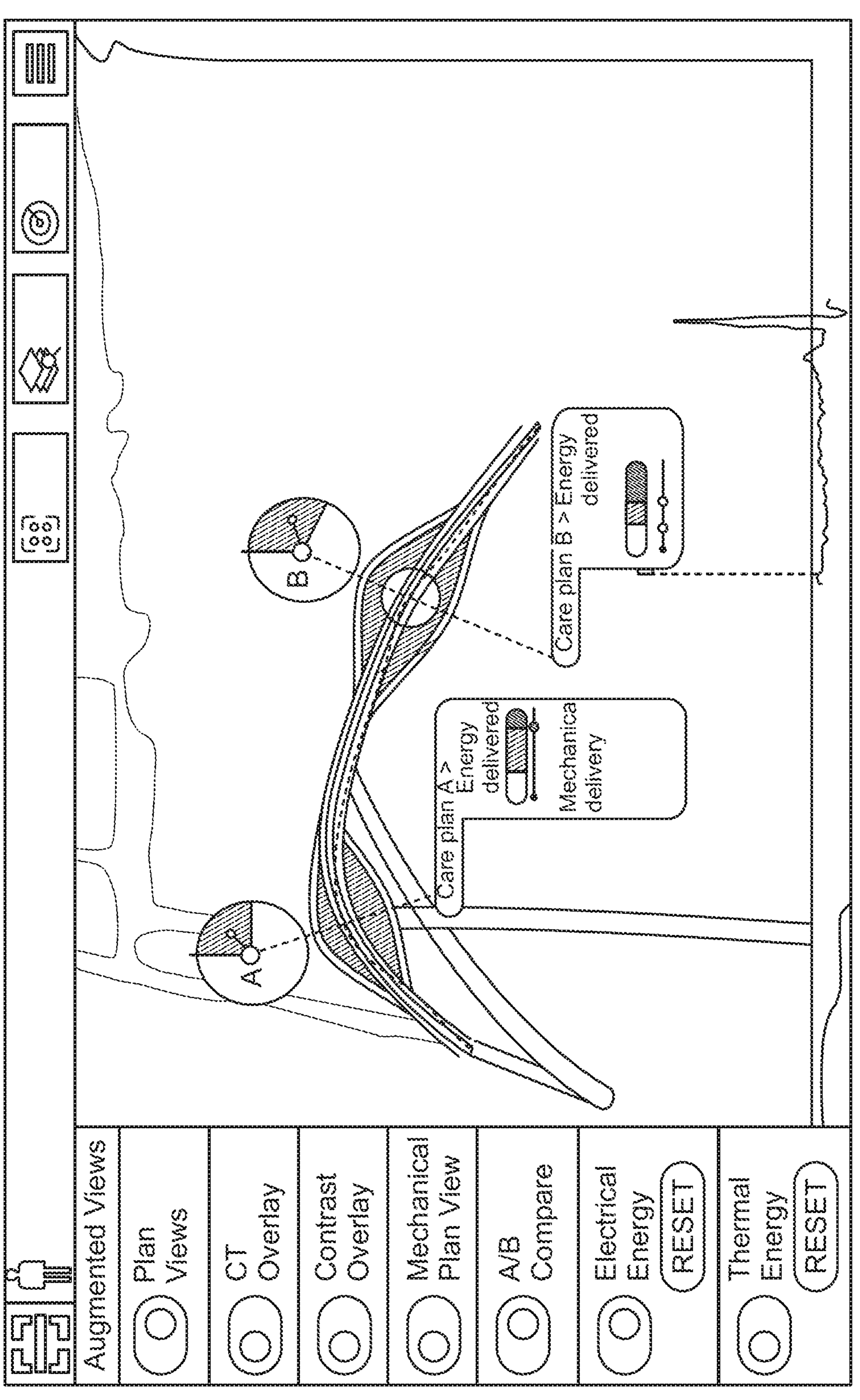
FIG. 21 is a conceptual diagram illustrating an example graphical overlay over an angiography image according to one or more aspects of this disclosure.

FIG. 21 is a conceptual diagram illustrating an example graphical overlay over an angiography image according to one or more aspects of this disclosure. For example, processing circuitry 204 may control display 206 to display a graphical overlay over the angiography screen (or a similar display) which graphically displays the energy characteristics delivered to a physical location as shown in the example of FIG. 21 or similar informational characteristics such as graphically highlighting key locations and anatomical and/or device features.

Figure 22:
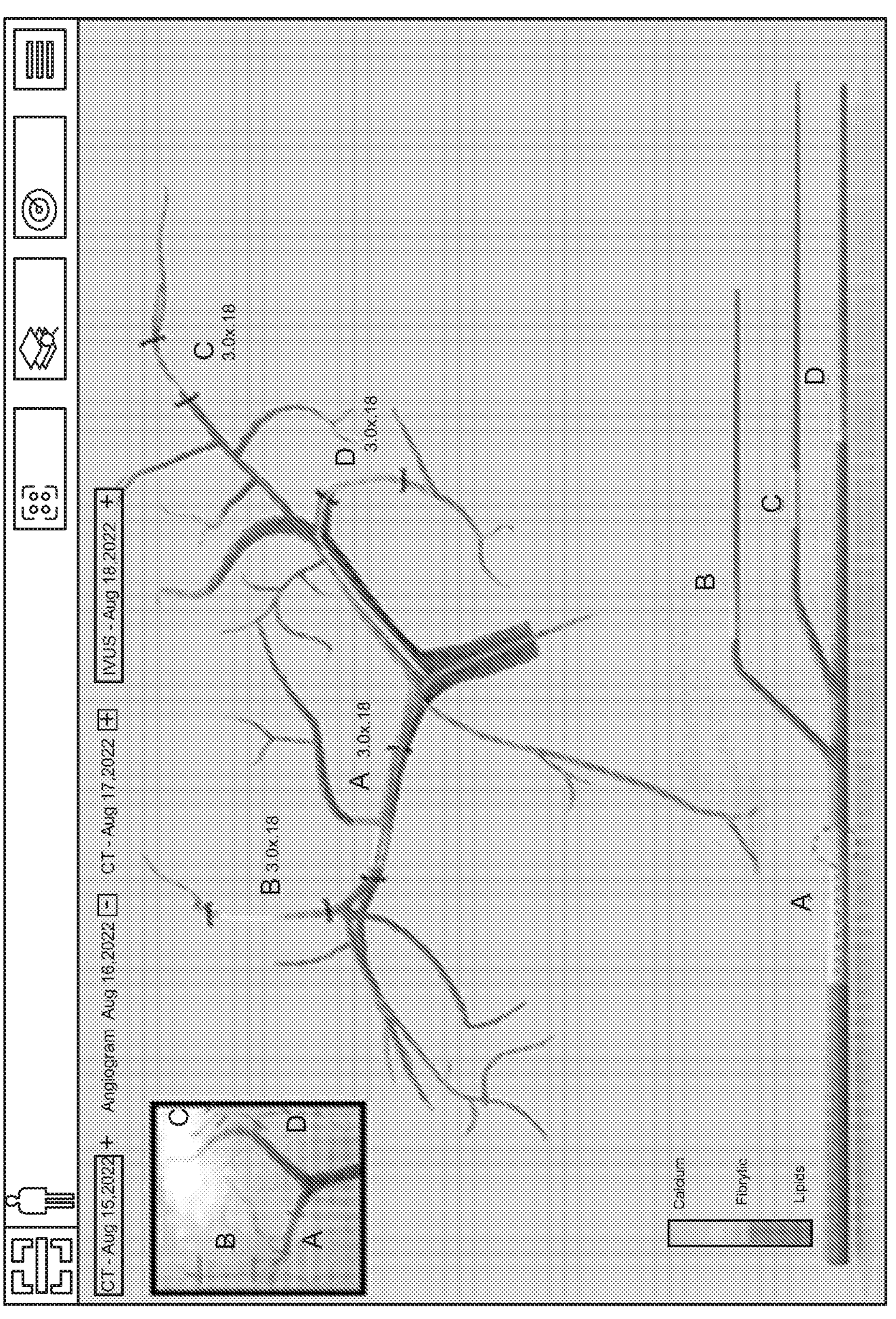
FIG. 22 is a conceptual diagram illustrating an example graphical overlay over an illustration based on an angiography image according to one or more aspects of this disclosure.

FIG. 22 is a conceptual diagram illustrating an example graphical overlay over an illustration based on an angiography image according to one or more aspects of this disclosure. For example, processing circuitry 204 may transform an angiogram imaging data into an analogous illustration (a computer graphics illustration) such as shown in the example of FIG. 22 and overlay additional information on the illustration.

Figure 23:
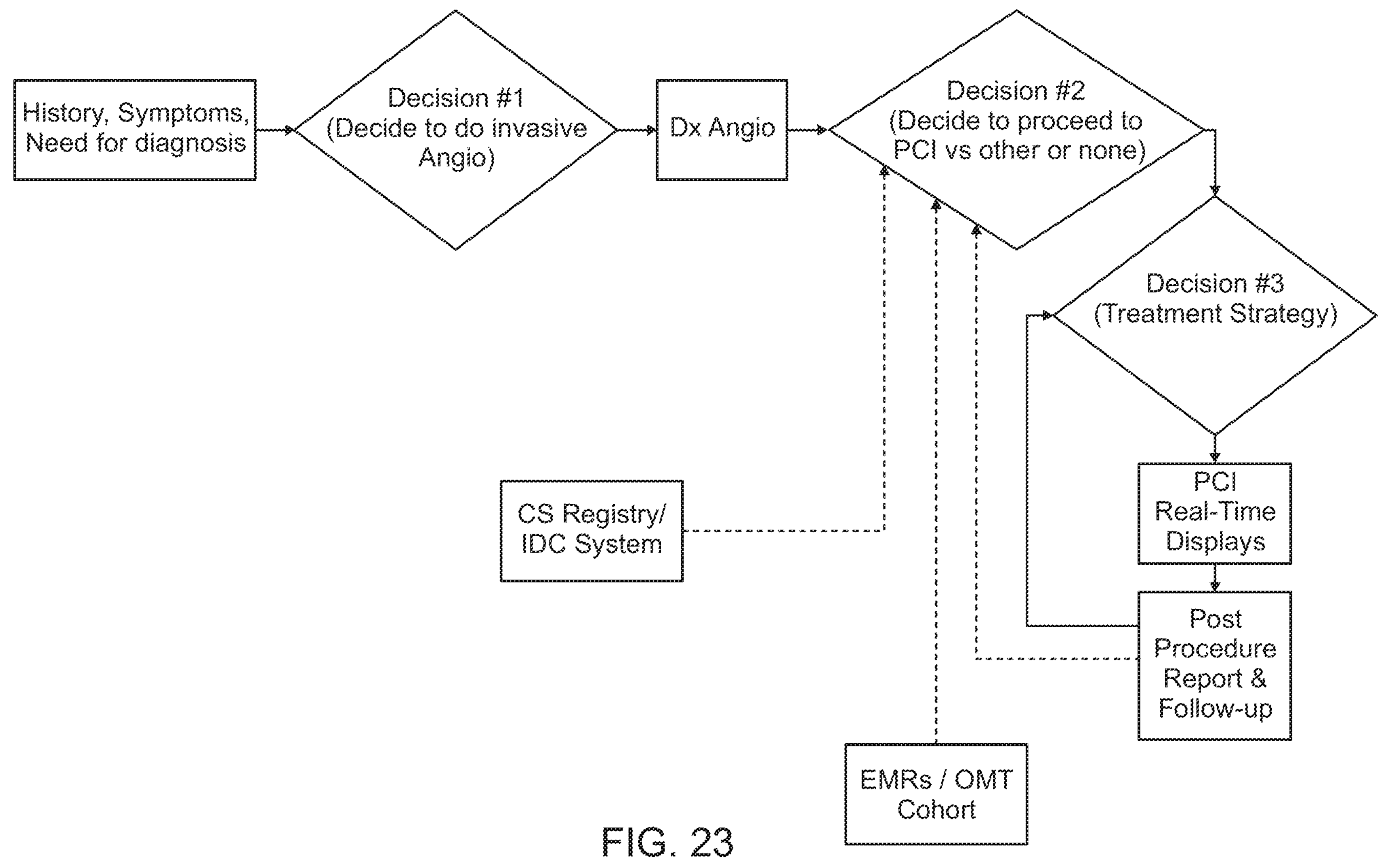
FIG. 23 is a flow diagram illustrating example techniques of this disclosure according to one or more aspects of this disclosure.

FIG. 23 is a flow diagram illustrating example techniques of this disclosure according to one or more aspects of this disclosure.

FIG. 24 is a conceptual diagram illustrating example device recommendation techniques according to one or more aspects of this disclosure. For example, processing circuitry 204 may recommend one or more guide catheters to use for one or more medical procedures. For example, based on angiogram imaging data, a vascular approach (femoral, right radial, left radial), and a target vessel to canulate (left main, right coronary, SVG, etc.), processing circuitry 204 may recommend one or more most suitable curve shapes of one or more guide catheter(s). In some examples, processing circuitry 204 may control display 206 to overlay such curve shapes on the angiogram imaging data to display to a clinician how such shapes might sit and interact with the vessel ostium and aorta's vessel wall.

Processing circuitry 204 may recommend one or more tool types for the medical procedure. For example, processing circuitry 204 may, based on one or more angiogram imaging data and/or additional imaging data, assess a lesion type (e.g., calcific, fibrotic, lipidic). For example, processing circuitry 204 may use angiogram imaging data and IVUS and/or OCT imaging data to assess the lesion type.

For example, if the lesion is fibrotic, processing circuitry 204 may recommend direct stenting. If the lesion is lipidic, processing circuitry 204 may suggest using a compliant balloon. If the lesion is mild or moderately calcific, processing circuitry 204 may recommend starting with a non-compliant balloon or IVL. If the lesion is severely calcific, processing circuitry 204 may recommend using atherectomy or IVL.

Processing circuitry 204 may recommend balloon and/or stents sizing. For example, based one or more angiogram imaging data and/or additional imaging data, processing circuitry 204 may determine lesion length and/or vessel diameter. Processing circuitry 204 may, based on the determined lesion length and/or vessel diameter, recommend balloon sizing and/or stent sizing.

Processing circuitry 204 may recommend rotational atherectomy/burr size. For example, processing circuitry 204 may determine that a lesion is calcific enough for rotational atherectomy, suggest a burr size based on healthy vessel lumen diameter, stenosed lumen diameter, and/or relevant ratios (e.g., burr to lumen diameter ratio~0.7).

Figure 25:
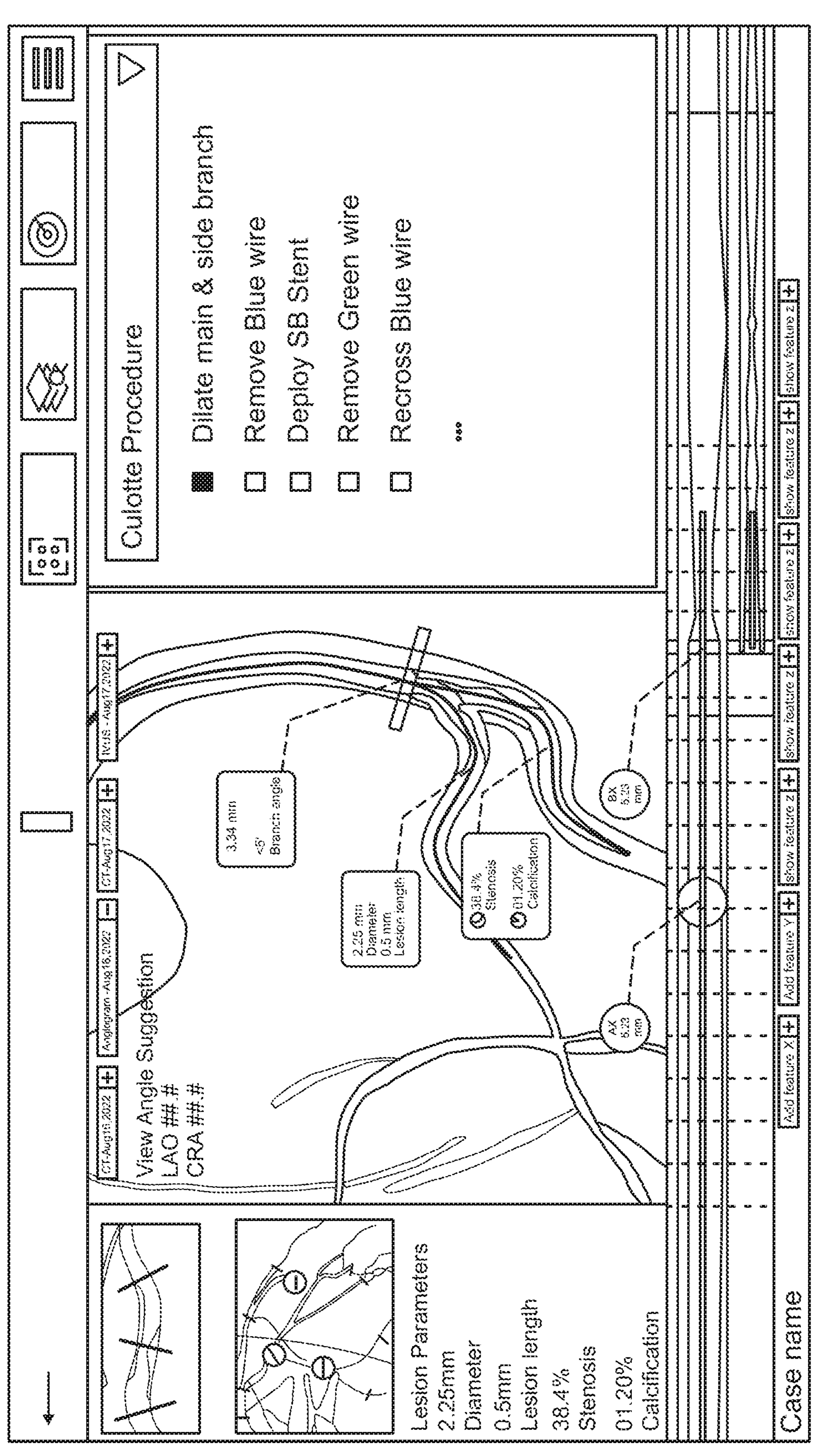
FIG. 25 is a conceptual diagram illustrating an example of bifurcation guidance according to one or more aspects of this disclosure.

FIG. 25 is a conceptual diagram illustrating an example of bifurcation guidance according to one or more aspects of this disclosure. Processing circuitry 204 may merge data from multiple data sources onto one screen (e.g., CT data, angiogram projections (e.g., angiogram imaging data plus overlaid data), IVUS imaging data, etc.). For example, processing circuitry 204 may control display 206 to display merged data from multiple data sources.

Processing circuitry 204 may use a plurality of fluoroscopy with contrast data (e.g., captured from different angles), additional imaging data from at least one source (e.g., of additional imager(s) 142) other than a fluoroscopy device (e.g., imager 140), and/or data obtained from other source(s) to map actual vessel geometry and to generate 3D model 232 (or 3D model 306). Processing circuitry 204 may control display 206 to display 3D model 232 (or 3D model 306) as described herein.

Processing circuitry 204 may perform a quantitative coronary analysis (QCA), for example, using any of the algorithm(s), simulations, or the like discussed herein. In some examples, processing circuitry may overlay labels on angiogram imaging data, such as a label for a side branch, a main branch, a proximal branch, or the like. The labels may include information relating to the respective branch, such as vessel size, side branch lesion length, % stenosis, calcification, angulation, or the like, which processing circuitry 204 may use to determine a MEDINA score, which display 206 may also display.

In some examples, processing circuitry 204 may control display 206 to display a representation of a navigation-enabled guide catheter tip and alignment of the navigation-enabled guide catheter tip with the ostia. In some examples, display 206 may display such information in a 3D manner, as discussed herein. In some examples, processing circuitry 204 may color code one or more representations displayed on display 206. For example, different wires may be color coded differently. For example, a wire in the main branch may be represented in a different color than a wire in a side branch. Processing circuitry 204 may also control display 206 to display graphical representations of certain data, for example, as shown.

Processing circuitry 204 may control display to display a set of clinician selectable values for facilitating clinician input to any clinical guidance and/or informatics processing circuitry 204 may provide via display 206 and/or for training any of ML algorithm(s) 222, AI algorithm(s) 226, and/or computer vision algorithm(s) 224. Such set of clinician selectable values may include values assignable to various attributes of the clinical guidance and/or informatics. In the example of FIG. 25, processing circuitry may control display 206 to display a plurality of selectable values for the attributes: clinical value, workflow value, economic value, and overall concept. A clinician may select any of the displayed values for each attribute, for example, to rate the displayed clinical guidance and/or informatics.

Figure 26:
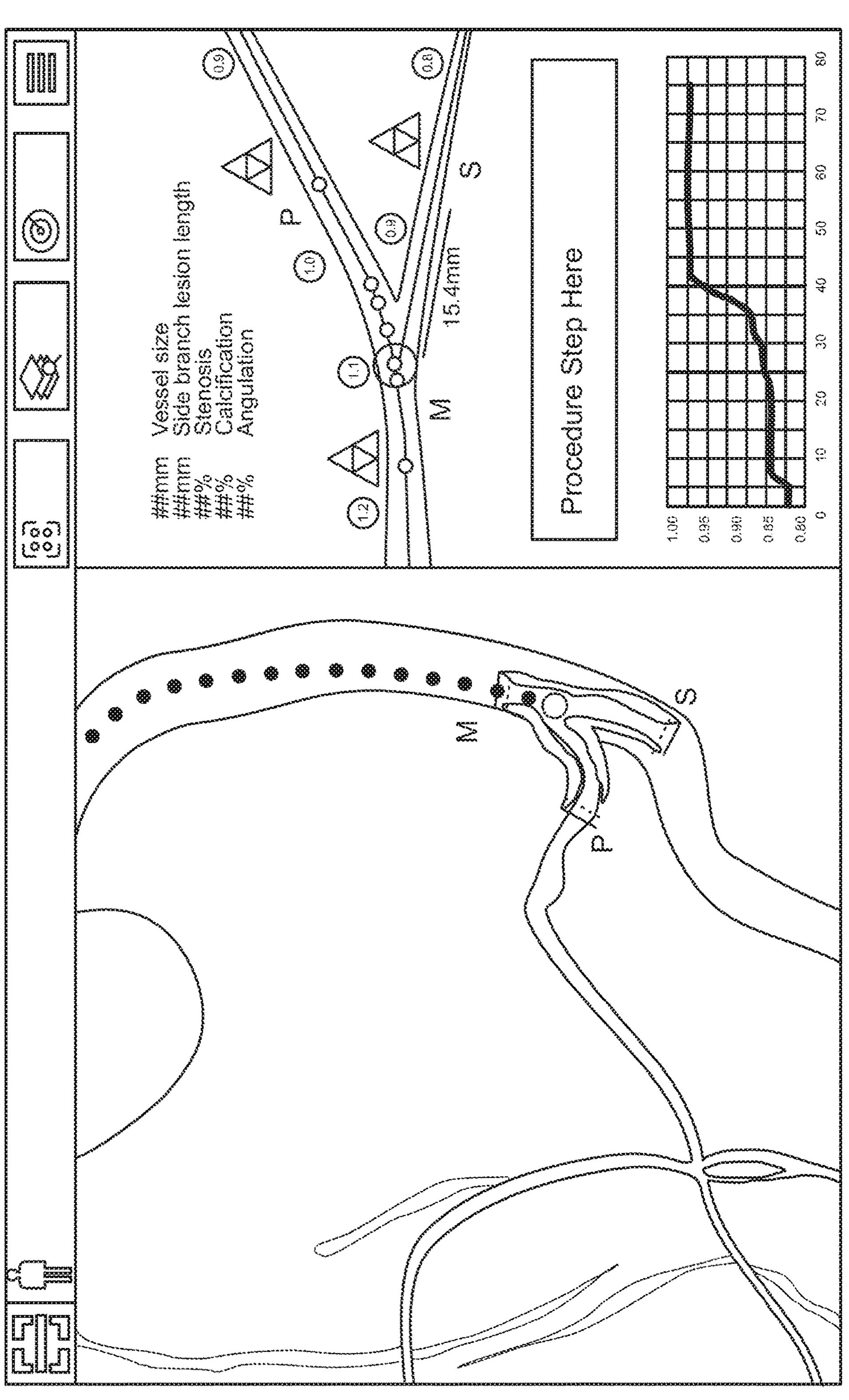
FIG. 26 is a conceptual diagram illustrating another example of bifurcation guidance according to one or more aspects of this disclosure.

FIG. 26 is a conceptual diagram illustrating another example of bifurcation guidance according to one or more aspects of this disclosure. In some examples, rather than control display 206 to display bifurcation guidance as in the example of FIG. 25, processing circuitry 204 may control display 206 to display bifurcation guidance as in the example of FIG. 26. In this example, like in the example of FIG. 25, processing circuitry 204 may also control display 206 to display graphical representations of certain data, for example, as shown.

FIG. 27 is a conceptual diagram illustrating an example chronic total occlusion (CTO) dashboard according to one or more aspects of this disclosure. In the example of FIG. 27, processing circuitry 204 may merge data from multiple data sources onto one screen. For example, display 206 may CT imaging data, and multiple angiogram projections (e.g., angiogram imaging data plus overlaid data). For example, processing circuitry 204 may control display 206 to display merged data from multiple data sources.

Processing circuitry 204 may use a plurality of fluoroscopy with contrast data (e.g., captured from different angles), additional imaging data from at least one source (e.g., of additional imager(s) 142) other than a fluoroscopy device (e.g., imager 140), and/or data obtained from other source(s) to map actual vessel geometry and to generate 3D model 232 (or 3D model 306). Processing circuitry 204 may control display 206 to display 3D model 232 (or 3D model 306) as described herein.

Processing circuitry 204 may determine measurements, such as entry shape, length, angulation, calcification, etc., e.g., from 3D model 232 (or 3D model 306), imaging data, and/or data obtained from other sources, and automatically calculate a CTO score (e.g., a J-CTO score, a CT-RECTOR score, or the like. Processing circuitry 204 may control display 206 to display the CTO score and/or other information.

In some examples, processing circuitry 204 may recommend a go or no-go recanalization strategy. For example, processing circuitry 204 may recommend a recanalization procedure and/or strategy or may recommend not pursuing a recanalization procedure and/or strategy. Such recommendations may be based on 3D model 232 (or 3D model 306), obtained imaging data and/or data obtained from other devices.

In examples where processing circuitry 204 recommends a recanalization, processing circuitry 204 determine which recanalization strategies (e.g., antegrade, retrograde) have the highest predicted success rate for the current CTO score, recommend the recanalization strategy with the highest predicted success rate and present, via display 206, a representation and/or a recommendation of the recanalization strategy having the highest predicted success rate. In some examples, processing circuitry 204 may also present back-up strategies having relatively high predicted success rates. In some examples, processing circuitry 204 may recommend recanalization strategies other based on, or based solely on the predicted success rate. For example, processing circuitry 204 may base recommendations, in whole or in part, on predicted risks, or other factors, such as other factors discussed herein.

In some examples, processing circuitry 204 may provide a “stop and end” warning to a clinician via display 206 and/or output device(s) 212 after “X.” X may be a time, radiation exposure, contrast amount, a predetermined number of failed attempts, or the like.

Figure 28:
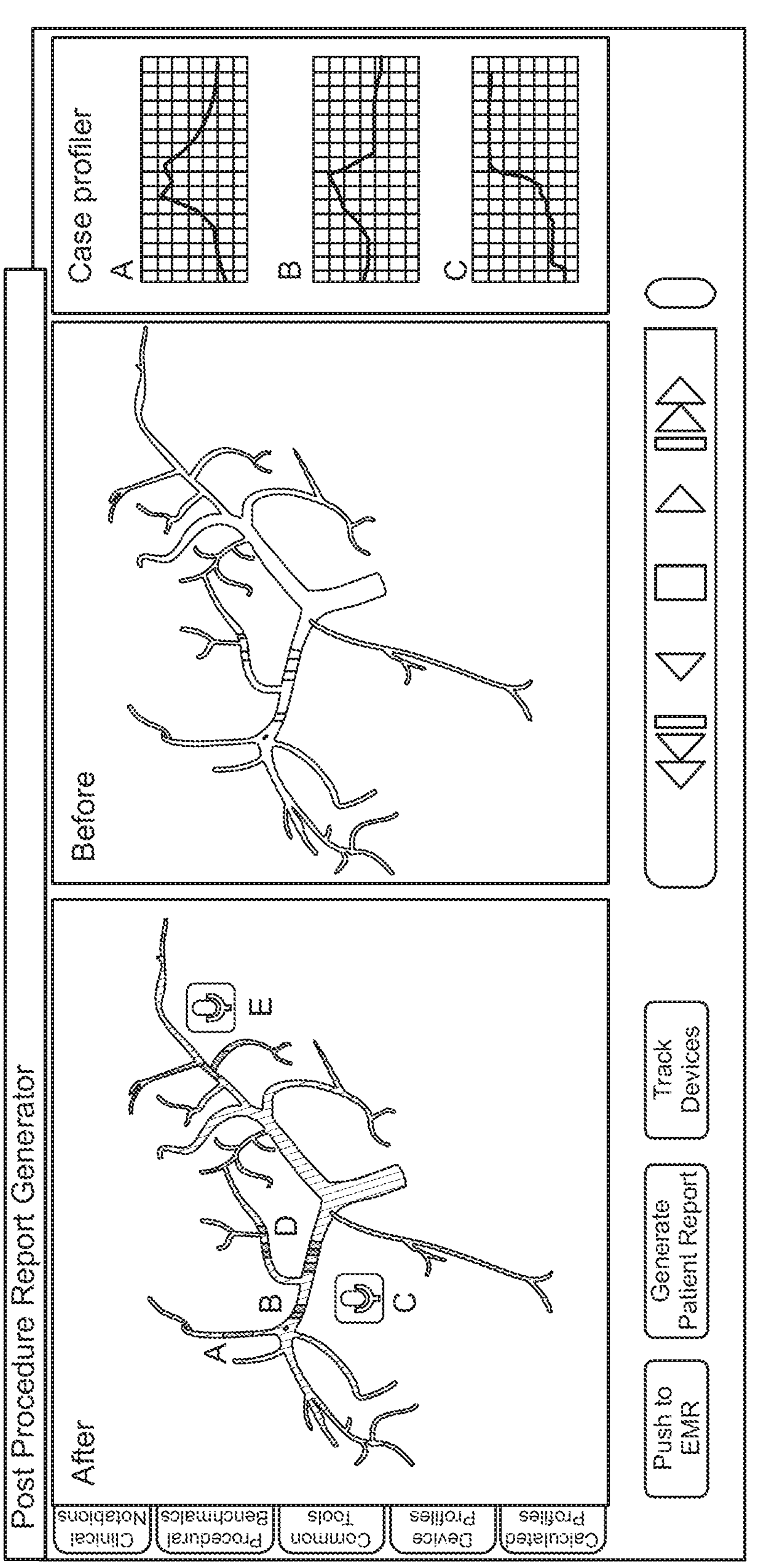
FIG. 28 is a conceptual diagram illustrating an example post procedure report according to one or more aspects of this disclosure.

FIG. 28 is a conceptual diagram illustrating an example post procedure report according to one or more aspects of this disclosure. For example, processing circuitry 204 may automatically generate a post procedure report (or portions thereof) (e.g., electronic patient record 236) from data captured during the procedure (and in some cases, data captured prior to the procedure such as from a diagnostic angiogram). Processing circuitry 204 may annotate the post procedure report to include live dictation which may be captured by one or more microphones, e.g., of input device(s) 210.

For example, in generating electronic patient record 236, processing circuitry 204 may compare pre-procedure data and post-procedure results in a simple summary. Processing circuitry 204 may calculate or otherwise quantify new metrics which may have previously been assessed only subjectively. Processing circuitry 204 may benchmark and/or compare the current procedure to similar cases. Processing circuitry 204 may include an inventory of devices used and/or devices preferred for similar cases in the future. Processing circuitry 204 may also generate a modified versions of electronic patient record 236 (e.g., a less detailed version), the patient, and/or a referring clinician. In some examples, processing circuitry 204 may, during the medical procedure, track complications in real time and include any such complications in electronic patient record 236.

Figure 29:
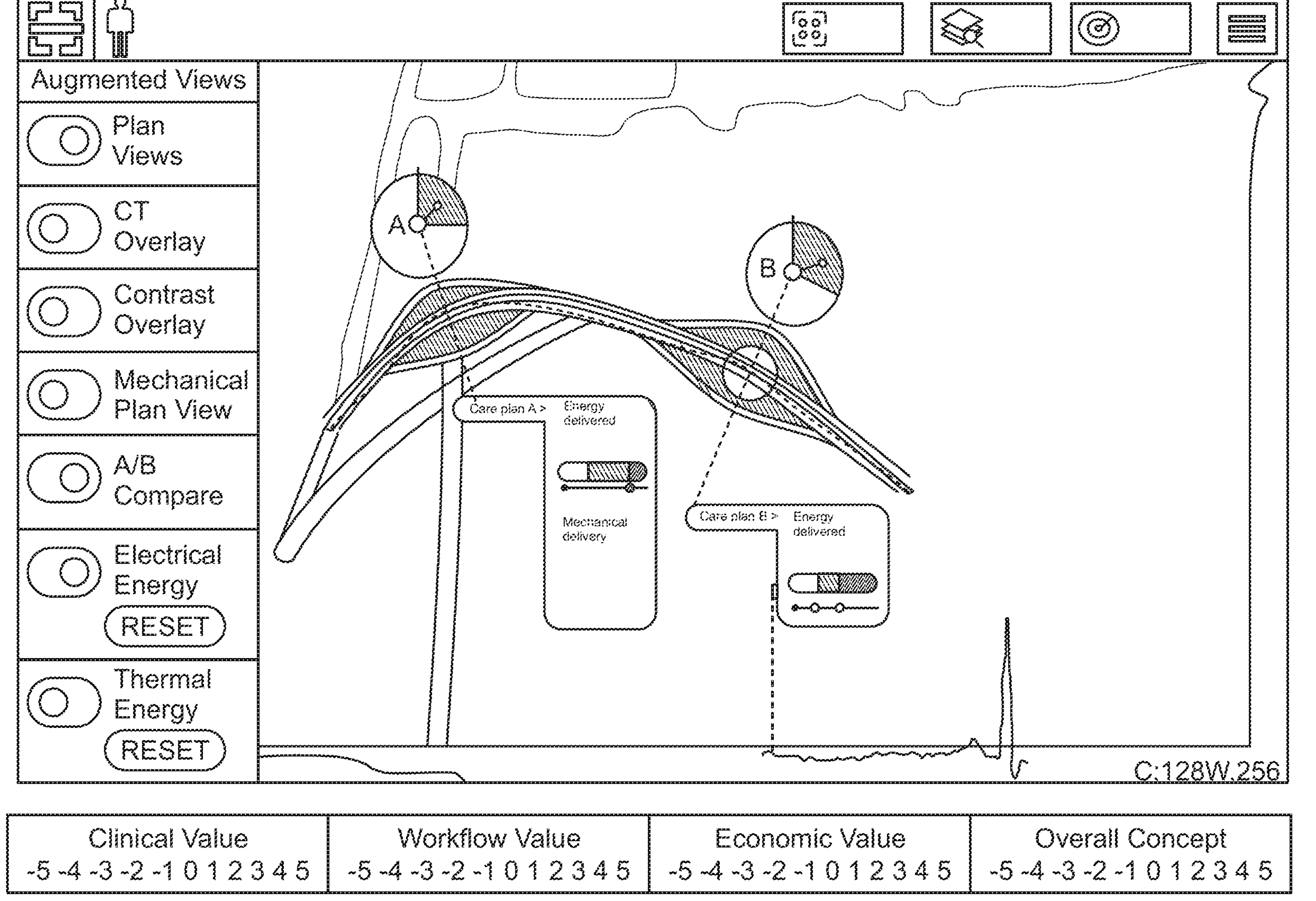
FIG. 29 is a conceptual diagram illustrating an example overlay of real time data on angiogram imaging data according to one or more aspects of this disclosure.

FIG. 29 is a conceptual diagram illustrating an example overlay of real time data on angiogram imaging data according to one or more aspects of this disclosure. Processing circuitry 204 may, in real time, track device deployments with enhanced visuals. For example, processing circuitry 204 may determine and control display 206 to display a heatmap indicative of time spent at a particular location for a given device (for example, a balloon deployment, or ablation run). For example, processing circuitry 204 may use different colors to indicate different lengths of time in such a heatmap.

Figure 30:
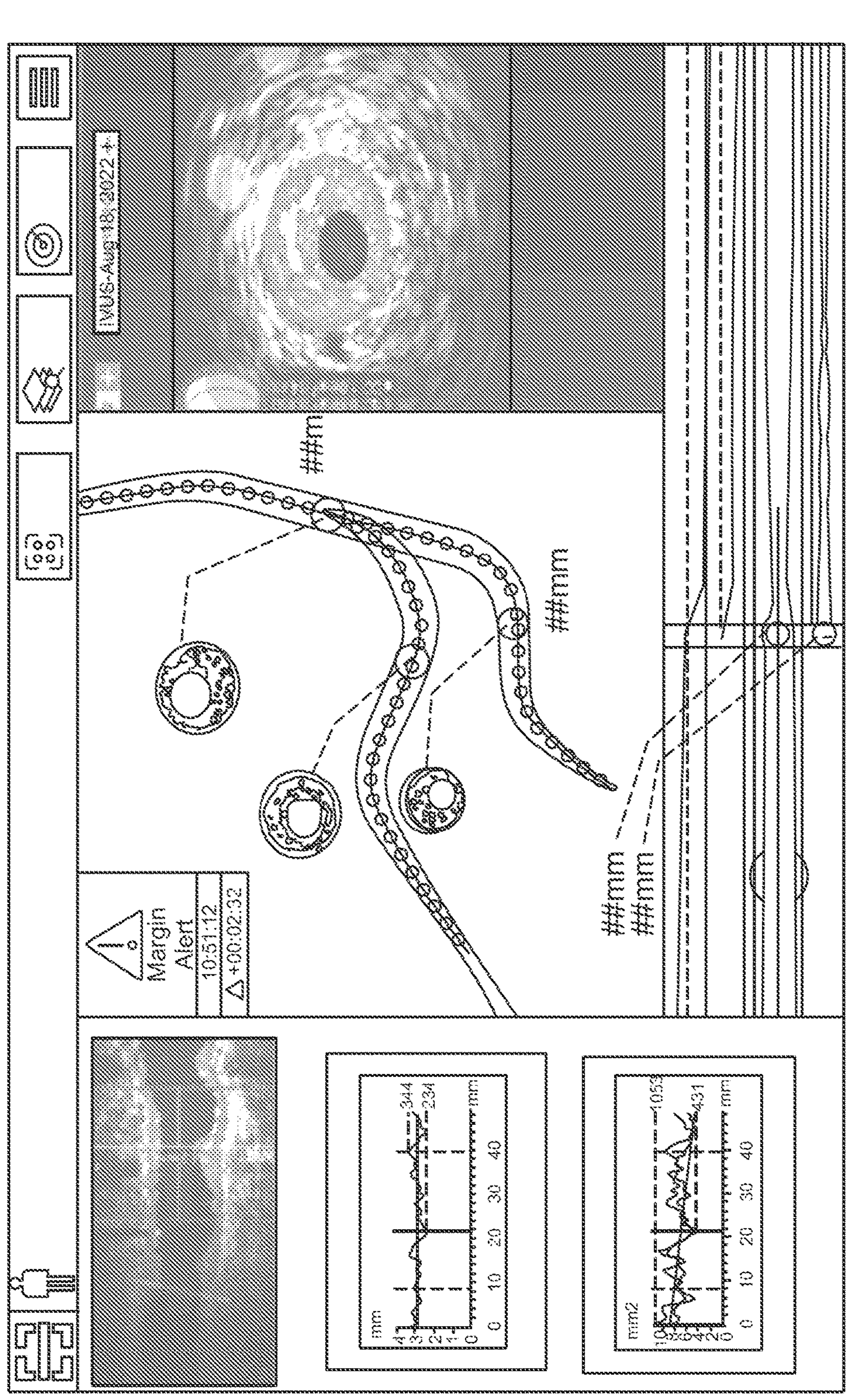
FIG. 30 is a conceptual diagram illustrating another example overlay of real time data on angiogram imaging data according to one or more aspects of this disclosure.

FIG. 30 is a conceptual diagram illustrating another example overlay of real time data on angiogram imaging data according to one or more aspects of this disclosure. For example, processing circuitry 204 may control display 206 and/or output device(s) 212 to provide visual and/or audible alerts of key events during a medical procedure. Such key events may include a dissection detection and/or other complications, device notes, device issues, or the like. In some examples, processing circuitry 204 may control display 206 to display diameters, lengths, or other dimensions (e.g., of vasculature, lesions, devices, and/or the like) overlaid on angiogram imaging data. Processing circuitry 204 may also co-register virtual FFR pullback with the angiogram imaging data and control display 206 to display the virtual FFR pullback with the angiogram imaging data. For example, display 206 may display lesion morphology, identify devices (such as guide catheters and/or other devices disclosed herein) with the angiogram imaging data.

Figure 31:
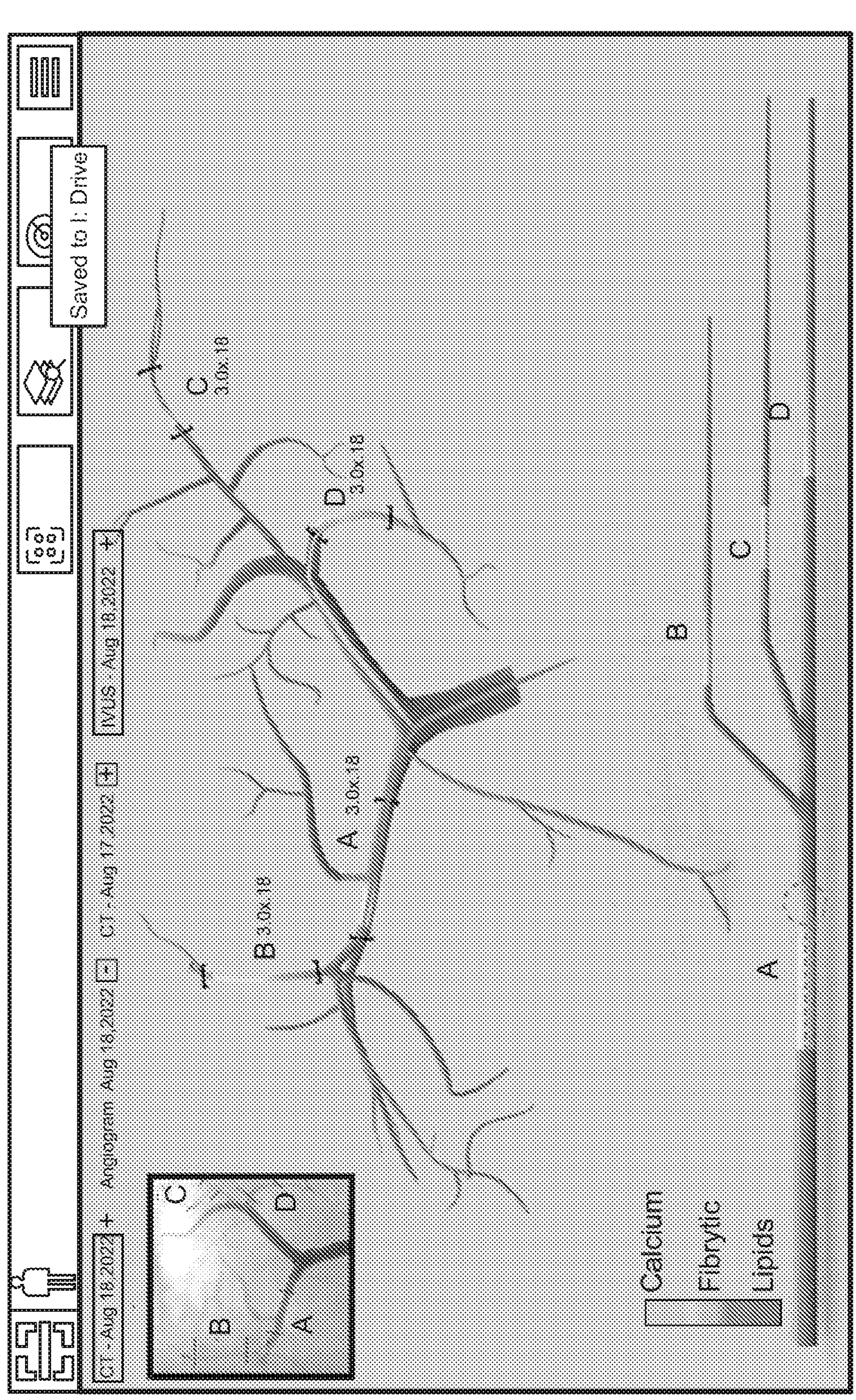
FIG. 31 is a conceptual diagram illustrating yet another example overlay of real time data on angiogram imaging data according to one or more aspects of this disclosure.

FIG. 31 is a conceptual diagram illustrating yet another example overlay of real time data on angiogram imaging data according to one or more aspects of this disclosure. In some examples, rather than display the angiogram imaging data itself, processing circuitry 204 may control display 206 to display 3D model 232 (or 3D model 306). Processing circuitry 204 may track devices used, e.g., via software, and may control imager 140 to utilize a relatively low frame rate, as discussed above. Processing circuitry 204 may facilitate a clinician interfacing with 3D model 232 (or 3D model 306) to plan the medical procedure.

Figure 32:
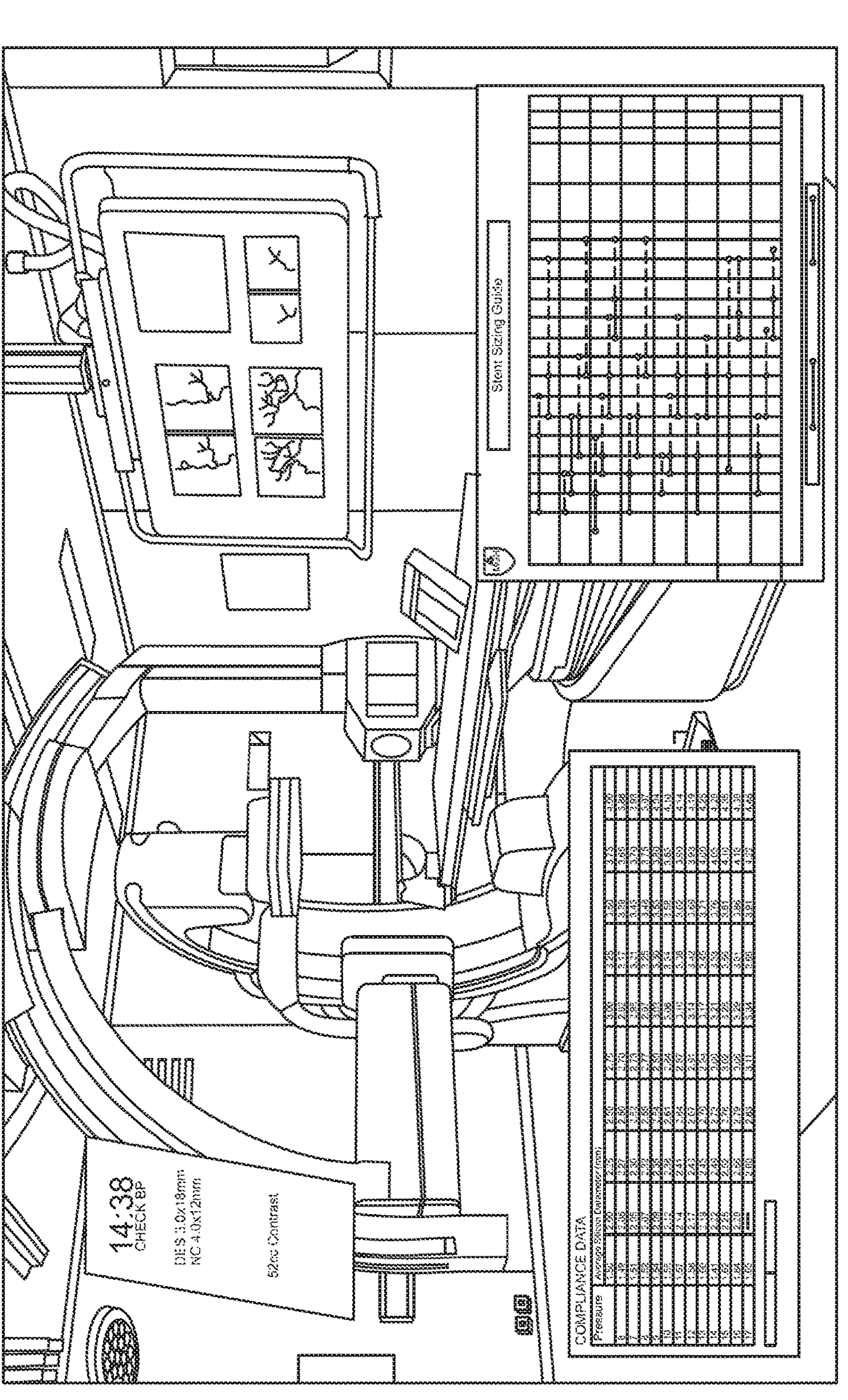
FIG. 32 is a conceptual diagram illustrating an example staff communication board according to one or more aspects of this disclosure.

FIG. 32 is a conceptual diagram illustrating an example staff communication board according to one or more aspects of this disclosure. In some examples, system 100 may include a dedicated display or screen (e.g., display device 110), for example, in a Cath lab, dedicated to communicating to staff information concerning the medical procedure itself, as opposed to communication to a specific clinician (e.g., a physician) about the patient. The information displayed on the dedicated screen may be switchable to be displayed on another display (e.g., display 206) for example via one or more of input device(s) 210.

In some examples, the dedicated display may display a library of useful charts, tables, and/or infographics which may be used by the staff. For example, the dedicated display may display key information which may be needed or desired by nurses and/or technicians during the medical procedure. Such information may include checklists, a clock, a representation of time between medications, reminders to do periodic tasks, or the like. In some examples, the information may include reminders to the staff to take more intrusive measures if certain measures are overdue or as such measures become longer overdue.

In some examples, the dedicated display (or system 100) may include an integrated scanner to help with record keeping. For example, the integrated scanner may be configured to scan QR codes and/or bar codes for inventory management. In some examples, the dedicated display may be voice activated (e.g., via one or more microphones of system 100) to assist with record keeping. For example, a staff member may read out a blood pressure of the patient, devices used or to be used, or updates on the medical procedure. Processing circuitry 204 may execute NLP algorithm(s) 228 to translate the spoken language into a form used for record keeping.

FIG. 33 is a conceptual diagram illustrating an example computer assisted angiogram according to one or more aspects of this disclosure. In some examples, system 100 may include techniques for taking computer assisted angiograms. For example, a clinician may deliver a diagnostic catheter to the vasculature (e.g., a vessel of the coronary vasculature) of the patient. The clinician may walk behind a radiation shield and press a button or otherwise activate system 100 to take the computer assisted angiogram. Processing circuitry 204 may control a C-arm of imager 140 and control an automatic contrast injection device (e.g., of additional equipment 152) to automatically inject contrast into the patient. Processing circuitry 204 executing one or more of ML algorithm(s) 222, AI algorithm(s) 226, and/or computer vision algorithm(s) 224 may automatically find a desired or best view of the vasculature of the patient. In some examples, processing circuitry 204 may provide for the clinician remotely controlling imager 140 from behind the radiation shield to facilitate direct user input and adjustments. In some examples, processing circuitry 204 may read the amount of contrast used. In some examples, processing circuitry 204 may suggest to the clinician to use diluted contrast and/or may automatically control the automatic contrast injection device to used diluted contrast, for example, based on the amount of contrast used during the medical procedure. In some examples, processing circuitry 204 may send captured angiogram imaging data or other captured imaging data to another display device, such as a tablet device, for example, to easily display results to the patient while the patient may still be on table 120.

Figure 34:
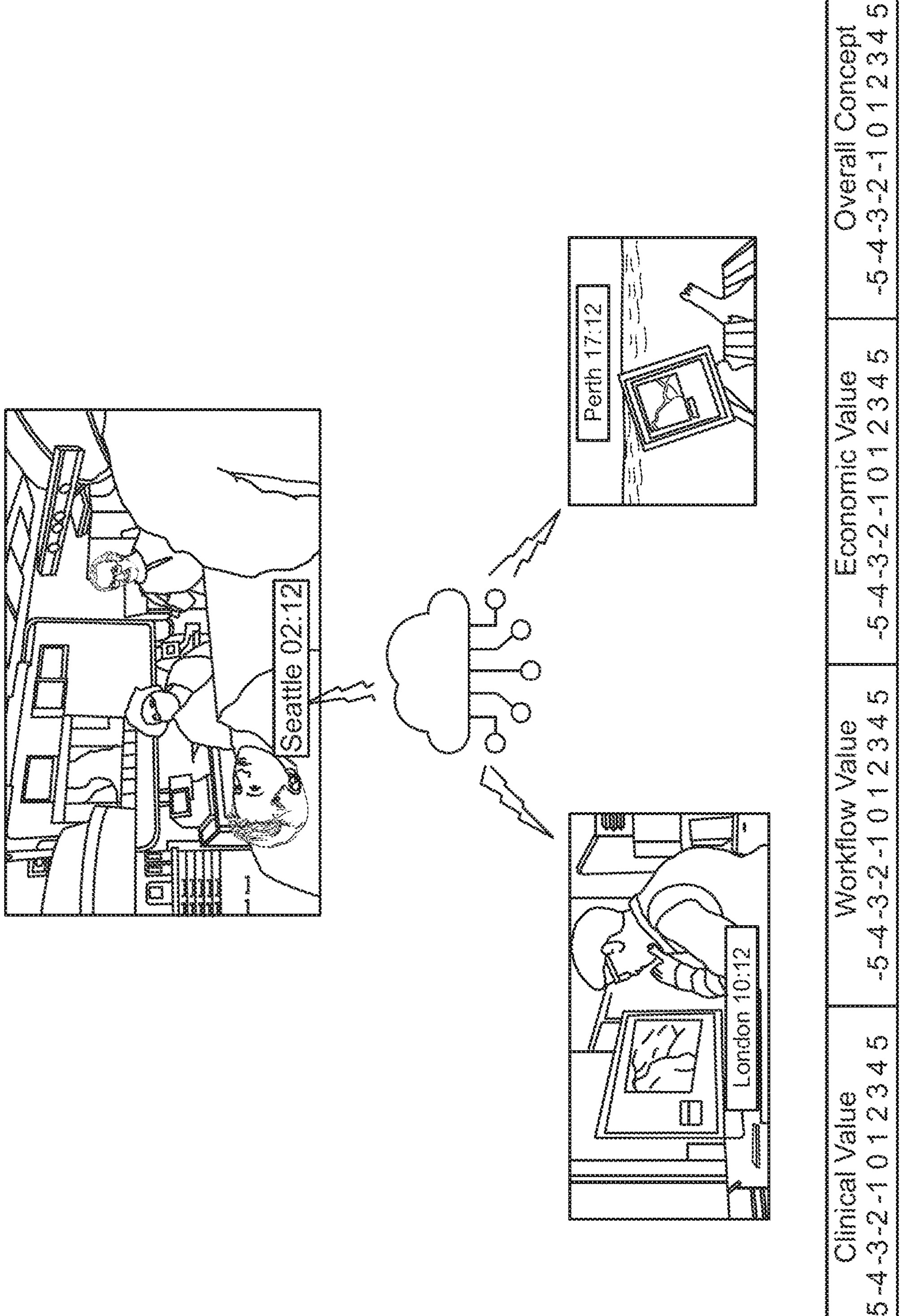
FIG. 34 is a conceptual diagram illustrating an example of real time virtual team techniques according to one or more aspects of this disclosure.

FIG. 34 is a conceptual diagram illustrating an example of real time virtual team techniques according to one or more aspects of this disclosure. In some examples, system 100 may facilitate the use of virtual teams to conduct a medical procedure. For example, system 100 may be configured to stream and/or webcast data captured during a medical procedure through secure platform to a network of trusted advisors. For example, processing circuitry 204 may stream and/or webcast data captured during the medical procedure through network 156 to devices of trusted advisors. For example, this may permit a team of ad-hoc clinicians to review and decide treatment recommendations during the medical procedure.

In some examples, system 100 may include motion tracking cameras (e.g., of additional equipment 152) to control what is displayed on the devices of the trusted advisors during the interface or session while the patient still on table 120. In some examples, system 100 may be configured to automatically generate or otherwise generate a discussion document for case records (e.g., electronic patient record 236) or as a prompt for discussion amongst the trusted advisors during the medical procedure.

Figure 35:
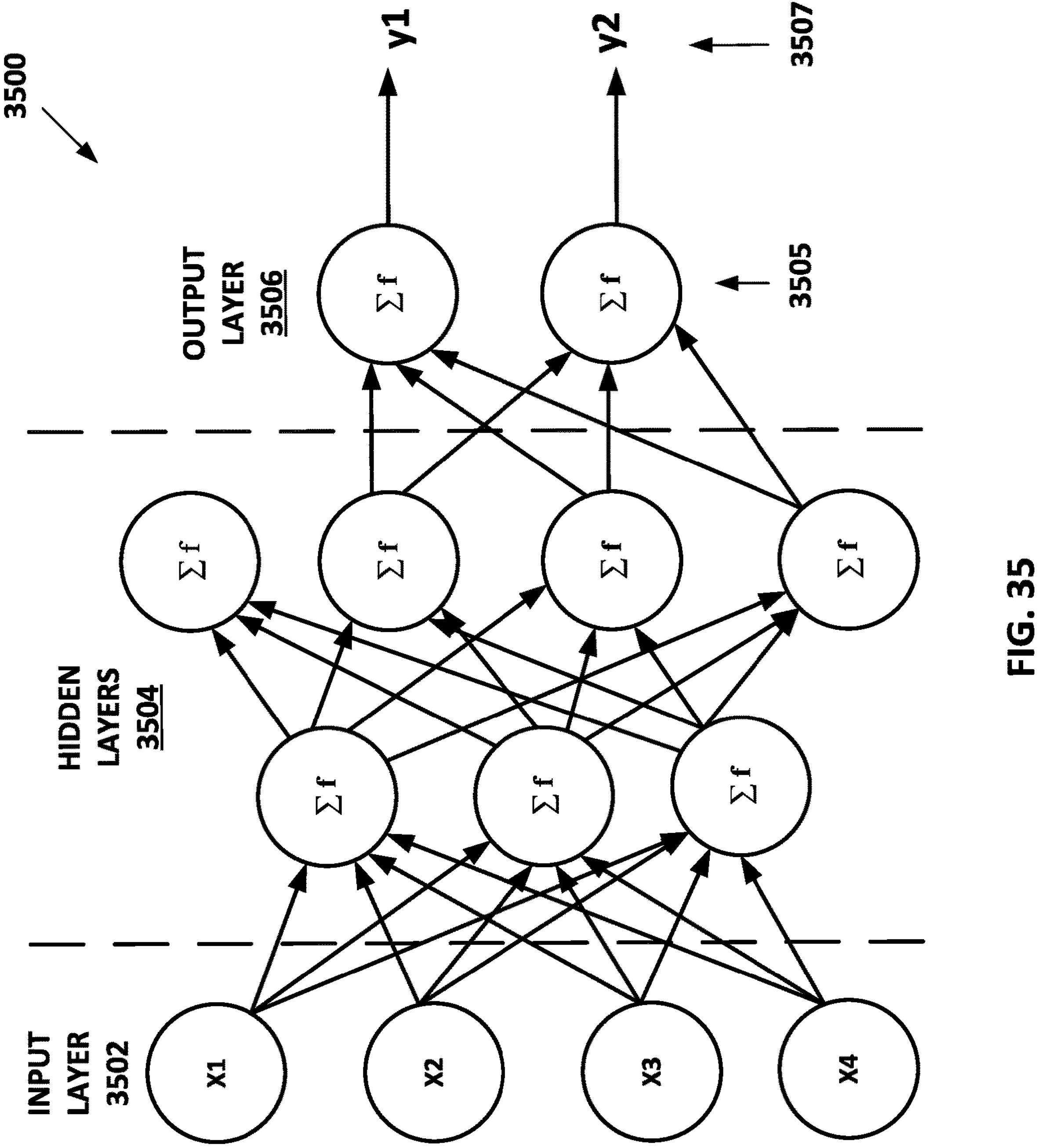
FIG. 35 is a conceptual diagram illustrating an example machine learning model according to one or more aspects of this disclosure.

FIG. 35 is a conceptual diagram illustrating an example machine learning model according to one or more aspects of this disclosure. Machine learning model 3500 may be an example of the ML algorithm(s) 222. In some examples, machine learning model 3500 may be a part of computer vision algorithms(s) 224 and/or NLP algorithm(s) 228. Machine learning model 3500 may be an example of a deep learning model, or deep learning algorithm, trained to determine a patient condition and/or a type of medical procedure. One or more of computing device 150, computing device 200, and/or server 160 may train, store, and/or utilize machine learning model 3500, but other devices of system 100 may apply inputs to machine learning model 3500 in some examples. In some examples, other types of machine learning and deep learning models or algorithms may be utilized in other examples. For example, a convolutional neural network model of ResNet-18 may be used. Some non-limiting examples of models that may be used for transfer learning include AlexNet, VGGNet, GoogleNet, ResNet50, or DenseNet, etc. Some non-limiting examples of machine learning techniques include Support Vector Machines, K-Nearest Neighbor algorithm, and Multi-layer Perceptron.

As shown in the example of FIG. 35, machine learning model 3500 may include three types of layers. These three types of layers include input layer 3502, hidden layers 3504, and output layer 3506. Output layer 3506 comprises the output from the transfer function 3505 of output layer 3506. Input layer 3502 represents each of the input values X1 through X4 provided to machine learning model 3500. In some examples, the input values may include any of the of values input into the machine learning model, as described above. For example, the input values may include 3D model 232, and/or other data as described above. In addition, in some examples input values of machine learning model 3500 may include additional data, such as other data that may be collected by or stored in system 100.

Each of the input values for each node in the input layer 3502 is provided to each node of a first layer of hidden layers 3504. In the example of FIG. 35, hidden layers 3504 include two layers, one layer having four nodes and the other layer having three nodes, but fewer or greater number of nodes may be used in other examples. Each input from input layer 3502 is multiplied by a weight and then summed at each node of hidden layers 3504. During training of machine learning model 3500, the weights for each input are adjusted to establish the relationship between 3D model 232, and treatment pathways/options 230. In some examples, one hidden layer may be incorporated into machine learning model 3500, or three or more hidden layers may be incorporated into machine learning model 3500, where each layer includes the same or different number of nodes.

The result of each node within hidden layers 3504 is applied to the transfer function of output layer 3506. The transfer function may be liner or non-linear, depending on the number of layers within machine learning model 3500. Example non-linear transfer functions may be a sigmoid function or a rectifier function. The output 3507 of the transfer function may be a classification that 3D model 232 is indicative of a specific treatment pathway, and/or the like.

As shown in the example above, by applying machine learning model 3500 to input data such as 3d model 232, processing circuitry 204 is able to determine one or more treatment pathways. This may improve patient outcomes.

Figure 36:
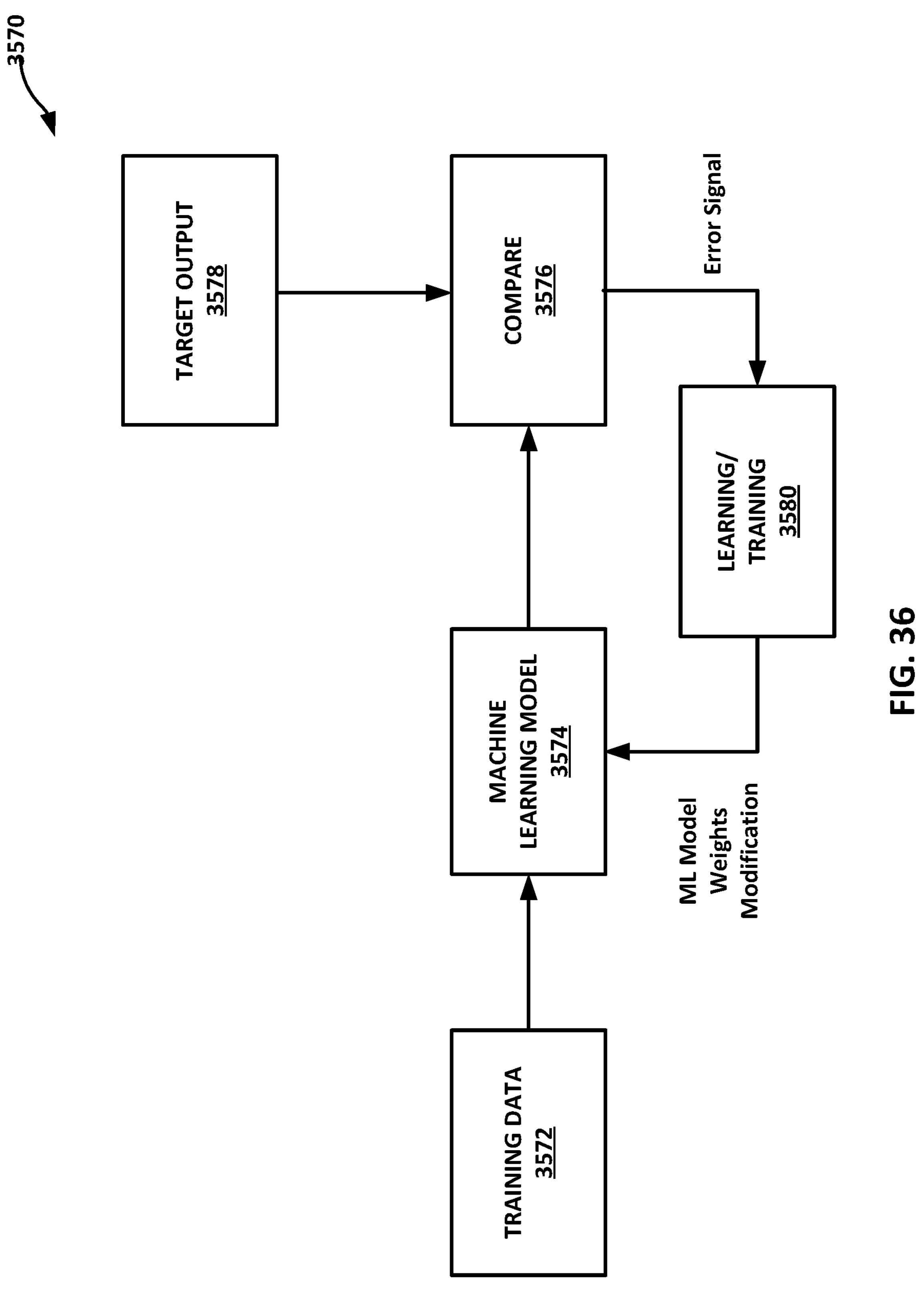
FIG. 36 is a conceptual diagram illustrating an example training process for a machine learning model in accordance with one or more aspects of this disclosure.

FIG. 36 is a conceptual diagram illustrating an example training process for a machine learning model according to one or more aspects of this disclosure. Process 3600 may be used to train machine learning model(s) 7022 (or any other machine learning model discussed herein) and/or computer vision model(s) 7024 (or any other computer vision model discussed herein). A machine learning model 3674 (which may be an example of machine learning model 3500 and/or ML algorithm(s) 222) may be implemented using any number of models for supervised and/or reinforcement learning, such as but not limited to, an artificial neural network, a decision tree, naïve Bayes network, support vector machine, or k-nearest neighbor model, CNN, RNN, LSTM, ensemble network, to name only a few examples. In some examples, one or more of computing device 150, computing device 200, and/or server 160 initially trains machine learning model 3674 based on a corpus of training data 3672. Training data 3672 may include, for example, data collected from past medical procedures, such as imaging data, device data (e.g., including device parameters such as device size, length, device settings, etc.), procedure outcomes, patient outcomes, and/or any other training data described herein.

While training machine learning model 3674, processing circuitry 204 may compare 3676 a prediction or classification with a target output 3678. Processing circuitry 204 may utilize an error signal from the comparison to train (learning/training 3680) machine learning model 3674. Processing circuitry 204 may generate machine learning model weights or other modifications which processing circuitry 204 may use to modify machine learning model 3674. For example, processing circuitry 204 may modify the weights of machine learning model 3500 based on the learning/training 3680. For example, one or more of computing device 150 and/or server 160, may, for each training instance in training data 3672, modify, based on training data 3672, the manner in which a treatment pathway or information associated therewith is determined.

The techniques discussed herein may be used in any combination or alone.

While many of the techniques described herein are attributed to processing circuitry 204, in some examples, such techniques may be performed by server 160, imager 140, additional imager(s) 142, additional equipment 152, other computing devices not shown in FIG. 1, or any combination thereof. Furthermore, while many of the techniques described herein are attributed to display 206, such techniques may be performed by display device 110, other display devices not shown in FIG. 1 or 2, or any combination thereof.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The terms "controller", "processor", or "processing circuitry" may generally refer to any of the foregoing logic circuitry, alone or in combination with other logic circuitry, or any other equivalent circuitry. A control unit comprising hardware may also perform one or more of the techniques of this disclosure. Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), or electronically erasable programmable read only memory (EEPROM), or other computer readable media.

This disclosure includes the following non-limiting examples.

Example 1A

A medical system comprising: memory configured to store a three-dimensional (3D) model of a coronary vasculature of a patient; and processing circuitry communicatively coupled to the memory, the processing circuitry being configured to: obtain first fluoroscopy with contrast imaging data from a first viewing angle; obtain second fluoroscopy with contrast imaging data from a second viewing angle, the second viewing angle being different than the first viewing angle; determine the 3D model of the coronary vasculature of the patient based on the first fluoroscopy with contrast imaging data and the second fluoroscopy with contrast imaging data; obtain additional imaging data, the additional imaging data comprising imaging data from one or more imagers other than a fluoroscopy imager; update the 3D model based on the additional imaging data; and output for display a representation of the updated 3D model.

Example 2A

The medical system of example 1A, wherein the additional imaging data comprises at least one of computed tomography (CT) imaging data, intravenous ultrasound (IVUS) imaging data, optical coherence tomography (OCT) imaging data, near infrared spectroscopy (NIRS) imaging data, ultrasound imaging data, magnetic resonance imaging (MRI) data, or positron emission tomography (PET) imaging data.

Example 3A

The medical system of example 1A or example 2A, wherein the processing circuitry is further configured to: co-register at least one of the first fluoroscopy with contrast imaging data, the second fluoroscopy with contrast imaging data, or the 3D model with the additional imaging data; and output for display the additional imaging data and the at least one of the first fluoroscopy imaging data, the second fluoroscopy imaging data, or the representation of the updated 3D model.

Example 4A

The medical system of any of examples 1A-3A, wherein as part of updating the 3D model, the processing circuitry is configured to: identify at least one area of the coronary vasculature of the patient; prompt a clinician to utilize additional equipment, the additional equipment being configured to determine additional information relating to the identified at least one area of vasculature of the patient; obtain the additional information; and update the 3D model based on the additional information.

Example 5A

The medical system of any or examples 1A-4A, wherein as part of at least one of determining the 3D model or updating the 3D model, the processing circuitry is configured to determine at least one of vessel morphology, plaque location, plaque type, vessel length, vessel diameter, fractional flow reserve (FFR) values, lesion dimensions, orientation of one or more lesions with respect to vessel walls, lipid composition, or SYNTAX scores.

Example 6A

The medical system of any of examples 1A-5A, wherein as part of at least one of determining the 3D model or updating the 3D model, the processing circuitry is further configured to at least one of utilize at least one Digital Imaging and Communications in Medicine (DICOM) file or calibrate at least one measurement off at least one known device measurement reference.

Example 7A

The medical system of any of examples 1A-6A, wherein the processing circuitry is configured to update the 3D model during a percutaneous coronary intervention (PCI) procedure.

Example 8A

The medical system of any of examples 1A-7A, wherein as part of updating the 3D model, the processing circuitry is configured to: obtain third fluoroscopy with contrast imaging data during a percutaneous coronary intervention (PCI) procedure, the third fluoroscopy with contrast imaging data having a lower frame rate than at least one of the first fluoroscopy with contrast imaging data or the second fluoroscopy with contrast imaging data; and update the 3D model based on the third fluoroscopy with contrast imaging data.

Example 9A

The medical system of any of examples 1A-8A, wherein the processing circuitry is further configured to: determine a scaled model for each device used during a percutaneous coronary intervention (PCI) procedure; and output for display a representation of the scaled model for each device used during the PCI procedure.

Example 10A

The medical system of any of examples 1A-9A, wherein as part of at least one of determining the 3D model or updating the 3D model, the processing circuitry is configured to execute an artificial intelligence algorithm.

Example 11A

The medical system of any of examples 1A-10A, wherein as part of updating the 3D model the processing circuitry is further configured to: obtain additional fluoroscopy with contrast imaging data; and update the 3D model based on the additional fluoroscopy with contrast imaging data.

Example 12A

A method comprising: obtaining first fluoroscopy with contrast imaging data from a first viewing angle; obtaining second fluoroscopy with contrast imaging data from a second viewing angle, the second viewing angle being different than the first viewing angle; determining a 3D model of a coronary vasculature of a patient based on the first fluoroscopy with contrast imaging data and the second fluoroscopy with contrast imaging data; obtaining additional imaging data, the additional imaging data comprising imaging data from one or more imagers other than a fluoroscopy imager; updating the 3D model based on the additional imaging data; and outputting for display a representation of the updated 3D model.

Example 13A

The method of example 12A, wherein the additional imaging data comprises at least one of computed tomography (CT) imaging data, intravenous ultrasound (IVUS) imaging data, optical coherence tomography (OCT) imaging data, near infrared spectroscopy (NIRS) imaging data, ultrasound imaging data, magnetic resonance imaging (MRI) data, or positron emission tomography (PET) imaging data.

Example 14A

The method of example 12A or example 13A, further comprising: co-registering at least one of the first fluoroscopy with contrast imaging data, the second fluoroscopy with contrast imaging data, or the 3D model with the additional imaging data; and outputting for display the additional imaging data and the at least one of the first fluoroscopy imaging data, the second fluoroscopy imaging data, or the representation of the updated 3D model.

Example 15A

The method of any of examples 12A-14A, wherein updating the 3D model comprises: identifying at least one area of the coronary vasculature of the patient; prompting a clinician to utilize additional equipment, the additional equipment being configured to determine additional information relating to the identified at least one area of vasculature of the patient; obtaining the additional information; and updating the 3D model based on the additional information.

Example 16A

The method of any or examples 12A-15A, wherein at least one of determining the 3D model or updating the 3D model comprises determining at least one of vessel morphology, plaque location, plaque type, vessel length, vessel diameter, FFR scores, lesion dimensions, orientation of one or more lesions with respect to vessel walls, lipid composition, or SYNTAX scores.

Example 17A

The method of any of examples 15A-16A, wherein at least one of determining the 3D model or updating the 3D model comprises utilizing at least one Digital Imaging and Communications in Medicine (DICOM) file or calibrating at least one measurement off at least one known device measurement reference.

Example 18A

The method of any of examples 12A-17A, wherein the method further comprises updating the 3D model during a percutaneous coronary intervention (PCI) procedure.

Example 19A

The method of any of examples 12A-18A, wherein updating the 3D model comprises: obtaining third fluoroscopy with contrast imaging data during a percutaneous coronary intervention (PCI) procedure, the third fluoroscopy with contrast imaging data having a lower frame rate than at least one of the first fluoroscopy with contrast imaging data or the second fluoroscopy with contrast imaging data; and updating the 3D model based on the third fluoroscopy with contrast imaging data.

Example 20A

The method of any of examples 12A-19A, further comprising: determining a scaled model for each device used during a percutaneous coronary intervention (PCI) procedure; and outputting for display a representation of the scaled model for each device used during the PCI procedure.

Example 21A

The method of any of examples 12A-20A, wherein at least one of determining the 3D model or updating the 3D model, comprises executing an artificial intelligence algorithm.

Example 22A

The method of any of examples 12A-21A, wherein updating the 3D model further comprises: obtaining additional fluoroscopy with contrast imaging data; and updating the 3D model based on the additional fluoroscopy with contrast imaging data.

Example 23A

A non-transitory computer-readable storage medium storing instructions, which, when executed, cause processing circuitry to: obtain first fluoroscopy with contrast imaging data from a first viewing angle; obtain second fluoroscopy with contrast imaging data from a second viewing angle, the second viewing angle being different than the first viewing angle; determine a 3D model of a coronary vasculature of a patient based on the first fluoroscopy with contrast imaging data and the second fluoroscopy with contrast imaging data; obtain additional imaging data, the additional imaging data comprising imaging data from one or more imagers other than a fluoroscopy imager; update the 3D model based on the additional imaging data; and output for display a representation of the updated 3D model.

Example 1B

A medical system comprising: memory configured to store a plurality of treatment pathways; and processing circuitry communicatively coupled to the memory, the processing circuitry being configured to: determine the plurality of treatment pathways; determine, for each respective treatment pathway of the plurality of treatment pathways, one or more respective predicted effectiveness indicators associated with the respective treatment pathway, one or more respective predicted risks associated with the respective treatment pathway, and a respective confidence level associated with at least one of the respective predictions; and output for display the plurality of treatment pathways, the one or more respective predicted effectiveness indicators associated with the respective treatment pathway, the one or more respective predicted risks associated with the respective treatment pathway, and the respective confidence level associated with at least one of the respective predictions for each respective treatment pathway of the plurality of treatment pathways.

Example 2B

The medical system of example 1B, wherein the processing circuitry is further configured to: determine a recommended treatment pathway of the plurality of treatment pathways; and output for display an indication of the recommended treatment pathway.

Example 3B

The medical system of example 1B or example 2B, wherein as part of determining the one or more respective predicted effectiveness indicators associated with the respective treatment pathway, the one or more respective predicted risks associated with the respective treatment pathway, and the respective certainty level associated with at least one of the respective predictions, the processing circuitry is configured to execute a machine learning algorithm.

Example 4B

The medical system of example 3B, wherein as part of determining the one or more respective predicted effectiveness indicators associated with the respective treatment pathway, the one or more respective predicted risks associated with the respective treatment pathway, and the respective certainty level associated with at least one of the respective predictions, the processing circuitry is configured to: generate a 3D model of vasculature of a patient; and execute the machine learning algorithm, using input derived from the 3D model of the vasculature of the patient.

Example 5B

The medical system of any of examples 1B-4B, wherein as part of determining the one or more respective predicted effectiveness indicators associated with the respective treatment pathway, the one or more respective predicted risks associated with the respective treatment pathway, and the respective certainty level associated with at least one of the respective predictions, the processing circuitry is configured to run a plurality of simulations.

Example 6B

The medical system of any of examples 1B-5B, wherein the processing circuitry is configured to determine the one or more respective predicted effectiveness indicators associated with the respective treatment pathway based on a device performance prediction.

Example 7B

The medical system of any of examples 1B-6B, wherein the one or more respective predicted effectiveness indicators associated with the respective treatment pathway comprises at least one of a respective predicted fractional flow reserve (FFR) value, a respective predicted quality of life improvement, or at least one respective predicted readmission rate.

Example 8B

The medical system of any of examples 1B-7B, wherein each of the plurality of treatment pathways further comprises at least one of a respective inventory availability or cost.

Example 9B

The medical system of any of examples 1B-8B, wherein, in response to clinician input of a selected one of the plurality of treatment pathways, the processing circuitry is configured to: determine a plurality of treatment options of the selected treatment pathway, each of the plurality of treatment options comprising one or more respective predicted effectiveness indicators associated with the respective treatment option, one or more respective predicted risks associated with the respective treatment option, a respective confidence level associated with at least one of the respective predictions for the respective treatment option, and suggested device parameters for the respective treatment option; and output for display the plurality of treatment options of the selected treatment pathway, and the one or more respective predicted effectiveness indicators associated with the respective treatment option, the one or more respective predicted risks associated with the respective treatment option, the respective confidence level associated with at least one of the respective predictions for the respective treatment option, and the suggested device parameters for the respective treatment option.

Example 10B

The medical system of any of examples 1B-9B, wherein the processing circuitry is further configured to: during a percutaneous coronary intervention (PCI) procedure, determine a live reading, the live reading comprising one or more live predicted effectiveness indicators associated with the PCI procedure, one or more live risks associated with the PCI procedure, a live certainty level associated with at least one of the respective predictions for the PCI procedure, and live suggested device parameters for the PCI procedure; and output for display one of the plurality of treatment options and the live reading.

Example 11B

The medical system of any of examples 1B-10B, wherein the processing circuitry is further configured to: determine at least one of a ghosted preview of the procedure, a graphical predicted FFR, a graphical predicted risk of rupture, or a graphical predicted probability of a successful outcome; and output for display, during a PCI procedure, at least one of the ghosted preview of the procedure, the graphical predicted FFR, the graphical predicted risk of rupture, or the graphical predicted probability of a successful outcome.

Example 12B

A method comprising: determining a plurality of treatment pathways; determining, for each respective treatment pathway of the plurality of treatment pathways, one or more respective predicted effectiveness indicators associated with the respective treatment pathway, one or more respective predicted risks associated with the respective treatment pathway, and a respective confidence level associated with at least one of the respective predictions; and outputting for display the plurality of treatment pathways, and the one or more respective predicted effectiveness indicators associated with the respective treatment pathway, the one or more respective predicted risks associated with the respective treatment pathway, and the respective confidence level associated with at least one of the respective predictions for each respective treatment pathway of the plurality of treatment pathways.

Example 13B

The method of example 12B, further comprising: determining a recommended treatment pathway of the plurality of treatment pathways; and outputting for display an indication of the recommended treatment pathway.

Example 14B

The method of example 12B or example 13B, wherein determining the one or more respective predicted effectiveness indicators associated with the respective treatment pathway, the one or more respective predicted risks associated with the respective treatment pathway, and the respective certainty level associated with at least one of the respective predictions comprises executing a machine learning algorithm.

Example 15B

The method of example 14B, wherein determining the one or more respective predicted effectiveness indicators associated with the respective treatment pathway, the one or more respective predicted risks associated with the respective treatment pathway, and the respective certainty level associated with at least one of the respective predictions, comprises: generating a 3D model of vasculature of a patient; and executing the machine learning algorithm, using input derived from the 3D model of the vasculature of the patient.

Example 16B

The method of any of examples 12B-15B, wherein determining the one or more respective predicted effectiveness indicators associated with the respective treatment pathway, the one or more respective predicted risks associated with the respective treatment pathway, and the respective certainty level associated with at least one of the respective predictions comprises running a plurality of simulations.

Example 17B

The method of any of examples 12B-16B, wherein determining the one or more respective predicted effectiveness indicators associated with the respective treatment pathway is based on a device performance prediction.

Example 18B

The method of any of examples 12B-17B, wherein the one or more respective predicted effectiveness indicators associated with the respective treatment pathway comprises at least one of a respective predicted fractional flow reserve (FFR) value, a respective predicted quality of life improvement, or at least one respective predicted readmission rate.

Example 19B

The method of any of examples 12B-18B, wherein each of the plurality of treatment pathways further comprises at least one of a respective inventory availability or cost.

Example 20B

The method of any of examples 12B-19B, wherein the method further comprises: in response to clinician input of a selected one of the plurality of treatment pathways, determining a plurality of treatment options of the selected treatment pathway, each of the plurality of treatment options comprising one or more respective predicted effectiveness indicators associated with the respective treatment option, one or more respective predicted risks associated with the respective treatment option, a respective confidence level associated with at least one of the respective predictions for the respective treatment option, and suggested device parameters for the respective treatment option; and outputting for display the plurality of treatment options of the selected treatment pathway, and the one or more respective predicted effectiveness indicators associated with the respective treatment option, the one or more respective predicted risks associated with the respective treatment option, the respective confidence level associated with at least one of the respective predictions for the respective treatment option, and the suggested device parameters for the respective treatment option.

Example 21B

The method of any of examples 12B-20B, further comprising: during a percutaneous coronary intervention (PCI)

procedure, determining a live reading, the live reading comprising one or more live predicted effectiveness indicators associated with the PCI procedure, one or more live risks associated with the PCI procedure, a live certainty level associated with at least one of the respective predictions for the PCI procedure, and live suggested device parameters for the PCI procedure; and outputting for display one of the plurality of treatment options and the live reading.

Example 22B

The method of any of examples 12B-21B, further comprising: determining at least one of a ghosted preview of the procedure, a graphical predicted FFR, a graphical predicted risk of rupture, or a graphical predicted probability of a successful outcome; and outputting for display, during a PCI procedure, at least one of the ghosted preview of the procedure, the graphical predicted FFR, the graphical predicted risk of rupture, or the graphical predicted probability of a successful outcome.

Example 23B

A non-transitory computer-readable storage medium storing instructions, which, when executed, cause processing circuitry to: determine a plurality of treatment pathways; determine, for each respective treatment pathway of the plurality of treatment pathways, one or more respective predicted effectiveness indicators associated with the respective treatment pathway, one or more respective predicted risks associated with the respective treatment pathway, and a respective confidence level associated with at least one of the respective predictions; and output for display the plurality of treatment pathways, and the one or more respective predicted effectiveness indicators associated with the respective treatment pathway, the one or more respective predicted risks associated with the respective treatment pathway, and the respective confidence level associated with at least one of the respective predictions for each respective treatment pathway of the plurality of treatment pathways.

Example 1C

A medical system comprising: memory configured to store at least one of clinical guidance or informatics for a percutaneous coronary intervention (PCI) procedure; and processing circuitry communicatively coupled to the memory, the processing circuitry being configured to: obtain angiogram imaging data of a coronary vasculature of a patient; determine the at least one of the clinical guidance or the informatics based at least in part on the angiogram imaging data; and output for display the angiogram imaging data and the at least one of the clinical guidance or the informatics, wherein at least a portion of the at least one of the clinical guidance or the informatics is overlaid onto the angiogram imaging data.

Example 2C

The medical system of example 1C, wherein the at least a portion of the at least one of the clinical guidance or the informatics comprises a heat map, the heat map comprising at least one ghost image of previous device placements or previous device locations.

Example 3C

The medical system of example 1C or example 2C, wherein the at least a portion of the at least one of the clinical guidance or the informatics comprises procedural guidance for at least one of a bifurcation procedure or a balloon procedure.

Example 4C

The medical system of any of examples 1C-3C, wherein the at least a portion of the at least one of the clinical guidance or the informatics comprises at least one of a lesion histology overlay, length markers, or a stent overlay.

Example 5C

The medical system of any of examples 1C-4C, wherein the at least one of the clinical guidance or the informatics comprises at least one suggestion of a device to be used during a clinical procedure, the suggestion comprising at least one of device type, a device shape, or a device size.

Example 6C

The medical system of any of examples 1C-5C, wherein the at least one of the clinical guidance or the informatics comprises instructions for use of a device to be used during a clinical procedure.

Example 7C

The medical system of any of examples 1C-6C, wherein the at least one of the clinical guidance or the informatics comprises at least one suggestion of a location to treat, positioning of a device, or device settings.

Example 8C

The medical system of any of examples 1C-7C, wherein the processing circuitry is further configured to track one or more locations, in real time, of one or more devices in the coronary vasculature of the patient, and wherein the at least a portion of the at least one of the clinical guidance or the informatics comprises a representation of the one or more devices at the one or more locations in the coronary vasculature of the patient during a clinical procedure.

Example 9C

The medical system of any of examples 1C-8C, wherein the at least one of the clinical guidance or the informatics comprises at least one of: real time feedback during the clinical procedure, wherein the real time feedback comprises live risk evaluation of at least one action during the clinical procedure; or at least one prediction based on a device location with respect to specific anatomy of the coronary vasculature of the patient.

Example 10C

The medical system of any of examples 1C-9C, wherein the processing circuitry is further configured to track any substances administered, wherein as part of tracking any substances administered, the processing circuitry is configured to track a time administered, track a volume administered, and track a type of substance administered, and wherein the any substances comprise at least one of medication or contrast.

Example 11C

The medical system of any of examples 1C-10C, wherein the processing circuitry is further configured to: determine an amount of radiation the patient has been exposed to in a predetermined time period; determine a first amount of contrast for imaging; and automatically control an injection device to inject a second amount of contrast based on the determined amount of radiation the patient has been exposed to in the predetermined time period and the determined first amount of contrast.

Example 12C

The medical system of any of examples 1C-11C, wherein the at least one of the clinical guidance or the informatics comprises at least one of: one or more recommendations of positioning, based on a first angiogram of the angiogram imaging data, of imaging equipment, for generation of additional imaging data; one or more recommendations of a procedure to be performed; one or more real time suggestions on one or more devices to be used during the procedure; a comparison of predicted outcomes of at least two potential procedures; personalized guidance based on a clinician to be performing a procedure; or one or more lesion preparation strategies.

Example 13C

The medical system of any of examples 1C-12C, wherein the at least a portion of the at least one of the clinical guidance or the informatics comprises at least one pop-up box, the at least one pop-up box identifying at least one of a vessel, calcium, or a previously implanted stent.

Example 14C

The medical system of any of examples 1C-13C, wherein the at least one of the clinical guidance or the informatics comprises real time auto-identified plaque morphology and the at least a portion of the clinical guidance comprises a highlighted vessel vulnerability.

Example 15C

The medical system of any of examples 1C-14C, wherein the at least one of the clinical guidance or the informatics comprises additional information co-registered with the angiogram imaging data, the additional information comprising at least one of intravascular ultrasound (IVUS) imaging data, optical coherence tomography (OCT) imaging data, one or more fractional flow reserve (FFR) values, or near infrared spectroscopy (NIRS) imaging data.

Example 16C

The medical system of any of examples 1C-15C, wherein the processing circuitry is further configured to output for display information from a previous procedure of the patient and information from a current procedure, wherein the information from the current procedure comprises highlighted changes in the coronary vasculature of the patient from the previous procedure to the current procedure; and wherein the processing circuitry is further configured to determine a nature of a lesion based at least in part on at least one of the changes in the coronary vasculature of the patient or the angiogram imaging data.

Example 17C

A method comprising: obtaining angiogram imaging data of a coronary vasculature of a patient; determining at least one of clinical guidance or informatics based at least in part on the angiogram imaging data; and outputting for display the angiogram imaging data and the at least one of the clinical guidance or the informatics, wherein at least a portion of the at least one of the clinical guidance or the informatics is overlaid onto the angiogram imaging data.

Example 18C

The method of example 17C, wherein the at least a portion of the at least one of the clinical guidance or the informatics comprises a heat map, the heat map comprising at least one ghost image of previous device placements or previous device locations.

Example 19C

The method of example 17C or example 18C, wherein the at least a portion of the at least one of the clinical guidance or the informatics comprises procedural guidance for at least one of a bifurcation procedure or a balloon procedure.

Example 20C

The method of any of examples 17C-19C, wherein the at least a portion of the at least one of the clinical guidance or the informatics comprises at least one of a lesion histology overlay, length markers, or a stent overlay.

Example 21C

The method of any of examples 17C-20C, wherein the at least one of the clinical guidance or the informatics comprises at least one suggestion of a device to be used during a clinical procedure, the suggestion comprising at least one of device type, a device shape, or a device size.

Example 22C

The method of any of examples 17C-21C, wherein the at least one of the clinical guidance or the informatics comprises instructions for use of a device to be used during a clinical procedure.

Example 23C

The method of any of examples 17C-22C, wherein the at least one of the clinical guidance or the informatics comprises at least one suggestion of a location to treat, positioning of a device, or device settings.

Example 24C

The method of any of examples 17C-23C, further comprising tracking one or more locations, in real time, of one or more devices in the coronary vasculature of the patient, and wherein the at least a portion of the at least one of the clinical guidance or the informatics comprises a representation of the one or more devices at the one or more locations in the coronary vasculature of the patient during a clinical procedure.

Example 25C

The method of any of examples 17C-24C, wherein the at least one of the clinical guidance or the informatics comprises at least one of: real time feedback during the clinical procedure, wherein the real time feedback comprises live risk evaluation of at least one action during the clinical procedure; or at least one prediction based on a device location with respect to specific anatomy of the coronary vasculature of the patient.

Example 26C

The method of any of examples 17C-25C, further comprising tracking any substances administered, wherein tracking any substances administered comprises tracking a time administered, tracking a volume administered, and tracking a type of substance administered, and wherein the any substances comprise at least one of medication or contrast.

Example 27C

The method of any of examples 17C-26C, further comprising: determining an amount of radiation the patient has been exposed to in a predetermined time period; determining a first amount of contrast for imaging; and automatically controlling an injection device to inject a second amount of contrast based on the determined amount of radiation the patient has been exposed to in the predetermined time period and the determined first amount of contrast.

Example 28C

The method of any of examples 17C-27C, wherein the at least one of the clinical guidance or the informatics comprises at least one of: one or more recommendations of positioning, based on a first angiogram of the angiogram imaging data, of imaging equipment, for generation of additional imaging data; one or more recommendations of a procedure to be performed; one or more real time suggestions on one or more devices to be used during the procedure; a comparison of predicted outcomes of at least two potential procedures; personalized guidance based on a clinician to be performing a procedure; or one or more lesion preparation strategies.

Example 29C

The method of any of examples 17C-28C, wherein the at least a portion of the at least one of the clinical guidance or the informatics comprises at least one pop-up box, the at least one pop-up box identifying at least one of a vessel, calcium, or a previously implanted stent.

Example 30C

The method of any of examples 17C-29C, wherein the at least one of the clinical guidance or the informatics comprises real time auto-identified plaque morphology and the at least a portion of the clinical guidance comprises a highlighted vessel vulnerability.

Example 31C

The method of any of examples 17C-30C, wherein the at least one of the clinical guidance or the informatics comprises additional information co-registered with the angiogram imaging data, the additional information comprising at least one of intravascular ultrasound (IVUS) imaging data, optical coherence tomography (OCT) imaging data, one or more fractional flow reserve (FFR) values, or near infrared spectroscopy (NIRS) imaging data.

Example 32C

The method of any of examples 17C-31C, further comprising outputting for display information from a previous procedure of the patient and information from a current procedure, wherein the information from the current procedure comprises highlighted changes in the coronary vasculature of the patient from the previous procedure to the current procedure; and wherein the method further comprises determining a nature of a lesion based at least in part on at least one of the changes in the coronary vasculature of the patient or the angiogram imaging data.

Example 33C

A non-transitory computer-readable storage medium storing instructions, which, when executed, cause processing circuitry to: obtain angiogram imaging data of a coronary vasculature of a patient; determine at least one of clinical guidance or informatics based at least in part on the angiogram imaging data; and output for display the angiogram imaging data and the at least one of the clinical guidance or informatics, wherein at least a portion of the at least one of the clinical guidance or the informatics is overlaid onto the angiogram imaging data.

Various examples have been described. These and other examples are within the scope of the following claims.

What is claimed is:

1. A medical system comprising:
- memory configured to store at least one of clinical guidance or informatics for a percutaneous coronary intervention (PCI) procedure; and
- processing circuitry communicatively coupled to the memory, the processing circuitry being configured to:
  - obtain angiogram imaging data of a coronary vasculature of a patient;
  - determine the at least one of the clinical guidance or the informatics based at least in part on the angiogram imaging data; and
  - output for display the angiogram imaging data and the at least one of the clinical guidance or the informatics, wherein at least a portion of the at least one of the clinical guidance or the informatics is overlaid onto the angiogram imaging data,
- wherein the at least one of the clinical guidance or the informatics comprises at least one of:
- one or more recommendations of positioning, based on a first angiogram of the angiogram imaging data, of imaging equipment, for generation of additional imaging data;
- one or more recommendations of a procedure to be performed;
- one or more real time suggestions on one or more devices to be used during the procedure;
- a comparison of predicted outcomes of at least two potential procedures;
- personalized guidance based on a clinician to be performing a procedure; or
- one or more lesion preparation strategies.

2. The medical system of claim 1, wherein the at least a portion of the at least one of the clinical guidance or the informatics comprises a heat map, the heat map comprising at least one ghost image of previous device placements or previous device locations.

3. The medical system of claim 1, wherein the at least a portion of the at least one of the clinical guidance or the informatics comprises procedural guidance for at least one of a bifurcation procedure or a balloon procedure.

4. The medical system of claim 1, wherein the at least a portion of the at least one of the clinical guidance or the informatics comprises at least one of a lesion histology overlay, length markers, or a stent overlay.

5. The medical system of claim 1, wherein the at least one of the clinical guidance or the informatics comprises at least one suggestion of a device to be used during a clinical procedure, the suggestion comprising at least one of device type, a device shape, or a device size.

6. The medical system of claim 1, wherein the at least one of the clinical guidance or the informatics comprises instructions for use of a device to be used during a clinical procedure.

7. The medical system of claim 1, wherein the at least one of the clinical guidance or the informatics comprises at least one suggestion of a location to treat, positioning of a device, or device settings.

8. The medical system of claim 1, wherein the processing circuitry is further configured to track one or more locations, in real time, of one or more devices in the coronary vasculature of the patient, and wherein the at least a portion of the at least one of the clinical guidance or the informatics comprises a representation of the one or more devices at the one or more locations in the coronary vasculature of the patient during a clinical procedure.

9. The medical system of claim 1, wherein the at least one of the clinical guidance or the informatics comprises at least one of:

real time feedback during a clinical procedure, wherein the real time feedback comprises live risk evaluation of at least one action during the clinical procedure; or at least one prediction based on a device location with respect to specific anatomy of the coronary vasculature of the patient.

10. The medical system of claim 1, wherein the processing circuitry is further configured to track any substances administered, wherein as part of tracking any substances administered, the processing circuitry is configured to track a time administered, track a volume administered, and track a type of substance administered, and wherein the any substances comprise at least one of medication or contrast.

11. The medical system of claim 1, wherein the processing circuitry is further configured to:

determine an amount of radiation the patient has been exposed to in a predetermined time period;

determine a first amount of contrast for imaging; and automatically control an injection device to inject a second amount of contrast based on the determined amount of radiation the patient has been exposed to in the predetermined time period and the determined first amount of contrast.

12. The medical system of claim 1, wherein the at least a portion of the at least one of the clinical guidance or the informatics comprises at least one pop-up box, the at least one pop-up box identifying at least one of a vessel, calcium, or a previously implanted stent.

13. The medical system of claim 1, wherein the at least one of the clinical guidance or the informatics comprises real time auto-identified plaque morphology and the at least a portion of the clinical guidance comprises a highlighted vessel vulnerability.

14. The medical system of claim 1, wherein the at least one of the clinical guidance or the informatics comprises additional information co-registered with the angiogram imaging data, the additional information comprising at least one of intravascular ultrasound (IVUS) imaging data, optical coherence tomography (OCT) imaging data, one or more fractional flow reserve (FFR) values, or near infrared spectroscopy (NIRS) imaging data.

15. The medical system of claim 1, wherein the processing circuitry is further configured to output for display information from a previous procedure of the patient and information from a current procedure, wherein the information from the current procedure comprises highlighted changes in the coronary vasculature of the patient from the previous procedure to the current procedure; and wherein the processing circuitry is further configured to determine a nature of a lesion based at least in part on at least one of the highlighted changes in the coronary vasculature of the patient or the angiogram imaging data.

16. A method comprising:

obtaining angiogram imaging data of a coronary vasculature of a patient;

determining at least one of clinical guidance or informatics based at least in part on the angiogram imaging data; and outputting for display the angiogram imaging data and the at least one of the clinical guidance or the informatics, wherein at least a portion of the at least one of the clinical guidance or the informatics is overlaid onto the angiogram imaging data, wherein the at least one of the clinical guidance or the informatics comprises at least one of:

one or more recommendations of positioning, based on a first angiogram of the angiogram imaging data, of imaging equipment, for generation of additional imaging data;

one or more recommendations of a procedure to be performed;

one or more real time suggestions on one or more devices to be used during the procedure;

a comparison of predicted outcomes of at least two potential procedures;

personalized guidance based on a clinician to be performing a procedure; or one or more lesion preparation strategies.

17. The method of claim 16, wherein the at least a portion of the at least one of the clinical guidance or the informatics comprises a heat map, the heat map comprising at least one ghost image of previous device placements or previous device locations.

18. The method of claim 16, wherein the at least a portion of the at least one of the clinical guidance or the informatics comprises procedural guidance for at least one of a bifurcation procedure or a balloon procedure.

19. Non-transitory computer-readable storage media storing instructions, which, when executed, cause processing circuitry to:

obtain angiogram imaging data of a coronary vasculature of a patient;

determine at least one of clinical guidance or informatics based at least in part on the angiogram imaging data; and output for display the angiogram imaging data and the at least one of the clinical guidance or informatics, wherein at least a portion of the at least one of the clinical guidance or the informatics is overlaid onto the angiogram imaging data, wherein the at least one of the clinical guidance or the informatics comprises at least one of:

one or more recommendations of positioning, based on a first angiogram of the angiogram imaging data, of imaging equipment, for generation of additional imaging data;

one or more recommendations of a procedure to be performed;

one or more real time suggestions on one or more devices to be used during the procedure;

a comparison of predicted outcomes of at least two potential procedures;

personalized guidance based on a clinician to be performing a procedure; or one or more lesion preparation strategies.

* * * * *